(12) United States Patent
Körner et al.

(10) Patent No.: US 11,530,982 B2
(45) Date of Patent: Dec. 20, 2022

(54) METHOD AND FOURIER TRANSFORMATION SPECTROMETER WITH DOUBLE BEAM INTERFEROMETER FOR SINGLE SHOT IMAGING FOURIER SPECTROSCOPY

(71) Applicant: Universitat Stuttgart, Stuttgart (DE)

(72) Inventors: Klaus Körner, Berlin (DE); Alois M. Herkommer, Aalen (DE)

(73) Assignee: Universität Stuttgart

( * ) Notice: Subject to any disclaimer, the term of this patent is extended or adjusted under 35 U.S.C. 154(b) by 0 days.

(21) Appl. No.: 17/217,939

(22) Filed: Mar. 30, 2021

(65) Prior Publication Data

US 2021/0310938 A1 Oct. 7, 2021

(30) Foreign Application Priority Data

Mar. 31, 2020 (EP) ..................................... 20167242

(51) Int. Cl.
  *G01N 21/31* (2006.01)
  *G01N 21/45* (2006.01)
  *A61B 5/00* (2006.01)
(52) U.S. Cl.
  CPC ............. *G01N 21/31* (2013.01); *G01N 21/45* (2013.01); *A61B 5/0075* (2013.01); *G01N 2201/0636* (2013.01); *G01N 2201/0638* (2013.01)
(58) Field of Classification Search
  CPC . G01J 2003/2826; G01J 3/2823; G01J 9/0215
  See application file for complete search history.

(56) References Cited

U.S. PATENT DOCUMENTS 1,565,533 A 12/1925 Twyman et al.
3,684,379 A 8/1972 Girard
(Continued)

FOREIGN PATENT DOCUMENTS

CN 106338342 A 1/2017
DE 689 06 154 T2 8/1993
(Continued)

OTHER PUBLICATIONS

Svensson, Thomas, "Design, calibration and characterization of a low-cost spatial Fourier transform LWIR hyperspectral camera with spatial and temporal scanning modes", SPIES, 2018 (Year: 2018).*
(Continued)

*Primary Examiner* — Maurice C Smith
(74) *Attorney, Agent, or Firm* — Shook, Hardy & Bacon L.L.P.

(57) ABSTRACT

Fourier Transformation Spectrometer, FT Spectrometer, comprising: A double beam interferometer, comprising: At least one beam splitter unit (622; 623; 624, 625, 626, 627; 636; 673, 674, 675) for splitting an incident light beam (EB) of a spatially expanded object into a first partial beam (TB1) and a second partial beam (TB2); at least a first beam deflection unit (630; 641; 651; 661; 697) designed to deflect the first partial beam (TB1) at least a first and a second time, wherein the second beam deflection unit (630) is designed to also deflect the second partial beam (TB2) at least at first and a second time; or the double beam interferometer comprises a second beam deflection unit (642; 652; 662) designed to deflect the second partial beam (TB2) at least a first and a second time, wherein the beam deflection unit is also designed to at least partially spatially overlay the first partial beam (TB1) and the second partial beam (TB2), and the respectively first and second deflection of the first partial beam (TB1) and of the second partial beam (TB2) generates
(Continued)

a lateral shear (s); at least a first field of view discriminator unit (BFD1; 631; 645; 653; 656; 666; 677; 976) arranged such that the first partial beam (TB1) is spatially selected after the splitting and prior to the second deflection; at least a second field of view discriminator unit (BFD2; 632; 646; 654; 657; 667; 678; 977) arranged such that the second partial beam (TB2) is spatially selected after the splitting and prior to the second deflection.

19 Claims, 30 Drawing Sheets

(56) References Cited

U.S. PATENT DOCUMENTS

| | | | |
|---|---|---|---|
| 4,523,846 | A | 6/1985 | Breckinridge et al. |
| 4,976,542 | A | 12/1990 | Smith |
| 5,131,747 | A | 7/1992 | Cerutti-Maori et al. |
| 5,539,517 | A | 7/1996 | Cabib et al. |
| 5,541,728 | A | 7/1996 | Dierking |
| 5,777,736 | A | 7/1998 | Horton |
| 6,930,781 | B2 | 8/2005 | Agladze et al. |
| 8,934,104 | B2 | 1/2015 | Koerner et al. |
| 2012/0307258 | A1* | 12/2012 | Koerner ............ G01B 9/02061 356/497 |
| 2019/0162520 | A1 | 5/2019 | Shaked et al. |

FOREIGN PATENT DOCUMENTS

| | | |
|---|---|---|
| DE | 10 2010 006 239 B3 | 3/2011 |
| EP | 2 526 373 B1 | 12/2013 |
| WO | 2013/140396 A1 | 9/2013 |

OTHER PUBLICATIONS

Anatoly Efimov, "Lateral-shearing, delay-dithering Mach-Zehnder interferometer for spatial coherence measurement", Optics Letters, 2013 (Year: 2013).*

Gao, P., et al., "Parallel two-step phase-shifting point-diffraction interferometry for microscopy based on a pair of cube beamsplitters", Optics Express, vol. 19, No. 3, pp. 1-6 (Jan. 31, 2011).

Hirai, A., et al., "Application of Multiple-Image Fourier Transform Spectral Imaging to Measurement of Fast Phenomena", Optical Review, vol. 1, No. 2, pp. 205-207 (1994).

Kelsall, D., "Optical Frequency Response Characteristics in the presence of Spherical Aberration measured by an automatically recording Interferometric Instrument", DepartJnent of Physics, pp. 465-479 (1958).

Kudenov, M. W., and Dereniak, E. L., "Compact Snapshot Real-Time Imaging Spectrometer", Electro-Optical Remote Sensing, Proc. of SPIE, pp. 1-12 (2011).

Liu, C., et al., "Large field-of-view Fourier transform imaging spectrometer using dual-channel stitching", Optics Express, vol. 24, No. 25, pp. 28473-28490 (Dec. 12, 2016).

Malacara, D., "Optical Shop Testing", Second Edition, John Wiley & Sons, Inc., pp. 3 (1992).

Okamoto, T., et al., "Fourier Transform Spectrometer With A Self-Scanning Photodiode Array", Applied Optics, vol. 23, No. 2, pp. 269-273 (Jan. 15, 1984).

Wu, Y., et al., "Global estimates of lunar iron and titanium contents from the Chang' E-1 IIM data", Journal Of Geophysical Research, vol. 117, E02001, pp. 1-23 (2012).

* cited by examiner

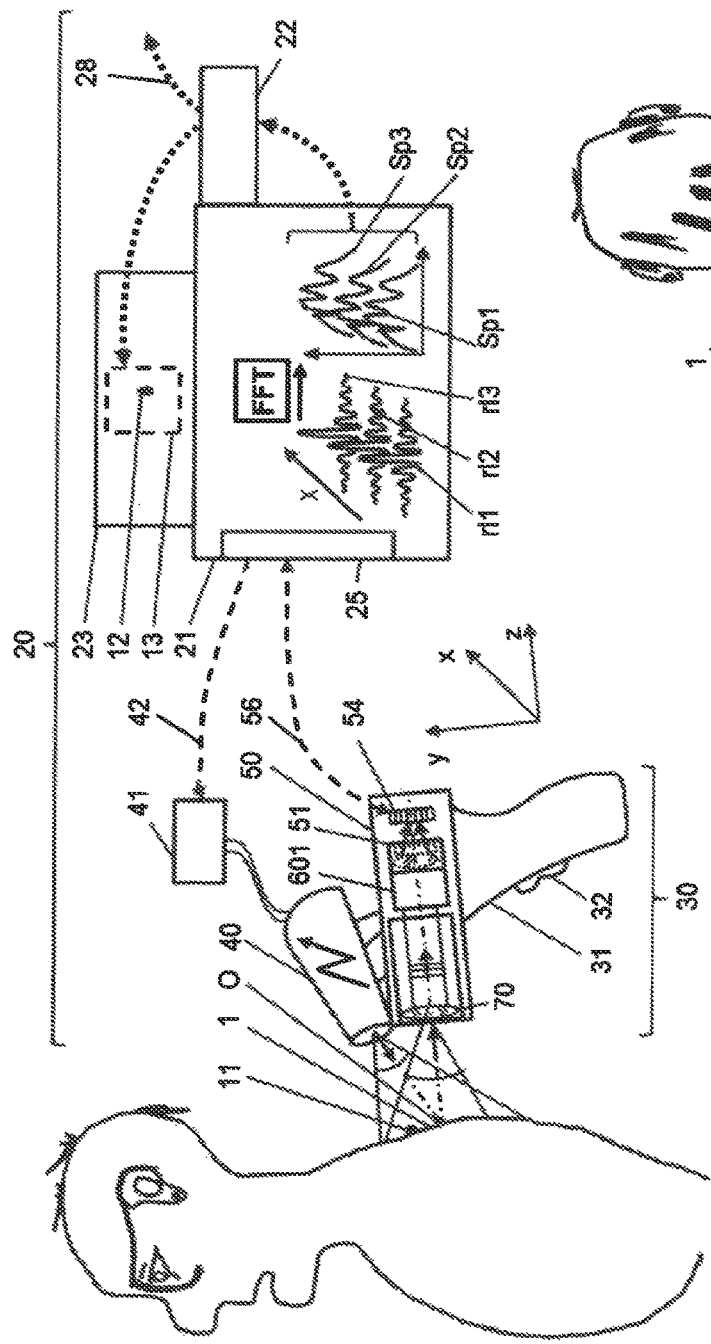

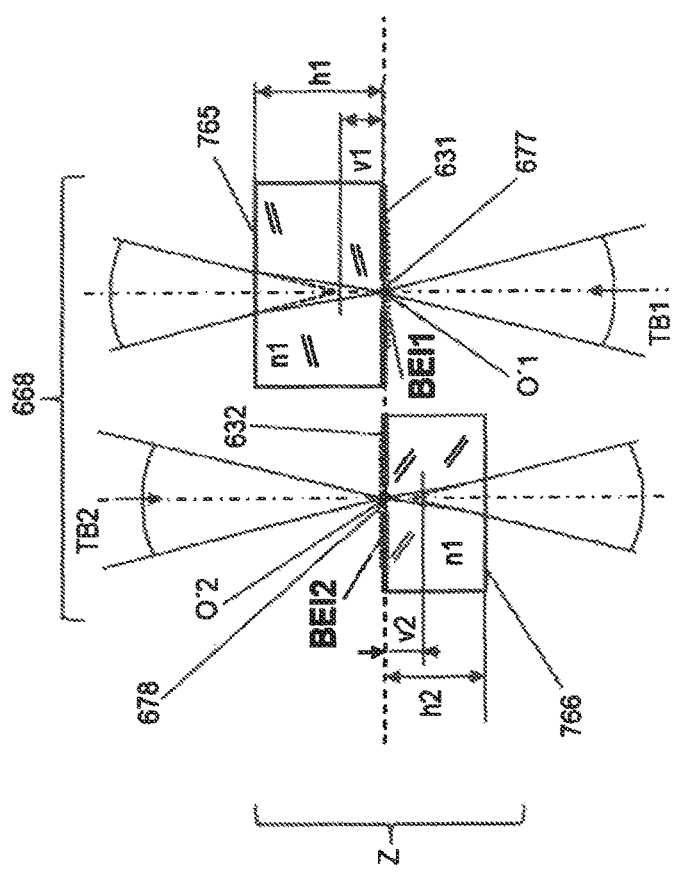
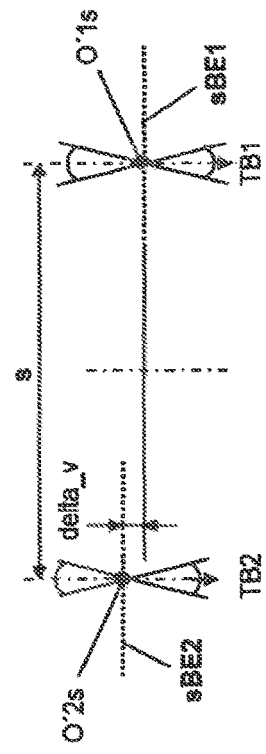
Figure 18a
Figure 18b

METHOD AND FOURIER TRANSFORMATION SPECTROMETER WITH DOUBLE BEAM INTERFEROMETER FOR SINGLE SHOT IMAGING FOURIER SPECTROSCOPY

This U.S. Non-Provisional Patent Application claims priority to European Patent Application No. 20167242.5, filed Mar. 31, 2020, titled "VERFAHREN UND FOURIER-TRANSFORMATIONS-SPEKTROMETER MIT ZWEIS-TRAH L-INFEROMETER ZUR SINGLE-SHOT-IMAGING-FOURIER-SPEKTROSKOPIE," the entire contents of which is incorporated herein by reference.

The invention relates to a Fourier Transformation (FT) spectrometer with double beam interferometer and a method for interferometric measurement, respectively in particular for Single Shot Imaging Fourier Spectroscopy for the purpose of obtaining hyperspectral partial images on the basis of optimized arrangements and positions of field of view discriminators that are at all times arranged within the double beam interferometer.

Single Shot Fourier Transformations Spectroscopy can in particular be used with a comparatively low to moderate spectral resolution. The spectral resolution for this spectroscopy is preferably in the range from about 4 $cm^{-1}$ to about 1000 $cm^{-1}$ (1 $cm^{-1}$=1/cm=reciprocal centimeters, unit of the wave number), wherein the spectral range is preferably addressed from ultraviolet up to the terahertz range of the wavelength of electromagnetic radiation.

A spectral image can in particular be a hyperspectral image, which can generally be available in the form of a data cuboid (x, y, sigma) having the wave number sigma or (x, y, lambda) with the wavelength lambda.

An application for the invention can be the examination of human skin by a doctor, for example for skin cancer screening. A further application can be the examination of at least partially exposed organ tissue during a surgical procedure on living human beings. A further example can be the examination of the interior of the eye, for example an examination of the retina.

A further application can for example be the analysis of foods, in particular when these are moved on an agitated and/or jerking conveyor belt. This also includes the examination of agricultural foods, for example bulk products such as grains and legumes, for which a 100% inspection is required while the conveyor is moving and/or for which at least a high sampling rate is required.

The invention can also be used for fluorescent light analysis of objects and scenes using UV incident light with analysis of the fluorescent light as the information carrier.

The invention can also be applied for measuring objects that exhibit internal movement, such as erupting volcanoes and/or firestorms during forest fires, with a relatively uniform movement of the spectrometer while overflying by helicopter and/or airplane.

The approach according to the invention can also be used to record swirling particles, for example in a flow, spectrally and spatially resolved at least with restrictions, that is to say at least partially imaged.

It is also possible to identify and sort a variety of plastics in household waste and/or in industrial waste based on the spectrum, even while in motion. Based on the spectrum, it is also possible to identify objects made of a variety of plastics when sorting waste on land and/or also objects moving in the waters of an ocean, and to facilitate local sorting as needed.

When taking measurements using the portable spectrometer according to the invention based on a manual scan over the object, objects collected as crime scene evidence, from medicine, hygiene, archaeology, botany, mineral sciences, agriculture can be analyzed hyperspectrally, typically with significantly more than 10 spectral channels per measurement point and spatially resolved. The focus in this case is generally on the spectral information and not on the hyperspectral image of the measured object. In spite of elaborate image post-processing, the hyperspectral image can exhibit certain residual artifacts, which in many cases is regarded as tolerable since for a significant number of metrology tasks, the primary interest is on the spectral information, which should be recorded largely without loss of resolution.

The invention can also be used for close and far range thermal imaging. But it is also possible to use the invention in particular in the terahertz range for airport scanners at security gates for passenger and cargo using the transmitted light method with spectral resolution.

The single shot approach also permits the use of the comparatively cost-effective light sources, which are not very stable over time with regard to their output power, and therefore can exhibit power output fluctuations by as much as 10%. Output power fluctuations represent a considerable problem for serial methods for recording interferograms.

PRIOR ART

The U.S. Pat. No. 4,976,542 by Smith with a cyclical interferometer in the form of the Sagnac interferometer represents a common path arrangement. In FIG. 1, it describes a Sagnac interferometer arrangement with cylinder optics 38 in combination with Fourier optics 36. The cylinder optics 38 render a focused gap opening 24 in length gap direction onto a raster detector, here in the form of a CCD chip. In combination with the Fourier optics 36, the cylinder optics 38 represents an anamorphic imaging stage. In lateral gap direction, the effect of the Fourier optics 36 in combination with the lateral shear generating Sagnac interferometer generates a plurality of spatial interferograms on the CCD chip. The ability to detect spatial interferograms is thus available in single shot mode. However, the gap opening, which in this case then acts as a field of view aperture or as a field of view discriminator, is arranged upstream of the Sagnac interferometer. Due to the comparatively long optical paths, this significantly reduces the opening angle of the beam in the Sagnac interferometer.

The U.S. Pat. No. 5,777,736 by Horton describes an interferometer of type Mach-Zehnder, which features comparatively long optical paths in the interferometer in comparison a Michelson interferometer. As an interferometer of type Mach-Zehnder, it is principally difficult to adjust in comparison to a Michelson-type interferometer, which only features a single beam splitter. This difficulty also exists due to the arrangement of two beam splitters in the Mach-Zehnder interferometer. Accordingly, an interferometer of type Mach-Zehnder exhibits no particularly long long-term stability without significant engineering effort and can only be given a compact design within limits. FIG. 22 of this patent shows a pronounced astigmatism caused by the respectively single path through a tilted beam splitter plate, and which is not compensated in the interferometric beam path. This can result in non-linearities in the spatial interferogram that cause significant difficulties for spectrum calculation or result in highly undesirable artifacts in the calculated spectrum. The resulting full image of the measured object, the scene, or the light source on the detector is overlayed by a single spatial interferogram because a composite lens—described as "exit lens" therein—is arranged as relay optics. A serial interferogram can then only be obtained with a relative motion between the interferometer and the measured object; singe shot mode is not possible because obtaining the interferogram requires uniform motion of the scene, and because the interferogram is at all times created serially and can only be extracted from an image stack for each scanned object point. Document U.S. Pat. No. 5,777, 736 also does not arrange field of view discriminators in the interferometer in the image position.

U.S. Pat. No. 3,684,379A by Girard describes a compact Michelson-Type Interferometer with wedge interferences for field use. The image is created on the two plane mirrors of a Michelson interferometer. But there is no field of view discriminator in the interferometer. Since these are opened beams, the wedge introduced here can generate undesirable wave front aberrations, which can significantly interfere with a spatial interferogram. When analyzing a Fourier transformation, this can result in significant problems and result in unacceptable spectrum errors.

The U.S. Pat. No. 4,523,846 by Breckingridge also describes a very compact Michelson-Type interferometer with a monolithic design, having a non-rectangular arrangement of a plane mirror as interferometer end mirror. This creates the interference of wavefronts tilted toward each other. Here too, the wedge made of refractive material and introduced into the interferometer can generate wavefront aberrations that can significantly interfere with a spatial interferogram. A gap opening for discriminating the field of view that acts as an effective source is in this case located at the input of the interferometer, that is to say outside of the latter. In a position of the instrument, only the spatial interferogram of the entire slot detected in the pupil plane is evidently obtained. There is then evidently no local resolution within the elongated slot. The convex surface with gap aperture at the interferometer input represents a field lens, and is therefore positioned at the image location or approximately in an interim image plane. During a relative motion between the interferometer and the measured object, in this case for example when a satellite flies over a landscape, a one-dimensional hyperspectral image can then be prepared from the sequentially detected spatial interferograms based on the Pushbroom principle. In this case, evidently only a single—in this case stripe-shaped image section—supplies a spatial interferogram at any one point in time. Due to the arrangement of the gap opening at the input of the interferometer, the opening angle for the beam is somewhat limited due to the optical distance from the input to the output of the interferometer. A half opening angle of approximately 10° can nevertheless be achieved. Accordingly, the light yield through the limited opening angle can nevertheless be somewhat restricted. This can result in a non-optimal signal-to-noise ratio in the measured interferogram and therefore also in the calculated spectrum.

The lateral shear can in an optical arrangement be used as a basis for generating interferences of wavefronts tilted toward each other. An entirely classical approach for this is a Michelson interferometer arrangement with two rooftop reflectors in order to generate the required lateral shear. This approach using two rooftop reflectors is generally also used for wavefront analysis and is well known to persons skilled in the art, also refer to Malacara, Optical Shop Testing, John Wiley & Sons, Inc., 1992, p. 140-141, FIG. 4.16 [1] and also to Steel, Interferometry, Cambridge University Press, 1967, p. 83 last paragraph up to top of p. 84 [2].

The approach published by Kelsall in 1959 in Proc. Phys. Society, 73, p. 470, FIG. 1 using two triple reflectors as end reflectors of a Michelson interferometer is also known. The lateral shift of a triple reflector also generates a lateral shear between object and reference wavefronts at the output of a Michelson interferometer. To the best of our knowledge however, use of a triple reflector in the reference beam path of a Michelson interferometer is already disclosed by Twyman and Green, in this regard also refer to U.S. Pat. No. 1,565,533 and to FIG. 6 therein.

In document U.S. Pat. No. 5,131,747, Cerutti-Maori describe a hyperspectral method with an intrinsically rigid Michelson interferometer having a double rooftop arrangement. In this case, the Michelson interferometer generally experiences a very constant movement as it flies over terrain using an aircraft. The image of the terrain is in this case created on the raster detector. The interferogram with image information is formed on the raster detector by wavefronts tilted toward each other. By synchronizing the system components, a constant movement allows each pixel of the raster detector to record a time-series signal of a double-beam interferogram as the latter passes by. But this method does not accommodate the single shot recording of an interferogram. This approach cannot be used to obtain a non-disrupted interferogram when an interferometer moves over the measured object unevenly, or for measured objects with chaotic relative motions, or for turbulent scenes such as bubbling magma.

The document CN 106338342 A by Dou Jianyun and others describes a hyperspectral method with a double rooftop arrangement in a Michelson interferometer for objects scanned using a rotating scanning mirror. The complete image of a static scene is generated on the planar raster detector in the Fourier plane of the optics. The lateral shear introduced by an interferometer causes a spatial interferogram to overlay the image. But this interferogram—which is mapped to an object point—is also only obtained as a time series while flying over the scene. A prerequisite then is that this flyover and also the rotation of the scanning mirror must be very uniform since the resulting interferogram signals are otherwise disrupted. This hyperspectral method is then in no way suited for turbulent scenes, or even for objects with internal chaotic movements, or for handheld devices when operated in a rather unsteady or slightly jittery hand.

FIG. 1 in the industry article "Large field-of-view Fourier transform imaging spectrometer using dual-channel stitching" by Chengmiao Liu and others in OPTICS EXPRESS, Vol. 24, No. 25 dated Dec. 12, 2016, p. 28473-28490, http://dx.doi.org/10.1364/OE.24.028473, [4] shows a Lateral-Shear Interferometer with rooftop reflectors. The spatial interferogram is created in the Fourier plane of a downstream lens with image information. But this system operates on a timeseries to obtain the interferogram signal and is therefore unsuited for single shot applications. In other words: although a spectral metrology method based on the documents U.S. Pat. No. 5,131,747, CN 106338342 A or also [4] will at all times supply a complete image of the measured object or scene, a spatial interferogram is nevertheless obtained based on a timeseries. This then implies a nearly constant relative motion between the interferometer and the measured object, as is generally the case during a calm flyover by a satellite or an aircraft over terrain, in order to permit generating an undisrupted hyperspectral image. Accordingly, due to the chaotic movements in the scene— such as during an automobile crash test—or during nonuniform or even chaotic movements of the interferometer when the instrument is freely held by hand, this approach is rather unsuited for turbulent scenes because the interferogram signals are highly likely disrupted and completely unsuited for typical analysis using a Fourier transformation.

The industry article "Fourier transform spectrometer with a self-scanning photodiode array" by T. Okamoto, S. Kawata and S. Minami in Applied Optics, Vol. 23, No. 2, p. 269-273 dated Jan. 15, 1984 [5] describes a Sagnac Interferometer with a light source arranged in front of the interferometer and a collective lens arranged downstream of said interferometer. No means for field of view discrimination are stated since this is a single channel arrangement wherein a spatial interferogram is detected in the Fourier plane of the collective lens using a photodiode line.

The publication "Global estimates of lunar iron and titanium contents from the Chang' E-1 IIM Data" by Yunzhao Wu and others in the JOURNAL OF GEOPHYSICAL RESEARCH, VOL. 117, E02 from 2012 (doi: 10.1029/2011JE003879) [6] describes an arrangement with a Sagnac Interferometer, wherein an anamorphic imaging stage with a Fourier lens and with cylinder optics is arranged downstream. But the gap opening—that is to say the field of view discriminator—is arranged outside of the Sagnac Interferometer. This significantly reduces the achievable aperture angle.

Although a full image of the measured object can be obtained by using a Sagnac Interferometer with a single shot method, this is not the case for an interferogram for every image point of the measured object since a modulation only occurs in parts of the image. This is the case because full image methods operate on a timeseries basis using a scanner to obtain an interferogram for every image point, so that the interferogram runs through the image during the scan. This is also shown in the U.S. Pat. No. 5,539,517 by Cabib. These full image methods are therefore not suited for chaotically moving measured objects, for a spectrometer subject to unsteady movement, and also not for turbulent scenes because interferogram recordings of chaotically moving measured objects, using spectrometers subject to unsteady movement, or for turbulences within the scene are generally disrupted to such an extent that a spectrum calculation results in significant measurement errors, or such that even extremely high computing effort results in rather unsatisfactory results when calculating spectrums.

FIG. 7 of the U.S. Pat. No. 6,930,781 B2 by Agladze describes a Sagnac Interferometer for the THz range, wherein a focus is formed in the Sagnac Interferometer. But there is no field of view discriminator in the interferometer. Moreover, the detection also does not generate several image points since this is a single channel spectrometer without single shot imaging.

The U.S. Pat. No. 5,541,728 by Dierking describes a Fourier-Transform Spectrometer with a compact cyclical interferometer having four mirrors and a Fourier lens at the output of the interferometer. The optical paths are comparatively long, so that the opening angle in this arrangement is rather limited. A field of view discrimination is not provided since this is a single channel spectrometer without single shot imaging.

In the prior art, it is generally comparatively simple to assemble a shaky image from not equidistant image points, compared to obtaining a low-error spectrum from a disrupted interferogram, in particular when the type and strength of the disruption in the interferometer is largely unknown, which is frequently the case.

Invention

According to an aspect, the task underlying the invention is to provide a robust, efficient Fourier Transformation Spectrometer. In particular, at least a partially hyperspectral imaging of parts of a moving measured object, and/or a turbulent scene, and/or when taking measurements using a spectroscopic instrument, for example using a handheld device, is to be provided in a comparatively short measurement timeframe.

According to an aspect, an FT Spectrometer comprises
a double beam interferometer, comprising
at least one beam splitter unit to split an incident light beam and/or an input beam of a spatially expanded object into a first partial beam and a second partial beam;
at least one first beam deflection unit designed to deflect the first partial beam at least a first and a second time;
at least one second beam deflection unit designed to deflect the second partial beam at least a first and a second time, wherein the beam splitter unit is also designed to spatially at least partially overlay the first partial beam and the second partial beam with a lateral shear, and where the respectively first and second deflection of the first partial beam and the second partial beam generates the lateral shear;
at least one first field of view discriminator unit arranged in the double beam interferometer such that the first partial beam is spatially selected after the splitting and before the second deflection;
at least one second field of view discriminator unit arranged in the double beam interferometer such that the second partial beam is spatially selected after the splitting and before the second deflection;
wherein the FT spectrometer additionally comprises:
at least one lens arranged opposite the beam splitter unit such that the incident light passes the lens at least partially before said light beam is split on the beam splitter unit and the first partial beam and the second partial beam respectively generate a plurality of coherent image points of the spatially expanded object in an image plane between the beam splitter unit and a detector;
the detector having at least one detector field to record a plurality of spatial interferograms on the basis of the spatial overlay of the first partial beam and the second partial beam, which corresponds to at least the partial imaging of the plurality of coherent image points; and
at least one computing unit for the Fourier transformation of the plurality of spatial interferograms to generate a plurality of spectrums, and based thereon, to generate a hyperspectral image of the spatially expanded object.

In particular, the first field of view discriminator unit and the second field of view discriminator unit is arranged such that in the double beam interferometer, the first field of view discriminator unit is optically conjugated in relation to the second field of view discriminator unit.

In particular, the spatially expanded object typically represents a white light source in the sense of a spectrally broad-band light source, and scatters or reflects a part of the light shining thereon at least partially as an incident light beam into the FT spectrometer. However, in special cases, objects can also be examined that are illuminated by a laser light source, for example in the infrared spectrum, without fluorescence occurring. In this case, the light incident in the FT spectrometer is spectrally narrow-banded, provided it essentially originates from the laser light source.

In this case, the FT Spectrometer in particular corresponds to a Single Shot Imaging FT-Spectrometer based on a Michelson-Type Interferometer, a Mach-Zehnder Interferometer, or a cyclical double beam interferometer.

In other words, an FT spectrometer in this case corresponds to an FT spectrometer with at least partially hyperspectral single shot imaging of a measured object and/or an object as a product of a calculation using a computing system and/or a computing unit, using a computing program to obtain spectrums by means of Fourier transformation, preferably a fast Fourier transformation (FFT=fast Fourier transform), and a lens arranged upstream thereof as an imaging system for the measured object, and having a double beam interferometer with the upstream lens arranged upstream thereof, and said lens comprising:

either a beam splitter unit with a beam splitter having a planar beam splitter surface, wherein the beam splitter is used for beam splitting and/or for splitting the incident light beam in the beam splitter plane, which from two partial beams, specifically, a first partial beam that is sent into a first interferometer arm, and a second partial beam that is sent into a second interferometer arm, and also for at least the partial beam unification and/or partial spatial overlay of the partial beams in the beam splitter plane with a lateral shear s between the two partial beams or a beam splitter unit with two beam splitters with respectively planar beam splitter surface, a first beam splitter for beam splitting in the beam splitter plane, thus forming two partial beams, and a second beam splitter for at least partial beam unification with a lateral shear s between the two partial beams, and wherein the double beam interferometer has a reference plane spanned on the input of the double beam interferometer by the normal of the planar beam splitter surface and by the optical axis of the upstream lens, and a raster detector on the output of the double beam interferometer, and wherein the upstream lens—by taking into account the position of the measured object—generates upstream of the double beam interferometer an image or at least a partial image of the measured object in light direction or in direction of propagation of the light, generally downstream the beam splitter, but generally upstream the raster detector, and wherein with the cooperation of an anamorphic imaging stage arranged downstream of the double beam interferometer, a plurality, but at least two, spatial interferograms are formed, and said spatial interferograms are formed on the planar raster detector, and wherein an object point on the measured object is mapped to each spatial interferogram, wherein respectively one field of view discriminator is arranged in an interferometer arm between the beam splitter unit and the output of the double beam interferometer, such that both field of view discriminators are at least approximately optically conjugated toward each other. The invention in particular facilitates the use of beams with a comparatively large opening angle in the double beam interferometer based on comparatively short paths in the two interferometer arms. The optical setup provides the opportunity for significant miniaturization of the interferometer.

Based on an aspect, an NFT spectrometer comprises the following:

a double beam interferometer, comprising
at least one beam splitter unit to split an incident light beam and/or an input beam of a spatially expanded object into a first partial beam and a second partial beam;

at least one first beam deflection unit designed to deflect the first partial beam at least a first and a second time, wherein
the first beam deflection unit is designed to also deflect the second partial beam at least a first and a second time corresponding to a beam projection in a cyclical double beam interferometer; or
the double beam interferometer comprises a second beam deflection unit designed to deflect the second partial beam at least a first and a second time, wherein the beam splitter unit is also designed to spatially at least partially overlay the first partial beam and the second partial beam with a lateral shear, and where the respectively first and second deflection of the first partial beam and the second partial beam generates the lateral shear;
at least one first field of view discriminator unit arranged in the double beam interferometer such that the first partial beam is spatially selected after the splitting and before the second deflection;
at least one second field of view discriminator unit arranged in the double beam interferometer such that the second partial beam is spatially selected after the splitting and before the second deflection;

wherein the FT spectrometer additionally comprises:
at least one lens arranged opposite the beam splitter unit such that the incident light passes the lens at least partially before said light beam is split on the beam splitter unit and the first partial beam and the second partial beam respectively generate a plurality of coherent image points of the spatially expanded object in an image plane between the beam splitter unit and a detector;
the detector having at least one detector field to record a plurality of spatial interferograms on the basis of the spatial overlay of the first partial beam and the second partial beam, which corresponds to at least the partial imaging of the plurality of coherent image points; and
at least one computing unit for the Fourier transformation of the plurality of spatial interferograms to generate a plurality of spectra, and based thereon, to generate a hyperspectral image of the spatially expanded object.

This combined embodiment comprises two alternative embodiments: firstly, a cyclical, and secondly, a non-cyclical double beam interferometer, such as a Michelson-Type or a Mach-Zehnder Interferometer.

A cyclical double beam interferometer only comprises one beam deflection unit. This beam deflection unit, called a "first beam deflection unit", essentially comprises two reflectors, in particular two mirrors or two mirror prisms that each deflect or reflect the first and the second partial beam once. This means that the first beam deflection unit in particular comprises two deflecting or reflecting surfaces, such as two mirror surfaces. Each of the two reflecting surfaces is designed to respectively reflect the first partial beam and the second partial beam once, so that both partial beams only use a single combination of both mirrors.

But a noncyclical interferometer, such as the Michelson-Type or the Mach-Zehnder Interferometer also has a second beam deflection unit in addition to the first beam deflection unit. Both beam deflection units in particular each have two reflecting surfaces. Moreover, the beam deflection units are not split by the first and the second partial beam. Instead, the first beam deflection unit is designed to reflect the first partial beam twice, and the second beam deflection unit is designed to reflect the second partial beam twice. The beam deflection units can each have a double mirror arrangement, such as a rooftop reflector or a double mirror prism.

In particular during signal recording, there are essentially also no moving, and instead essentially (inherently) rigid components in the entire spectrometer. This has the advantage that the FT spectrometer can exhibit relatively high ruggedness.

There is the option to use an upstream lens that renders the image of the measured object directly into a double beam interferometer.

In particular, there are advantages for use of the method and the double beam interferometer for low-speed lenses, in particular in rough environments with regard to the achievable signal-to-noise ratio and ruggedness in relation to shaking and/or vibrations. In particular, this is caused by the invariance of the angle for a beam deflection in the interferometer. This is preferably the case with largely miniaturized optical components, which are preferably formed as tilt-invariant, monolithic components with respectively two mirror surfaces with high mechanical stability.

By concurrently running a comparatively simple monitor camera, assembling even slightly shaky image series is comparatively simple in comparison to obtaining a low-error spectrum from a disrupted interferogram. A person skilled in the art can comparatively easily monitor the measured object and/or the scene with a motion and acceleration sensor arrangement to obtain useful supplemental information that is helpful for generating a hyperspectral image.

An advantage is that individually discriminated regions of the image of the object to be detected can be used to simultaneously generate at least two spatial interferograms. Preferably, a larger number of spatial interferograms can be generated that at least partially contain the information about the searched spectrum, so that two and/or more complete spatial interferograms can be captured in a single recording. This approach in particular facilitates single shot mode.

For a single shot method, the detector—in this case generally a raster matrix detector in the FT spectrometer—respectively records a single image after an external or internal digital start command for the matrix detector. Using double beam interferometers, a plurality of spatial interferograms arranged next to each other are generated on the matrix detector. For typical matrix detectors, the number of such spatial interferograms is in the order of magnitude from one-hundred to one-thousand. The spatial interferograms on a camera image generally respectively belong to a linear partial region of the measured object. This at least represents a selected partial region of the measured object by means of spatial discrimination. Fast Fourier Transformation (FFT) is employed to numerically compute the spatial interferograms into spectrums, where appropriate, also only after interim storage. The recording time—or the time window for the single shot—is in this case generally determined by the integration time (more generally: image recording time) of the raster matrix detector, which depending on the detector type and light conditions can extend from the single-digit microsecond range up to the three-digit millisecond range. In an extreme case, the integration time can also extend up to the single-digit second range at extremely low light energy and comparatively very low dynamics in the measured object. But for flash illumination or pulsed illumination of the measured object—synchronization implied—the flash or pulse duration determines the time window for the single shot and analogously also the opening time of a controlled aperture, provided that the latter are respectively shorter than the aforementioned integration time of the matrix detector.

Several recordings of the raster detector array in the fastest possible sequence, for example with a recording frequency of 60 Hz, then result in a plurality of adjacent, generally linear partial regions of a measured object, so that a spectrum can be incrementally generated by means of relative motion for each resolvable surface increment of a surface-based measured object, thus resulting in a hyperspectral image. The achievable lateral resolution in the hyperspectral image is in this case—as known—determined by the parameters of the optical components in the imaging system and potentially also from the raster constant of the (raster) matrix detector of the FT spectrometer. Late-model high-speed matrix detectors also permit integration times (image recording times) in the range of 10 microseconds, possibly also less than that.

Moreover, light can in particular be captured with a comparatively large solid angle from a location of the measured object and/or the scene, and can be detected as interference light using a double beam interferometer. In particular, this is intended to permit use of a downstream lens at the output to capture said interference light with the largest possible aperture angle alpha in order to use the largest possible share of the captured light energy for detection. This can preferably also permit comparatively short integration times of raster detectors, so that single shot measurements can also be made of moving measured objects and of turbulent scenes.

When actively illuminated with a light source, the energy of the latter can potentially be put to optimized use. The entire light of the latter can for example be directed onto a narrow object field. Based on the aspect of energy use, a disadvantage can be avoided when only a small, narrow field and/or an object section is recorded with a single shot measurement.

In order to effect high ruggedness, in particular by reducing the problem of a very undesirable and/or uncontrolled and/or erroneous adjustment, in particular an out-of-adjustment of the interferometer, the interferometer can in particular exist in miniaturized form. In particular, the beam splitters and/or the end reflectors of the interferometer can be miniaturized, for example also because foil beam splitters and/or pellicle beam splitters can be used, which can be sensitive to vibration in large formats. Moreover, particularly short paths can be implemented in the arms of the interferometer. Additionally, the two partial beams that leave the interferometer can potentially be free of an astigmatism, or can have an at least approximately equivalent astigmatism.

If needed, an adaptability to the measured object and also a pattern-based scan of the measured object can be facilitated. Preferably, this can also facilitate wide-ranging flexibility for the selection of the lateral resolution in the image of the measured object.

That lateral shear ("Lateral-Shear") of the partial beam generated by the double reflection with the beam deflection unit in the sense of a lateral shear parallel to the reference plane is in this case generally and essentially constant, assuming the mechanically rugged construction of the double beam interferometer. The lateral shear between the partial beams influences the formed interferogram. Because this lateral shear is generally and essentially constant, the interferometer is essentially insensitive to vibrations. This applies when the beam deflection unit itself essentially exhibits no movement with lateral component based on a rugged construction of the double beam interferometer, or the mirrors of the beam deflection unit exhibit no intrinsic movement with a lateral component.

A directional change of the partial beam is also created after reflection with the beam deflection unit. The latter is unchangeable with respect to the angle of this directional change of the partial beam even when the angular position of the beam deflection unit is changed, provided the latter is itself constructed sufficiently rigid—at least when the latter is tilted about a tilt axis that is vertical in relation to a reference plane. The result is a "tilt-invariant double beam interferometer" that ideally does not come out of adjustment even due to shocks and vibrations, essentially in relation to the angles of the partial beams at the output of the double beam interferometer. The ideal case can in particular be approximated for a noncyclical double beam interferometer, that is to say when the beam deflection unit is respectively constructed mechanically very rigid, and therefore has a compact construction, for example in the form of the smallest possible monolith.

Due to the single shot recordings, the double beam interferometer is also relatively insensitive to disruptions that are slow in comparison to the image generation. As a result, in particular also chaotically moving objects can be measured. Alternatively, nonmoving objects can also be measured while the spectrometer is moved chaotically.

Additionally, the double beam interferometer constructed in this way can in various embodiments have the following advantages versus conventional double beam interferometers:

The spectrometer according to the invention is comparatively rugged, even for larger measurement spots. Only rigid components are installed in the spectrometer. As a result, the spectrometer additionally exhibits relatively high long-term stability.

The design is also readily miniaturized. Equipment that can be guided by hand over the object surface can then also be realized.

Due to the transmitted light coefficient advantage of Fourier spectroscopy in comparison to dispersive spectroscopy, in particular also less brightly radiating objects can be recorded, or measurements can be obtained faster.

The described construction in particular has the advantage that a better signal-to-noise ratio is obtained for low-light objects under unsettled conditions.

In particular, the beam splitter unit has a single beam splitter in order to split the incident light beam of a spatially expanded object into the first partial beam and the second partial beam; and to at least partially spatially overlay the first partial beam and the second partial beam.

In particular, the first field of view discriminator unit and the second field of view discriminator unit are arranged in relation to each other such that at least an approximate optical conjugation is obtained between the first field of view discriminator unit and the second field of view discriminator unit.

The double beam interferometer in particular corresponds to a Michelson-Type Interferometer, comprising the second beam deflection unit, wherein the first beam deflection unit has a double mirror periscope reflector that hereinafter comprises a first mirror designed to reflect the first partial beam at least a first time; and a second mirror that is arranged at an angle $\Theta_1$ in relation to the first mirror, and that is designed to reflect the first partial beam at least a second time; and/or the second beam deflection unit has a further double mirror periscope reflector that hereinafter comprises a first mirror designed to reflect the second partial beam at least a first time; and a second mirror that is arranged at an angle $\Theta_2$ in relation to the first mirror, and that is designed to reflect the second partial beam at least a second time.

The angles $\Theta_1$ and $\Theta_2$ of the two double-mirror periscope reflectors are made equal at least approximately.

The double beam interferometer alternatively corresponds to a Michelson-Type Interferometer, comprising the second beam deflection unit, wherein the first beam deflection unit comprises a triple-mirror periscope reflector, preferably also known as a corner cube arrangement, that hereinafter comprises a first mirror designed to reflect the first partial beam at least a first time; and a second mirror that is arranged at an angle $\Theta_1$ in relation to the first mirror, and that is designed to reflect the first partial beam at least a second time; and a third mirror that is arranged at an angle $\Theta_{a1}$ in relation to the first mirror and at an angle $\Theta_{b1}$ in relation to the second mirror, and that is designed to reflect the first partial beam at least a third time; and/or the second beam deflection unit comprises a further triple-mirror periscope reflector essentially of equal construction to the first triple-mirror periscope reflector, preferably also known as a corner cube arrangement, that hereinafter comprises a first mirror designed to reflect the second partial beam at least a first time; and a second mirror that is arranged at an angle $\Theta_2$ in relation to the first mirror, and that is designed to reflect the second partial beam at least a second time; and a third mirror that is arranged at an angle $\Theta_{a2}$ in relation to the first mirror and at an angle $\Theta_{b2}$ in relation to the second mirror, and that is designed to reflect the first partial beam at least a third time.

The FT spectrometer in particular is a double beam interferometer, in particular a Michelson-Type Interferometer, wherein the first field of view discriminator unit has an opening designed to spatially select the first partial beam after the first reflection using the first mirror of the first beam deflection unit and prior to the second reflection using the second mirror of the first beam deflection unit; and/or the second field of view discriminator unit has a further opening designed to spatially select the second partial beam after the first reflection using the first mirror of the second beam deflection unit and prior to the second reflection using the second mirror of the second beam deflection unit.

The double beam interferometer in the FT spectrometer alternatively corresponds to a Michelson-Type Interferometer, comprising the second beam deflection unit, wherein the first beam deflection unit further comprises a first prism having a first reflection surface designed to reflect the first partial beam at least a first time; and a second reflection surface designed to reflect the first partial beam at least a second time; and/or the second beam deflection unit further comprises a second prism having a first reflection surface designed to reflect the second partial beam at least a first time; and a second reflection surface designed to reflect the first partial beam at least a second time.

The FT spectrometer in particular is a double beam interferometer, in particular a Michelson-Type Interferometer, wherein
- the first field of view discriminator unit has an opening designed to spatially select the first partial beam after the splitting of the incident light beam using the beam splitter unit and prior to the first reflection of the first partial beam using the first reflection surface of the first prism; and/or
- the second field of view discriminator unit has an opening designed to spatially select the second partial beam after the splitting of the incident light beam using the beam splitter unit and prior to the first reflection off of the second partial beam using the first reflection surface of the second prism.

In particular, the relevant Fourier Transformation Spectrometers include those that have a comparatively low to moderate spectral resolution delta sigma, preferably in the range for delta sigma between approximately 1 $cm^{-1}$ and approximately 5000 $cm^{-1}$, in particular between approximately 3 $cm^{-1}$ and approximately 3000 $cm^{-1}$, and preferably between approximately 4 $cm^{-1}$ and approximately 1000 $cm^{-1}$. The invention can in particular be used in the visual spectral range (VIS), in particular between approximately 380 nm and 750 nm, in the near infrared range (NIR), in particular between approximately 0.78 μm and 3 μm, and in the midinfrared range (MIR) in particular between approximately 3 μm and 50 μm, and in the far infrared range (FIR) in particular between approximately 50 μm and 1 mm, in the terahertz range and/or also in combined spectral ranges. The invention can additionally or alternatively also be used in the UV range, in particular in the near UV-A range, in particular between approximately 315 nm and 380 nm, in the UV-B range, in particular between approximately 280 nm and 315 nm and in the UV-C range, in particular between approximately 100 nm and 280 nm.

Largely unfalsified spectrums need to be obtained of moving objects and/or also in the presence of vibrations and/or turbulences in a scene to be measured, and therefore for example in field use; nevertheless, certain errors need to be permitted or accepted when scanning the measured object—that is to say when generating a hyperspectral image in the form of a known data cuboid (x, y, sigma), with sigma as the wave number or (x, y, lambda) with lambda as the wavelength. The spectral information is preferably obtained in single shot mode. As a result, said information is less error-prone than the local information of the measured object, which is obtained in series.

According to the invention, the measured object is essentially or at least partially located outside of the double beam interferometer and is generally positioned upstream of the latter or locally in front thereof. However, the measured object can principally also be arranged downstream of the interferometer or physically thereafter.

It is firstly stated for the record that this in particular also refers to hyperspectral single shot imaging when essentially only two or relatively few spatial interferograms can be obtained of a measured object in single shot mode to computationally obtain a hyperspectral partial image. However, generally at least approximately one-hundred spatial interferograms are to be typically obtained with the invention in single shot mode, and therefore essentially concurrently. It is also possible to capture approximately 20 to approximately 5000, in particular approximately 30 to approximately 1000, preferably however approximately 50 to approximately 150 interferograms. These spatial interferograms can for example essentially originate from a line, a narrow area and/or from a raster, respectively on the measured object.

Spatial interferograms for Fourier spectroscopy can be generated or obtained using a lateral shear between object and reference wave fronts at the output of a Michelson-Type Interferometer by using a lens with positive refractive power arranged downstream of the Michelson-Type Interferometer, and can then be captured or recorded using a downstream raster detector. Using a numerically configured fast Fourier Transformation (FFT), the spectrum can be calculated from the spatial interferogram.

In comparison to methods working serially with a spatial interferogram in the full image, the present invention can either generate a one-dimensionally limited measurement field and/or also a two-dimensional measurement field in a relatively coarse raster of measurement locations. However, this potential property is somewhat diminished in significance when the measured object is actively illuminated with an artificial light source, and the available light energy P_total from this light source is concentrated onto for example an essentially stripe-shaped surface instead of for example onto a circular surface, resulting in a significantly higher illumination strength. In this case, the illumination strength in particular on the smaller stripe-shaped surface— that is to say the measurement field—is correspondingly higher, and the integration time of a raster detector can be correspondingly reduced. Accordingly, an advantage of the invention is that the available light energy is used effectively, in particular when illuminating with a light field geometrically matched to the measurement field of the measured object. A particular advantage is given for the case when an essentially nonbiological measured object is at least for a short duration exposed to a very high illumination strength when illuminated, for example in the form of a narrow light stripe on the measured object. The measured object can in particular be illuminated with a cross-section converter that is essentially shaped into an elongated, narrow area.

The first field of view discriminator unit preferably has an opening designed to spatially select the first partial beam after splitting the incident light beam using the beam splitter unit and after the second reflection of the first partial beam using the second reflection surface of the first prism; and/or the second field of view discriminator unit has an opening designed to spatially select the second partial beam after splitting the incident light beam using the beam splitter unit and after the second reflection of the second partial beam using the first reflection surface of the second prism.

The first field of view discriminator unit preferably has an opening designed to spatially select the first partial beam after splitting the incident light beam using the beam splitter unit and prior to the second reflection of the first partial beam using the second reflection surface of the first prism; and/or the second field of view discriminator unit has an opening designed to spatially select the second partial beam after splitting the incident light beam using the beam splitter unit and prior to the second reflection of the second partial beam using the first reflection surface of the second prism.

The double beam interferometer in the FT Spectrometer preferably corresponds to a Mach-Zehnder Interferometer, comprising the second beam deflection unit, and wherein the beam splitter unit further comprises:
- a first single beam splitter for splitting the incident light beam into the first partial beam and the second partial beam; and a second single beam splitter to spatially overlay the first partial beam and the second partial beam.

The FT spectrometer in particular is a double beam interferometer, in particular a Mach-Zehnder Interferometer, wherein
   the first beam deflection unit further comprises
      a first mirror designed to reflect the first partial beam at least a first time; and
      a second mirror that is arranged at an angle $\Theta_3$ in relation to the first mirror, and that is designed to reflect the first partial beam at least a second time; and/or
   the second beam deflection unit further comprises
      a first mirror designed to reflect the second partial beam at least a first time; and
      a second mirror that is arranged at an angle $\Theta_4$ in relation to the first mirror, and that is designed to reflect the second partial beam at least a second time.

The FT spectrometer in particular is a double beam interferometer, in particular a Mach-Zehnder Interferometer, wherein
   the first field of view discriminator unit has an opening designed to spatially select the first partial beam after the first reflection using the first mirror of the first beam deflection unit and prior to the second reflection using the second mirror of the first beam deflection unit; and/or
   the second field of view discriminator unit has a further opening designed to spatially select the second partial beam after the first reflection using the first mirror of the second beam deflection unit and prior to the second reflection using the second mirror of the second beam deflection unit.

In other words, the double beam interferometer can be formed with two interferometer arms as a noncyclical interferometer, for example as a Michelson-Type Interferometer or as a Mach-Zehnder Interferometer, and respectively one double mirror periscope reflector can be arranged in each interferometer arm, or respectively one triple mirror reflector or respectively one triple mirror prism can be at least approximately arranged in corner cube form in every interferometer arm, wherein the difference of the mirrors or mirror surfaces in the two interferometer arms is in particular zero and the former are arranged in a position between one third and two thirds of the optical distance OPD in the beam path between the beam splitting and beam reunification.

The advantage of a noncyclical double beam interferometer, that is to say a Michelson-Type Interferometer and/or a Mach-Zehnder Interferometer, with four mirrors is that the optical distance difference and the lateral shear can be adjusted independently of each other. Alternatively, at least one triple mirror reflector and/or respectively one triple mirror prism is/are at least approximately arranged in corner cube form in each interferometer arm. In the noncyclical double beam interferometer, these reflectors preferably are of equal construction. Reflectors can alternatively also not be of equal construction. For example, a mirror-based reflector can be arranged in one arm, and a prism-based reflector can be arranged in the other arm.

The FT spectrometer in particular is a double beam interferometer, in particular a cyclical double beam interferometer, wherein
   the first beam deflection unit is designed to also deflect the second partial beam at least a first and a second time, the first field of view discriminator unit has an opening designed to spatially select the first partial beam after the first deflection and prior to the second deflection; and
   the second field of view discriminator unit has a further opening designed to spatially select the second partial beam after the first deflection and prior to the second deflection.

In particular, this is a double beam interferometer, in particular a cyclical double beam interferometer, wherein the beam deflection unit has a periscope arrangement that hereinafter comprises
   a first mirror designed to reflect the first partial beam at least a first time, and to reflect the second partial beam at least a second time; and
   a second mirror that is arranged at an angle epsilon in relation to the first mirror, and that is designed to reflect the second partial beam at least a first time and to reflect the first partial beam at least a second time.

In other words, the double beam interferometer can be configured as a cyclical double beam interferometer and have two plane mirrors that form a periscope arrangement on which the two plane mirrors are spaced at unequal distances from the beam splitter plane that contains the horizontal beam splitting surface, and wherein the two plane mirrors are at least approximately aligned vertically in relation to the reference plane.

The invention in particular relates to a double beam interferometer, in particular a cyclical double beam interferometer, wherein
   the beam deflection unit has a double-prism arrangement that hereinafter comprises
      a first prism having at least one reflection surface designed to reflect the first partial beam at least a first time, and to reflect the second partial beam at least a second time; and
      a second prism having at least one reflection surface designed to reflect the second partial beam at least a first time, and to reflect the first partial beam at least a second time.

In other words, the double beam interferometer is formed as a cyclical double beam interferometer, in particular having two planar mirror surfaces of which respectively exactly one is arranged on one mirror prism each, in particular made of refractive material, thus creating a double mirror prism arrangement that is formed with respectively exactly two mirror prisms, wherein either the two plane mirrors that are formed as a periscope arrangement or the two planar mirror surfaces of the double mirror prism arrangement of the beam splitter plane ET that contains the beam splitter surface are spaced at a predetermined unequal distance and are arranged approximately vertically to the reference plane, and wherein an angle epsilon having double the value of the half-angle psi is created between the two plane mirrors or planar mirror surfaces and said angle epsilon is shown in the reference plane as two straight lines projecting from the plane mirrors or from the planar mirror surfaces and the half-angle psi is formed with a value greater than 20 degrees and with a value less than 30 degrees, and wherein a first image plane and a second image plane exist in the double beam interferometer that are each determined by the upstream lens, the location of the measured object and the double beam interferometer, and wherein a first field of view discriminator is mapped to a first image plane and a second field of view discriminator is mapped to the second image plane in the double beam interferometer, and wherein said field of view discriminators are each formed with at least one non-discriminating area in transmission or reflection and said two field of view discriminators are arranged in the double beam interferometer such that an optical conjugation exists at least approximately between said field of view discriminators.

The invention in particular relates to a double beam interferometer, in particular a cyclical double beam interferometer, wherein
  the first field of view discriminator unit has an opening designed to spatially select the first partial beam after the first reflection using the first mirror or the reflection surface of the first prism and prior to the second reflection using the second mirror of the reflection surface of the second prism; and
  the second field of view discriminator unit has a further opening designed to spatially select the second partial beam after the first reflection using the second mirror or the reflection surface of the second prism and prior to the second reflection using the first mirror or the reflection surface of the first prism.

In other words, the construction of an FT spectrometer can consist of a double beam interferometer that can be cyclical or noncyclical and that can additionally comprise two of the following elements: double-mirror periscope reflector, plane mirror, mirror prism, and mirror surface.

The combination of the aforementioned elements is in this case generally selected such that a lateral shear is generated on one of two partial beams. The lateral shear is in particular the value by which the partial beam is shifted laterally after the reflection.

Both partial beams are subsequently guided essentially in parallel in the double beam interferometer. And finally, using an anamorphic lens, both light beams can be deflected toward each other and an interference between the two can be caused on the detector array.

For each of the measurement points on the line under examination, an associated interferogram can exist on the detector array from which the associated spectrum can then be calculated using Fourier transformation.

The field of view discriminators used in the interior of the double beam interferometer in particular ensure that the light from the individual measurement points remains separated from each other.

The application in particular makes use of the principle of white light interferometry (WLI). This method is used to determine the height profile of an object with a resolution of up to approximately 1 nm. For this purpose, in particular the intensity maximum is determined, and the height of the associated object point is calculated therefrom.

A complete height profile of the object can be generated in this manner by scanning the object in x and y directions.

The application according to the invention in particular determines the spectral characteristics of the object point from the measured interferogram. The extent of the interferogram on the detector is limited by using white light (or light with a short coherence length, or with long distances-and/or runtime differences). This in particular results in a larger signal-to-noise ratio. The resolution of the spectrometer according to the invention is in particular a function of the number of pixels on the detector array. The spectrums calculated therefrom only have a low to moderate spectral resolution that is sufficient for many metrology tasks. The spectral characteristics of an object point can be determined by a single recording, which is why this is also referred to as single shot spectroscopy.

In all double beam interferometer types, every field of view discriminator can be mapped to a double mirror periscope reflector or to a triple mirror reflector in the form of a corner cube.

When a measured object is rendered in a double beam interferometer, in particular at least one image plane can be at least approximately brought to at least partial coincidence with respectively one field of view discriminator.

In particular, at least one of the two field of view discriminators in a double beam interferometer can be formed as a gap.

In particular, at least one of the two field of view discriminators in a double beam interferometer can be formed as a computer-controlled, spatial light modulator.

Optionally, at least one of the two field of view discriminators, in particular in a Michelson-Type Interferometer, can be formed and arranged as a gap aperture, wherein preferably respectively exactly one gap aperture is positioned in each arm of the Michelson-Type Interferometer.

In particular in a Michelson-Type Interferometer, each gap aperture can optionally be arranged in optical conjugation to the apparent end mirror surface of the respective interferometer arm.

In particular in a Michelson-Type Interferometer, the field of view discriminators can optionally each be arranged in a position at least approximately at half the distance of the optical distance in the beam path between the beam splitting and beam reunification.

In particular in a Michelson-Type Interferometer, each double mirror periscope reflector can optionally be formed with a beam deflection of at least approximately 180 degrees.

In particular in a Michelson-Type Interferometer, a field of view discriminator can optionally be formed with a liquid crystal display.

The field of view discriminators can optionally be arranged in particular in a Mach-Zehnder Interferometer, and in this case, respectively exactly one gap aperture can be positioned as a field of view discriminator in each arm of the Mach-Zehnder Interferometer (604).

In particular in a double beam interferometer, the field of view discriminators can optionally each be arranged in a position at least approximately at half the distance of the optical distance in the beam path between the beam splitting and beam reunification.

In particular in a double beam interferometer, the double mirror periscope reflectors can optionally be formed with a beam deflection between 45 degrees and 135 degrees.

In particular in a double beam interferometer, at least one field of view discriminator can be optionally formed as a digital micro-mirror array.

In particular in a cyclical double beam interferometer with two plane mirrors or two planar mirror surfaces, a gap opening can be optionally arranged in the two opposingly revolving partial beams of the double beam interferometer in respectively one gap aperture as a field of view discriminator in an image plane of the measured object.

In particular in a cyclical double beam interferometer with two plane mirrors or two planar mirror surfaces, a double-gap aperture with respectively two gap openings can be optionally arranged in the two opposingly revolving partial beams of the double beam interferometer in a plane vertical to the main beams of the partial beams, the double-gap aperture representing the common image plane.

In particular in a cyclical double beam interferometer with two plane mirrors, a computer-controllable, transmissive liquid crystal display can optionally be arranged between said plane mirrors or planar mirror surfaces with at least two pass-through areas.

Optionally, two gap-shaped pass-through areas can be formed in particular in the transmissive liquid crystal display.

In particular in a cyclical double beam interferometer, the beam splitter plane and the intersection SP of the straight lines g1 and g2 can be optionally separated from each other by the distance d_ST, and this distance d_ST can be at least about ten wavelengths of the largest wavelength in the spectrum of the detected light.

At least one mirrored staircase with two mirrors can be optionally arranged in particular in the region Z, where no spatial overlap occurs between the two partial beams.

In particular in a cyclical double beam interferometer, two mirrored staircases with two mirrors can be optionally arranged in particular in the region Z, where no spatial overlap occurs between the two partial beams.

In particular in a cyclical double beam interferometer, the two mirrors of a first mirrored staircase can be optionally formed as plane mirrors, and the two mirrors of a second mirrored staircase can be formed as plane mirrors.

Optionally, in particular in a cyclical double beam interferometer, in region Z where no spatial overlap occurs between the two partial beams, the two plane mirrors can be respectively arranged in parallel to each other on the first miniaturized mirrored staircase, and the two plane mirrors can be respectively arranged in parallel to each other on the second miniaturized mirrored staircase.

Optionally, the two parallel plane mirrors of a first mirrored staircase and the parallel plane mirrors of a second mirrored staircase can in a cyclical double beam interferometer preferably have a slightly different distance dm_1 and dm_2.

Optionally, in particular in a cyclical double beam interferometer, in region Z where no spatial overlap occurs between the two partial beams, the first mirrored staircase and the second mirrored staircase can be combined into a double mirrored staircase using a center web, and the two inner plane mirrors can be respectively arranged in parallel to each other on a side of the center web of the double mirrored staircase.

In particular in a cyclical double beam interferometer, a field of view discriminator can optionally be mapped to at least one mirrored staircase.

Optionally, the field of view discriminator can either be formed as a gap aperture, as a narrow pinhole array, or as a raster, computer-controllable, micromechanical pinhole array.

A field of view discriminator can optionally be formed as a narrow plane mirror that forms one of the two plane mirrors of a mirrored staircase.

A field of view discriminator can optionally be formed as a computer-controllable digital micro-mirror array in at least one mirrored staircase.

In particular in a cyclical double beam interferometer, a comparatively small angle tau_1 from up to 10 degrees between the two plane mirrors of a first mirrored staircase, and also a comparatively small angle from up to 10 degrees can optionally exist between the two plane mirrors of a second mirrored staircase, and the values of the angles tau_1, tau_2 in both mirrored staircases can be at least approximately made the same, and the angle kappa between the main beam HTB1a that projects from the first mirrored staircase and the main beam HTB2a that projects from the second mirrored staircase (83) can be formed as less than 180 degrees, but not less than 140 degrees, on the side facing the interferometer.

In particular in a cyclical double beam interferometer, at least one miniaturized mirrored staircase can be optionally arranged in the region Z, on which at least one mirror is formed with a weak curvature.

For Fourier transformation spectroscopy, in particular in a cyclical double beam interferometer, two mirror prisms of equal construction and respectively made of the same refractive material can optionally be arranged in the revolving beam path, and the mirror prisms can each be formed with only a single mirror surface, and said mirror prisms can each have the same acute angle psi between the mirror surface and respectively one non-reflective surface, and two field of view discriminators can be positioned between these two mirror prisms of equal construction.

For Fourier transformation spectroscopy, in particular in a cyclical double beam interferometer, two mirror prisms with equal angles and respectively made of the same refractive material can optionally be arranged in the revolving beam path, and the mirror prisms can each be formed with only a single mirror surface, and said mirror prisms can each have the same acute angle psi between the mirror surface and respectively one non-reflective surface, and two field of view discriminators can be positioned between these two mirror prisms with equal angles.

Optionally, in particular in a cyclical double beam interferometer, two mirror prisms made of the same refractive material and that each have only a single mirror surface can be arranged, and the two mirror prisms can each have a first acute angle psi, a second acute angle 2 psi, and a third angle with the value 180 degrees minus 3 psi, and thus at least three angles on the two mirror prism correspond to each other, and additionally a plane parallel plate made of refractive material can be arranged between these two mirror prisms, and the plane parallel plate can be fixed between these two mirror prism using two optically transparent cement layers, and either a beam splitter layer can be applied on the side of the plane parallel plate that faces the mirror prism, or the beam splitter layer can alternatively be applied on the mirror prism on the side of the plane parallel plate facing the plane parallel plate.

The invention can in particular relate to a Fourier transformation spectrometer, that is to say with at least partial hyperspectral single shot imaging of a measured object as a product of a calculation using a computer system to obtain spectrums by means of Fourier transformation, and with an upstream lens as an imaging system for the measured object and with a cyclical double beam interferometer positioned downstream of the upstream lens, the lens comprising:

a beam splitter with a planar beam splitter surface and wherein the beam splitter is used for both beam splitting in the beam splitter plane, thus forming two partial beams, and also for at least partial beam unification in the beam splitter plane using a lateral shear s between the two partial beams and a reference plane exists on the cyclical double beam interferometer, wherein the reference plane is spanned by the normal of the planar beam splitter surface and by the optical axis of the upstream lens on the input of the interferometer, and a raster detector at the output of the cyclical double beam interferometer and the upstream lens arranged upstream of the cyclical double beam interferometer—taking into account the position of the measured object—generates an image or at least a partial image of the measured object in light direction, generally downstream of the beam splitter, but generally upstream of the raster detector and with the involvement of an anamorphic imaging unit arranged downstream of the cyclical double beam interferometer generates a plurality, but at least two, spatial interferograms, wherein these spatial interferograms are rendered on the two-dimensional receiver raster receiver, and wherein an object point on the measured object is mapped to every spatial interferogram, wherein the cyclical double beam interferometer is formed with two plane mirrors that form a periscope arrangement, wherein the two plane mirrors are equidistant from the beam splitter plane ET that contains the planar beam splitter surface and are at least approximately arranged vertically in relation to the reference plane and an angle epsilon with double the value of the half angle psi exists between the two plane mirrors that form the periscope arrangement and said angle epsilon is represented by two straight lines projecting from the plane mirrors or from the planar mirror surfaces in the reference plane, and the half angle line of the angle epsilon lies in the beam splitter plane ET and the half angle psi is formed with a value greater than 20 degrees and with a value less than 30 degrees and the symmetrically constructed cyclical double beam interferometer has a first image plane and a second image plane that are each determined by the upstream lens, the location of the measured object, and the double beam interferometer, and the first image plane is mapped to a first field of view discriminator, and the second image plane is mapped to a second field of view discriminator in the double beam interferometer and said two field of view discriminators are arranged in the symmetrically constructed cyclical double beam interferometer such that an optical conjugation exists at least approximately between these field of view discriminators, and in the cyclical double-beam interferometer, one optical functional assembly each to generate a beam shear is mapped to one field of view discriminator each between the plane mirrors in the revolving beam path, which form a periscope arrangement, and the optical functional assemblies generate a beam shear in respectively opposing direction, thus generating a lateral shear s at the output of the cyclical double beam interferometer.

In particular, the optical functional assemblies can be formed as two mirrored staircases in air or as two at least rhomboid-like mirror prisms to generate a beam shear in a cyclical double beam interferometer.

The field of view discriminators can in particular be formed as gap apertures.

According to an aspect, a method for interferometric measurement by means of a double beam interferometer comprises:

splitting an incident light beam transmitted from a spatially expanded object into a first partial beam and a second partial beam using a beam splitter unit;

a first and second deflection, in particular a first and second reflection of the first partial beam using a first beam deflection unit;

a first and second deflection, in particular a first and second reflection of the second partial beam using the first beam deflection unit or using a second beam deflection unit, wherein the first and second deflection of the first partial beam and the second partial beam generate a lateral shear;

spatially selecting at least a part of the first partial beam after the splitting and prior to the second deflection by means of a first field of view discriminator unit; and spatially selecting at least a part of the second partial beam after the splitting and prior to the second deflection by means of a second field of view discriminator unit;

sending the incident light beam through a lens prior to the splitting to generate a plurality of coherent image points of the spatially expanded object in an image plane between the beam splitter unit and a detector;

at least partially spatially overlaying the first partial beam and the second partial beam using the beam splitter unit;

at least partially rendering the plurality of coherent image points while at the same time generating a plurality of spatial interferograms on a detector field of the detector on the basis of the spatial overlay;

recording the plurality of interferograms using the detector;

Fourier transforming the plurality of spatial interferograms to generate a plurality of spectrums, and based thereon, generating a hyperspectral image of at least a section of the spatially expanded object.

The method in particular comprises the steps that are triggered and at least partially executed by means of at least one computing unit:

multiple simultaneous recording of the plurality of spatial interferograms at respectively different points in time;

Fourier transforming the plurality of spatial interferograms recorded at respectively different points in time to generate a plurality of spectrums; and generating a hyperspectral image of the spatially expanded object.

The following describes further embodiments, features, and examples that firstly do not restrict the invention, and secondly can be combined with each other, provided they do not exclude each other.

The invention relates to a Fourier transformation spectrometer with at least partial hyperspectral single shot imaging of a measured object as a product of a calculation using a computer system with a computing program to obtain spectrums by means of Fourier transformation. The Fourier-Transformation spectrometer has a double-beam interferometer that is arranged downstream of an upstream lens acting as an imaging system for the measured object. This upstream lens with an optical axis OAI facing the double beam interferometer can in this case be formed with one, two, or also several stages. Input beams enter the double beam interferometer by means of the upstream lens.

These input beams are in this case generally understood to be an ensemble of input beams because imaging information is transported and a separate input beam is mapped to each image point, so that a plurality of input beams is then also mapped to a plurality of image points. An ensemble of input beams then generally exists. In the further description in the figures, a beam ultimately refers to the ensemble of beams, and one beam is identified as a representative or shown in the figures. Hereinafter, the same is also the case for partial beams. Each partial beam is in the sense of the invention in this case representative for an ensemble of partial beams.

The double beam interferometer can comprise firstly either a beam splitter with a planar beam splitter surface and wherein the beam splitter is used for both beam splitting in the beam splitter plane ET, thus forming two partial beams TB1 and TB2, and also for at least partial beam unification in the beam splitter plane ET using a lateral shear s between the two partial beams TB1 and TB2. In this case, the invention relates to a Michelson-Type Interferometer and/or a cyclical double beam interferometer.

Or secondly, two beam splitters, each with a planar beam splitter surface, wherein the first beam splitter is used for beam splitting in the beam splitter plane ET, thus forming two partial beams TB1 and TB2 with a lateral shear s, and a second beam splitter for at least partial beam unification in the beam splitting plane using a lateral shear s between the two partial beams. The invention in this case relates to a Mach-Zehnder Interferometer.

The beam splitter surface can either be formed by a beam splitter layer, a beam splitter foil, and/or a lattice.

The optical axis OAI of the upstream lens facing the double beam interferometer, but where applicable also the optical axis OAI of the last optical component of said lens, or the optical axis OAI on the input of the double beam interferometer and the normal NT of the beam splitter plane ET generally span a reference plane RE on the double beam interferometer. This reference plane RE is typically vertical in relation to the beam splitter plane ET. On a Mach-Zehnder Interferometer, it is typically the first beam splitter whose beam splitter plane ET defines the reference plane RE.

A preferably two-dimensional raster detector for recording spatial interferograms is preferably arranged downstream of the double beam interferometer.

The raster detector can be a UV camera, and a VIS-CCD and/or a VIS-CMOS camera in the visible spectral range (VIS). An InGaAs camera can be advantageously used in the near infrared spectral range. A Focal Plane Array (FPA) (also called IRFPA), which is also cooled if appropriate, is used as a raster detector in the medium infrared range. A mercury-cadmium telluride compound (MCT) is advantageously used for hybrid CMOS FPA technology. Bolometer matrix detectors, in particular microbolometers, can be used for the entire infrared range. Matrix detectors are preferably used for this invention.

For any of the already aforementioned technologies and spectral ranges, it is preferably also possible to arrange two and/or several fast line detectors downstream of the double beam interferometer. In this case, the individual line detectors are preferably for purposes of primary data recording generally arranged in parallel to each other in a common detector field These line detectors are however digitally-electronically independent of each other during data recording. These line detectors are in particular operated independently to achieve a maximum readout speed. The number of line detectors preferably corresponds to the number of measurement points on the object. The individual pixels of a line can in this case also be formed with a particularly high aspect ratio to detect the largest possible amount of light energy for purposes of obtaining a high signal-to-noise ratio. Such applications can in particular be used for analyzing turbulent processes.

The upstream lens and or the lens system arranged in front of the double beam interferometer—taking into account the position of the measured object—in particular generates an image or at least a partial image of the measured object in the direction of the light with the image located generally arranged downstream of the beam splitter, but typically also upstream of the raster detector. The upstream lens and/or lens system can consist of refractive and also of mirror components, but can also consist of a combination of mirror components and refractive components.

A plurality of spatial interferograms can be formed with the involvement of an anamorphic imaging stage arranged downstream of the double beam interferometer. This anamorphic imaging stage can consist of refractive components, but can also consist of mirror components. The cylinder optics in particular can be formed using a mirror component. The spatial interferograms are formed on the two-dimensional raster receiver, and each recorded object point and/or object spot on the measured object is mapped to a spatial interferogram. The measured object spot can in this case firstly be very fine, or nearly correspond to the diffraction-limited resolution increment, when the objective has a high lateral resolution. But the recorded object spot can secondly also be comparatively large when high lateral resolution of the measured object is of secondary importance, but the requirement calls for a high spectral resolution and particularly fast measurements. For a comparatively large recorded object spot as a measurement spot, the Fourier spectroscopy described herein is superior to dispersive spectroscopic methods, since a high spectral resolution for the former is not physically linked to a fine gap opening, as is the case for dispersive spectroscopic methods. For this latter method, the signal-to-noise ratio is as a result generally significantly weaker as with Fourier spectroscopy, given equivalent spectral resolution. However, the image resolution typically declines for large measurement spots. According to Jacquinot, in particular the transmitted light index advantage of Fourier spectroscopic methods applies, but typically at the expense of lateral resolution. Generally, a significantly better signal-to-noise ratio can be achieved and/or measurements can be taken faster than with dispersive spectroscopic methods, which use diffraction lattices and/or prisms.

Additionally, for purposes of illuminating the measured object, the double beam interferometer can firstly either be equipped with a light source that is preferably controllable and can form light patterns. And secondly, the measured object can also be self-radiating, such as a hot exhaust cloud with large radiant intensity in the infrared spectral range.

The double beam interferometer with two interferometer arms can firstly be formed as a noncyclical interferometer and can have one double-mirror periscope reflector each in every interferometer arm. This has the advantage on a noncyclical double beam interferometer, or a Michelson-Type Interferometer and/or a Mach-Zehnder Interferometer, with four mirrors, that the optical distance difference and the lateral shear can be adjusted independently of each other. Or, secondly, respectively one triple mirror reflector and/or respectively one triple mirror prism is at least approximately arranged in corner cube form in every interferometer arm. In the noncyclical double beam interferometer, these reflectors preferably are of equal construction.

The difference of the mirrors or mirror surfaces in the two interferometer arms is then generally zero. A field of view discriminator can be arranged in every interferometer arm of a double beam interferometer in a position preferably between one third and two thirds of the optical distance in the beam path between beam splitting and beam reunification. These two fields of view discriminators are generally at least approximately optically conjugated to each other. When the field of view discriminator is not structured, the latter can also be formed as a classic field of view aperture, for example in the form of a thin shading aperture.

Alternatively, the double beam interferometer can be formed as a cyclical double beam interferometer, that is to say in particular with two plane mirrors that form a periscope arrangement, wherein the two plane mirrors are not equidistant from the beam splitter plane ET that contains the beam splitter surface. Additionally, the two plane mirrors are at least approximately aligned vertically, in general in relation to the reference plane RE. As a result, a double mirror periscope reflector is created in the cyclical double-beam interferometer.

Alternatively, the double beam interferometer can be formed as a cyclical double beam interferometer with two planar mirror surfaces, of which respectively exactly one mirror surface is formed on respectively one mirror prism made of refractive material. As a result, this creates a double mirror prism arrangement that is formed with respectively two mirror prisms. On this arrangement, the two planar mirror surfaces of a mirror prism are not equidistant from the beam splitter plane ET that contains the beam splitter surface, and are at least approximately aligned vertically in relation to the reference plane RE.

Firstly, two plane mirrors can be arranged that form a double mirror prism arrangement, and therefore on the one hand as pairs form a periscope arrangement in a cyclical double beam interferometer that can in particular be shifted with a predetermined value to the beam splitter plane ET.

Secondly, the two mirror prisms of the double mirror prism arrangement can be shifted with a predetermined value to the beam splitter plane ET. The double mirror prism arrangement represents a mirror prism pair. Exactly one planar mirror surface is in this case generally mapped to each mirror prism. An arrangement with two mirror prisms that is configured as a double mirror prism arrangement with one planar mirror surface each can then also be seen as a periscope arrangement, and also represents a double mirror periscope reflector.

On each plane mirror or on each mirror surface in the double beam interferometer, the rays of a partial beam typically only experience a one-time reflection each.

The periscope arrangement as an air arrangement is therefore shifted slightly laterally at a predetermined value to the beam splitter plane ET and the double mirror prism arrangement with the two planar mirror surfaces is shifted slightly laterally at a predetermined value in relation to the beam splitter plane ET.

An angle epsilon can generally exist in a cyclical double beam interferometer in the reference plane RE, both between the two plane mirrors, which form a periscope arrangement—that is to say specifically a double mirror periscope reflector—and also between the two planar mirror surfaces of the double mirror prism arrangement, which ultimately also represent a double mirror periscope reflector. This angle epsilon is formed in particular by two straight lines g1 and g2 projecting from the plane mirrors or from the planar mirror surfaces in the reference plane RE. The half angle psi is half of the angle epsilon, and is generally essentially an acute angle with a value greater than 20 degrees and a value less than 30 degrees.

The half angle psi is furthermore preferably formed with a value greater than or approximately equal to 22 degrees and with a value less than approximately 29 degrees.

The half angle psi is furthermore preferably formed with a value greater than approximately 24 degrees and a value less than approximately 28 degrees, so that a comparatively large aperture angle can be realized in the cyclical double beam interferometer that can be up to approximately ten degrees.

In an image plane in the double beam interferometer, the upstream lens generates image points of illuminated and/or self-luminescent and/or light-scattering object points of the measured object Respectively one image plane of the rendered measured object that is determined by the upstream lens and the location of the measured object is at least approximately mapped to a field of view discriminator in each arm of the double beam interferometer.

The double beam interferometer can have a first image plane and a second image plane that are optically conjugated to each other, and that are each determined by the upstream lens, the location of the measured object, and the double beam interferometer, The first image plane is mapped to a first field of view discriminator, and the second image plane is mapped to a second field of view discriminator in the double beam interferometer These field of view discriminators are each formed with at least one nondiscriminating region in transmission, that is to say a pass-through area, for at least one nondiscriminating region in reflection, that is to say a reflecting region. This reflecting region is preferably formed comparatively narrow.

These two fields of view discriminators can in this case be arranged in the double beam interferometer such that at least an approximate optical conjugation exists between these field of view discriminators, and these field of view discriminators are therefore optically conjugated. This means that the one field of view discriminator represents the image of the other.

The image of the measured object in the double beam interferometer is in this case generally preferably at least slightly larger than the nondiscriminating region of a field of view discriminator that is for example represented by an opening and/or a preferably narrow reflecting region.

Preferably, an at least approximate parallelity exists in a Michelson-Type Interferometer between the main beams of the outbound and the returning beam in an arm of the Michelson-Type Interferometer.

For each main beam in an arm of the Mach-Zehnder Interferometer, there is preferably a parallel main beam in the other arm of the Mach-Zehnder Interferometer.

The double beam interferometer with upstream lens, preferably with a flashlight source synchronized to the raster detector, can preferably also be formed as a mobile measurement head.

The upstream lens to render the measured object is preferably at least approximately telecentrically formed on the side facing the double beam interferometer. The upstream lens can preferably also be formed telecentrically on both sides. A telecentricity on the side facing the interferometer generally significantly reduces the requirements on the downstream optics.

An imaging stage to render the measured object upstream of the double beam interferometer can be omitted by arranging the two field of view discriminators in the double beam interferometer, where according to the invention two coherent images of the measured objects are generated. The field of view discriminators can in this case preferably also cause a confocal discrimination when a confocal arrangement applies. In particular in a boundary case, the field of view discriminators can, when these are formed as pinholes and/or as micro-mirrors, have the size of an Airy disk and/or a gap opening and/or mirror stripes with the width of a diameter of an Airy disk. But field of view discriminators of such a small size are rather not the focus of the invention as the advantage of Fourier spectroscopy versus dispersive spectroscopy is diminished for very small field of view discriminators. As is known, dispersive spectroscopy must rely on a narrow gap at higher spectral resolution, whereas this is not the case for Fourier spectroscopy due to the Jacquinot advantage known to the person skilled in the art.

The relatively coarser field of view discrimination typical here when compared to the large surface area field of view discriminators in double beam interferometers used for confocal microscopy generally also does not create a geometrical-optical depth of field focal range problem, even when the object has a slightly greater depth of field. For a comparatively short focal length upstream lens and distant objects and/or relatively flat objects, the depth of field extent of the image is relatively low, so that the model of the image plane used of here is quite a good match. It is advantageous when the upstream lens is preferably equipped with an autofocus system in order to at least render the relevant regions of a measured object in comparative focus in the plane of the field of view discriminators, so that at least a hyperspectral partial image can be obtained.

On measured objects with a greater depth of field and/or for very small measured objects, it is generally necessary to execute a method with a depth of field scan, and it is generally necessary to record spatial interferograms in every depth of field position, or in layers.

Additionally, in a double beam interferometer, every field of view discriminator is preferably mapped to a double mirror periscope reflector or to a triple mirror corner cube reflector. The field of view discriminator can in this case be arranged between two plane mirrors of the double mirror periscope reflector or in the triple mirror reflector itself, or can be mapped to these reflectors. A field of view discriminator can preferably also be arranged upstream or downstream of the double mirror periscope reflector or the triple mirror reflector in the beam path. The triple mirror reflector can this case be formed as a triple prism or as a hollow cube. In this case, generally two double mirror periscope reflectors are arranged in a Michelson-Type Interferometer and in a Mach-Zehnder Interferometer respectively. By contrast, respectively one double mirror periscope reflector is arranged in a cyclical double beam interferometer, and two field of view discriminators are then mapped to this cyclical double beam interferometer Furthermore, when rendering the measured object in a double beam interferometer, the image plane is preferably at least approximately brought to coincide with respectively one field of view discriminator. Only then can the field of view be accurately discriminated.

Furthermore, the two field of view discriminators in a double-beam interferometer are preferably formed in the shape of a gap. The measured points can then be easily mapped to the lines of a raster detector.

Furthermore, at least one field of view discriminator in a double-beam interferometer is preferably formed as a computer controllable, spatial light modulator. As a result, the field of view discriminator can be optimally adjusted to the metrology task with a variable size and shape. Liquid crystal displays (LCDs) in transmission or reflection and/or also digital micro-mirror arrays (DMDs) can be used. The latter are in particular used in the infrared spectral range.

The two field of view discriminators in a Michelson-Type Interferometer furthermore preferably formed and arranged as a gap aperture, and respectively exactly one gap aperture is positioned in each arm of the Michelson-Type Interferometer.

In a Michelson-Type Interferometer, every gap aperture is furthermore preferably arranged in optical conjugation to the apparent end mirror surface of the respective interferometer arm.

In a Michelson-Type Interferometer that represents an example for a double beam interferometer, the field of view discriminators are furthermore preferably respectively arranged in a position at least approximately at half of the optical distance in the beam path between the beam splitting and beam reunification.

Every double mirror periscope reflector in a Michelson-Type Interferometer is furthermore preferably equipped with a beam deflection of at least approximately 180 degrees. The double mirror periscope reflector then represents a 90-degree rooftop reflector.

At least one field of view discriminator in a Michelson-Type Interferometer is furthermore preferably formed with a computer-controllable liquid crystal display (LCD). The latter is preferably arranged between the two mirrors of the double mirror periscope reflector and is used in transmission. Two liquid crystal displays of equal construction are preferably used in this case.

The field of view discriminators are furthermore preferably arranged in a Mach-Zehnder Interferometer, and in this case, respectively exactly one field of view discriminator is positioned in each arm of the Mach-Zehnder Interferometer. Because the aberrations in the two arms of a Mach-Zehnder Interferometer can be different, in particular when a beam splitter plate tilted in the beam path is used instead of a beam splitter cube, the gap-shaped field of view discriminators can also be formed with slightly different gap widths. For example, when the opening error in an arm of the Mach-Zehnder Interferometer is not corrected, this generates a slightly out of focus image even of a narrow region of the measured object. The selected gap opening can in this case be slightly larger in comparison to an interferometer arm largely without aberrations when rendering a narrow region of the measured object.

In a double beam interferometer, the field of view discriminators are furthermore preferably respectively arranged in a position at least approximately at half of the optical distance in the beam path between the beam splitting and beam reunification. A comparatively large aperture angle can then be used in the interferometer.

The double mirror periscope reflectors in a Mach-Zehnder Interferometer are furthermore preferably formed with a beam deflection between 45 degrees and 135 degrees. The range of beam deflection between 75 degrees and 105 degrees is preferred in particular.

At least one field of view discriminator in a Mach-Zehnder Interferometer is furthermore preferably formed as a digital micro-mirror array. In this case, a micro-mirror array can preferably be used in a Mach-Zehnder Interferometer in place of a mirror of a double mirror periscope reflector. In this case, only a narrow region on the micro-mirror array is preferably addressed in reflection, wherein also an at least partially in focus image is formed on the micro-mirror array because the incident light is not vertical in this case. In this case, a narrow image section of the measured object is rendered in focus on the micro-mirror array in the addressed region of the latter. The micro-mirror array is then used in place of a conventional plane mirror in a double mirror periscope reflector. In each case, the addressed region of a spatial light modulator also represents the discriminating region of a field of view discriminator. In the second double mirror periscope reflector of the interferometer, a gap aperture can be preferably used between the two plane mirrors, in particular when the measured object is rendered free of aberrations in this interferometer arm. Preferably however, in each of the two interferometer arms of the Mach-Zehnder Interferometer, a plane mirror can preferably be replaced in the double mirror periscope reflector by a digital micro-mirror array. This can facilitate a computer supported adjustment of the arrangement and therefore simplify the adjustment.

In a cyclical double beam interferometer with two plane mirrors or two planar mirror surfaces, a gap opening is preferably arranged in the two opposingly revolving partial beams of the double beam interferometer in respectively one gap aperture or a double-gap aperture as a field of view discriminator in an image plane of the measured object. The first gap opening is in this case located in the first image plane of the measured object in the cyclical double beam interferometer, and the second gap opening in this case is located in the second image plane of the measured object in the cyclical double beam interferometer, which are also optically conjugated. Depending on the location of the image planes, the two gap openings of the individual gap apertures can in this case also be shifted in the depth axis. However, the two gap apertures are generally located between the two plane mirrors or the two planar mirror surfaces of the cyclical interferometer.

The cyclical double-beam interferometer is in this case either constructed with two plane mirrors in an arrangement free of refractive materials in the revolving beam path. Alternatively, the cyclical double beam interferometer is formed by using two mirror prisms with a mirror surface on each of these mirror prisms.

In a cyclical double beam interferometer, these field of view discriminators BFD1 and BFD2 are this case preferably arranged in a position at least approximately at half of the optical distance in the beam path between the beam splitting and beam reunification in each of the two beam paths. However, the field of view discriminators BFD1 and BFD2 are at all times arranged where there is respectively one image plane. This is preferably the region in the cyclical double beam interferometer where the two partial beams TB1 and TB2 do not overlap.

In a cyclical double beam interferometer with two plane mirrors and/or two planar mirror surfaces, a double-gap aperture with respectively two gap openings is furthermore preferably arranged in the two opposingly revolving partial beams of the double beam interferometer in a plane vertical to the main beams of the partial beams TB1 and TB2. The two optically conjugated image planes of the rendering of the measured object fall together in this plane, and thus form a common image plane. For this purpose, the image shifts are made the same in the depth axis in refractive, transparent material of the same type from the beam splitting up to respectively one field of view discriminator in the two arms of the cyclical double-beam interferometer. These are generally preferably solid refractive materials in the double beam interferometer, but a liquid, transparent, refractive material can preferably also be used.

For Fourier transformation spectroscopy with two plane mirrors and/or two planar mirror surfaces, a computer-controllable, transmissive liquid crystal display is furthermore preferably arranged in a cyclical double beam interferometer between these plane mirrors and/or planar mirror surfaces with at least two pass-through areas.

Furthermore, two gap-shaped pass-through areas are preferably embedded in the transmissive liquid crystal display in a cyclical double beam interferometer for Fourier transformation spectroscopy. This is done in interaction with polarized optics and polarized light in the manner known to the person skilled in the art.

In a cyclical double beam interferometer for Fourier transformation spectroscopy, the beam splitter plane ET and the intersection SP of the straight lines g1 and g2 are furthermore preferably separated from each other by the distance d_ST, and this distance d_ST is at least ten wavelengths of the largest wavelength in the spectrum of the detected light. As a result, this minimizes the optical distance difference in the detection plane of the interference DE, thus permitting at least a minimum of spectral resolution. But the distance d_ST is generally significantly larger than ten wavelengths of the largest wavelength in the spectrum, and can in a typical case certainly be several one-hundred wavelengths of the largest wavelength in the spectrum.

In a cyclical double beam interferometer, the straight lines g1 and g2 represent straight lines extended in the reference plane RE, and lie in the surface of the first plane mirror or the second plane mirror and/or in the first and respectively the second planar mirror surface, and each planar mirror surface is in this case an element of a mirror prism.

In a cyclical double beam interferometer for Fourier transformation spectroscopy, respectively one field of view discriminator BFD1 and BFD2 with respectively at least one nondiscriminating region in transmission or reflection are furthermore preferably arranged in each of the two beam paths in the cyclical double beam interferometer with reversed directionality with the partial beams TB1 and TB2. The width b of the nondiscriminating region preferably does not respectively exceed the distance 1.2*d_ST. As a result, an overlap between the partial beams is avoided with great certainty because the field of view discriminators BFD1 and BFD2 centered in relation to the main beam are separated from each other by the distance 1.4*d_ST.

In a cyclical double beam interferometer for Fourier transformation spectroscopy, in each of the two beam paths in the cyclical double beam interferometer with reversed directionality, the width b_S" of the geometrical-optical image of the light source is furthermore preferably formed to be less than the distance d_ST or equal to the distance d_ST at the location of the field of view discriminators. As a result, an adverse overlap between the two partial beams is generally reliably prevented.

In a cyclical double beam interferometer, at least one mirrored staircase with two mirrors each is furthermore preferably arranged in the region Z, where no spatial overlap occurs between the two partial beams TB1 and TB2.

In a cyclical double beam interferometer, two mirrored staircases with two mirrors each, which are preferably miniaturized, are preferably arranged in the region Z, where no spatial overlap occurs between the two partial beams TB1 and TB2. The arrangement of one or of two mirrored staircases permits the purposeful influencing of the lateral shear s and also of the optical distance difference in a cyclical double beam interferometer. In an arrangement of two mirrored staircases, the compensation of the optical paths of the mirrored staircases is provided in a cyclical double beam interferometer; as a result, very small optical distance differences can be generated in a predetermined way based on the difference of the optical distances of the two mirrored staircases.

In a cyclical double beam interferometer, the two mirrors of a first mirrored staircase are preferably formed as plane mirrors and the two mirrors of a second mirrored staircase are preferably formed as plane mirrors in region Z, where there is no spatial overlap between the two partial beams TB1 and TB2. This permits a comparatively cost-effective manufacturing of a mirrored staircase and a comparatively straightforward adjustment of the cyclical double beam interferometer.

In a cyclical double beam interferometer, in region Z where no spatial overlap occurs between the two partial beams TB1 and TB2, the two plane mirrors are preferably respectively arranged in parallel to each other on the first miniaturized mirrored staircase, and the two plane mirrors can be respectively arranged in parallel to each other on the second miniaturized mirrored staircase. This parallel arrangement facilitates a beam offset with the optical axes of the partial beams parallel to each other. This also represents an advantage for manufacturing a mirrored staircase, for example by single point diamond machining, because the deviation of the parallelity of the two plane mirrors can be kept very small.

The two parallel plane mirrors of the first mirrored staircase and the two parallel plane mirrors of a second mirrored staircase can in a cyclical double beam interferometer preferably have a slightly different distance. The parallel plane mirrors of the first mirrored staircase and the two parallel plane mirrors of the second mirrored staircase are therefore spaced at different distances from each other. This permits the introduction of an additional optical distance difference between the two partial beams with reversed directionality in a cyclical double beam interferometer, because each partial beam TB1 and TB2 is mapped to a different mirrored staircase. The mirrored staircases are preferably miniaturized in comparison to the first and to the second plane mirror in the revolving beam path of the cyclical double beam interferometer. Preferably, either one mirrored staircase each is mapped to one field of view discriminator, preferably in the form of a gap aperture, and/or respectively one plane mirror of a mirrored staircase is preferably sufficiently narrow, in knife-edge shape in an extreme case, so that it can then directly act as a field of view discriminator in the image plane. The field of view discriminator in the image plane can also be preferably formed as a raster shading aperture, preferably also as a pinhole array, optimized for the pinhole size for the respective spectral range. Moreover, a micro-mechanical, computer controllable pinhole array can also preferably be used as a field of view discriminator in the image plane, wherein the pinholes are individually addressable. If by contrast a narrow mirror is arranged as a field of view discriminator in the image plane, the latter can also be formed as a computer-controllable digital micro-mirror array. In conjunction with a scanner, these arrangements can also be used in the terahertz range for imaging airport scanners for passengers and cargo using the transmitted light method with spectral resolution. In this case, the person and/or the cargo is positioned between an elongated terahertz radiation source and the spectrometer.

The use of mirrored staircases in a cyclical double beam interferometer is then particularly advantageous for the midinfrared and far infrared spectral range and for the terahertz range, where the wave-optical depth of field focal range is comparatively large due to the large wavelength of electromagnetic rays, and the optical distance difference additionally introduced in a cyclical double beam interferometer by the different distances between the two plane mirrors of a mirrored staircase preferably does not exceed the wave-optical depth of field focal range. This minimizes nonlinearities in the spatial interferograms. On the other hand, the difference of the distances between the two plane mirrors should preferably be at least two wavelengths of the largest wavelength in the employed spectral range in order to asymmetrically form spatial interferograms on the raster detector In the case of two mirrored staircases in a cyclical double-beam interferometer with slightly different distances between the plane mirrors of said mirrored staircases, which result in different optical distances, each mirrored staircase can preferably additionally be mapped to a plane parallel plate made of refractive material in order to compensate image shifting. The plane parallel plates are in this case formed with different thicknesses and/or with different refractive indexes. Where required, a complete compensation of the image shifting can then be achieved for different optical distances of mirrored staircases. This also represents an interesting approach for the near infrared and midinfrared spectral range in order to obtain undisrupted spatial interferograms when the provided wave-optical depth of field focal range is not very large.

It is additionally also possible that the mirrored staircases are formed as prisms with refractive materials.

Furthermore, in a cyclical double beam interferometer, in region Z where no spatial overlap occurs between the two partial beams TB1 and TB2, the first mirrored staircase and the second mirrored staircase are combined into a double mirrored staircase using a center web, and the two inner plane mirrors are respectively arranged in parallel to each other on a side of the center web of the double mirrored staircase. The embodiment and arrangement of a compact double mirrored staircase permits a particularly large aperture angle alpha, because the inner plane mirrors are spatially arranged comparatively close to each other by employing a preferably comparatively thin center web with one mirror surface each. A thin center web with one mirror surface each is then preferably arranged in the center of a double mirrored staircase. Moreover, the embodiment of a double mirrored staircase—which is preferably manufactured in a single operation using single point diamond machining on an ultra-precision machine—permits keeping the pyramid error of the four plane mirrors very small. The cyclical interferometer is characterized by high ruggedness due to the preferred manufacturing of the double mirrored staircase as a compact monolith made of metal using single point diamond machining.

In a cyclical double beam interferometer, a field of view discriminator is preferably mapped to at least one mirrored staircase. Generally, the first mirrored staircase and also the second mirrored staircase are each preferably mapped to one field of view discriminator.

Furthermore, the field of view discriminator in a cyclical double beam interferometer is preferably either formed as a gap aperture, as a narrow pinhole array, and/or as a raster, computer-controllable, micromechanical pinhole array.

For a preferred arrangement of two field of view discriminators—and a first field of view discriminator is mapped to a first mirrored staircase and a second field of view discriminator is mapped to a second mirrored staircase—these two fields of view discriminators preferably of equal construction. These field of view discriminators are either respectively preferably formed as a gap aperture and/or preferably formed as respectively a narrow pinhole array and/or preferably formed as respectively a raster, micro-mechanical, computer-controllable pinhole array. The micro-mechanical, computer-controllable pinhole array can then preferably also be designed as a micro-mechanical component on which the pinholes are individually addressable by computer-control. The latter can increase the flexibility of the spectrometer and can contribute toward reducing the optical interference between the two partial beam paths for poorly cooperating measured objects and/or measurement fields, which for example have a strong internal structure with respect to the radiant energy.

In a cyclical double beam interferometer, a field of view discriminator is furthermore preferably formed as a narrow plane mirror that forms one of the two plane mirrors of a mirrored staircase. Other field of view discriminator such as a gap aperture are then redundant.

In a cyclical double beam interferometer, a field of view discriminator is furthermore preferably formed as a computer-controllable digital micro-mirror array (DMD) in at least one mirrored staircase. A plane mirror of a mirrored staircase is then replaced by a computer-controllable digital micro-mirror array (DMD).

In the long-wave spectral range, due the comparatively large depth of field focal range induced by large wavelengths the generally function-related tilt of digital micro-mirror arrays is rather not a problem when the addressed range on the tilted micro-mirror array is formed comparatively narrow.

A cyclical double beam interferometer with two mirrored staircases in the revolving beam path furthermore preferably has a comparatively small wedge angle tau_1 from up to 10 degrees between the two plane mirrors of the first mirrored staircase and also a comparatively small wedge angle tau_2 from up to 10 degrees between the two plane mirrors in the second mirrored staircase, and the values of these two wedge angles tau_1 and tau_2 are made at least approximately equal in the two mirrored staircases. The minimum approximate equivalency of the values of the wedge angles tau_1 and tau_2 is a condition for creating high-contrast spatial interferograms in the detection plane. Inserting the wedge angles tau_1 and tau_2 between the two plane mirrors of the first and the second mirrored staircase causes a bending of the two beam paths in the cyclical double beam interferometer This bending preferably occurs toward the beam splitter in the cyclical double beam interferometer and thus somewhat closes the beam path. This to a certain extent minimizes the optical distance in the cyclical double beam interferometer, which is the condition for the ability to form the largest possible opening angle for the input beam and therefore for the two partial beams TB1 and TB2 in the interferometer. When the location of the components of the cyclical double beam interferometer are optimized, a numerical aperture of NA=0.2 can then be achieved for the input beam and also for the two partial beams on a cyclical double beam interferometer. The bending toward the beam splitter causes the two main beams of the respective partial beams projecting upward and downward from a mirrored staircase to describe an angle of less than 180 degrees on the side of the beam splitter, for example an angle kappa of 168 degrees. The angle kappa according to the equation (1)

kappa=180 degrees−2(tau_1+tau_2)      Equation (1)

then exists between the main beam HTB1a, which projects from the first mirrored staircase, and the main beam HTB2a, which projects from the second mirrored staircase, on the side facing the interferometer. The angle kappa is preferably formed to be less than 180 degrees, but preferably formed to be not less than 140 degrees.

In a cyclical double beam interferometer, at least one miniaturized mirrored staircase is preferably arranged in the region Z, wherein at least one mirror is formed with a weak curvature. However, it is better to preferably form both mirrors of a mirrored staircase with a weak curvature. A weak wavefront can then be formed in a partial beam within the cyclical double-beam interferometer. The location in the depth axis of the image can then for at least one partial beam be influenced such that the two coherent images are nevertheless located in a common image plane even for different optical distances for the main beams in the two partial beams in the cyclical double beam interferometer, which are caused by the slightly different mirror distances of the two mirrored staircases. It is then possible to largely avoid nonlinearities in the spatial interferograms with a common image plane of the coherent partial images.

There are then generally a total of six mirrors arranged in a preferred arrangement of two mirrored staircases in a cyclical double beam interferometer, of which four mirrors are however essentially miniaturized Two mirror prisms of equal construction and each made of the same refractive material, that is to say a first and a second mirror prism are furthermore preferably arranged in a cyclical double beam interferometer for Fourier transformation spectroscopy in a revolving beam path, and said mirror prisms are each formed with a single mirror surface. These two mirror prisms each have the same acute angle psi between the mirror surface and the respectively nonreflective surface. The nonreflective surfaces of the mirror prisms are in this case respectively used for beam entry and also for beam exit. Two field of view discriminators are positioned between these two mirror prisms of equal construction. These can be positioned in a parallel airgap between the two mirror prisms of equal construction and/or can also be embedded in a cement layer that mechanically and also optically joins the two mirror prisms. The two field of view discriminators are preferably formed by two individual gap apertures and/or also by a double gap aperture whose gaps each represent the field of view discriminators. However, the use of a liquid crystal display is preferably also possible, the latter in conjunction with polarized optics having two pass-through areas, preferably in gap form. The two mirror prisms of equal construction are preferably also of equal construction.

Two further acute, and isosceles triangle prisms, that is to say a third and a fourth prism that are also of equal construction, are arranged in this cyclical interferometer. These two triangle prisms each twice have an angle of 2 psi. The embodiment of the four prisms with the angles stated here, based on the half angle psi, permit a generally vertical beam entry and beam exit for the main beams of the two partial beams TB1 and TB2.

A beam splitter layer is located between these two triangle prisms, which are cemented together. These two triangle prisms then form a beam splitter. The beam splitter layer is used for beam splitting and also for beam reunification, wherein a significant, but desirable lateral shear s is created between the partial beams during beam reunification. However, this reference to a beam reunification of the partial beams is not entirely correct since the latter are only united with a lateral shear s, and the unification is then only partial in nature. The interference is at any rate only visible on the detector and is only recorded there.

The acute angle psi on the two mirror prisms of equal construction is greater than/equal to 15 degrees and less than/equal to 30 degrees. A smaller angle for psi than 15 degrees tends to increasingly enlarge the optical distance in the interferometer and increasingly results in an increasingly smaller usable aperture angle alpha. However, a larger angle for psi than 30 degrees then again limits the available space for the partial beam and also increasingly results in a smaller usable aperture angle alpha.

A range of preferably from the 20 degrees to 28 degrees has shown to be particularly suited for the acute half angle psi in the cyclical double beam interferometer in order to achieve a large usable aperture angle alpha in the refractive material. In many cases, an optimum is preferably achieved with an acute half angle psi of 23 degrees to 26 degrees, with an optimum at preferably 24 degrees. This angle range permits an aperture angle in the refractive material of 9 degrees in the cyclical interferometer.

The two acute angles psi in each mirror prism also respectively create an obtuse angle 2rho, whose value rho is determined by the difference of 90 degrees and the value of the acute angle psi. A vertical axis beam path through every mirror prism can be achieved by observing this condition for the angle rho, which very significantly minimizes the aberration in the beam path and thus allows largely undisrupted spatial interferograms to be obtained in the first place.

However, in a cyclical double beam interferometer for Fourier transformation spectroscopy, two mirror prisms of equal construction can also be arranged at an angle psi, the mirror prisms each having a single mirror surface. In this case, a beam splitter is arranged here in the cyclical double beam interferometer, which is mapped to these mirror prisms. The beam splitter is in this case either formed as a foil and/or as a fine wire lattice with a flat surface and a parallel arrangement of the wires. The acute half angle psi in the cyclical double beam interferometer is preferably formed with a value greater than or equal to 20 degrees and less than or equal to 30 degrees. This angle range has been shown to be particularly suited to achieve a large usable aperture angle alpha. In many cases, an optimum is preferably achieved with an acute half angle psi of 24 degrees to 27 degrees, with an optimum at preferably 26 degrees. The latter permits an aperture angle alpha in the refractive material of at least 9 degrees.

Furthermore, preferably two mirror prisms of the same angle, and preferably a further acute and isosceles triangle prism are arranged in a cyclical double beam interferometer for Fourier transformation spectroscopy, wherein the triangle prism is cemented to one of the two mirror prisms. A beam splitter layer is mapped to the cement layer. The two mirror prisms each have the same acute angle psi between the mirror surface and at least one nonreflective surface. The acute and isosceles triangle prism has the same angle of 2 psi twice.

Each of the two field of view discriminators are arranged between the first mirror prism and the second mirror prism, either in a parallel airgap and/or embedded in a cement layer.

One of these nonreflective surfaces of the first mirror prism is in this case respectively used for beam entry and also for beam exit. One nonreflective surface of the second mirror prism is in this case respectively used for beam entry and also for beam exit. The embodiment of the three prisms with the angles stated here, based on the half angle psi, permit a generally vertical beam entry and beam exit for the main beams of the two partial beams TB1 and TB2.

The acute half angle psi in the cyclical double beam interferometer has a value greater than or equal to 15 degrees and less than or equal to 30 degrees. Here as well, an angle larger than 30 degrees for the acute angle limits the beam space and increasingly results in a smaller usable aperture angle alpha. An angle less than 15 degrees for the acute angle also increasingly results in a smaller usable aperture angle alpha in the beam space in the cyclical double beam interferometer, which is not the aim.

A range from preferably 20 degrees to 28 degrees has also shown to be particularly suited for the acute half angle psi in the cyclical double beam interferometer in order to achieve a large usable aperture angle alpha in the refractive material. In many cases, an optimum is preferably achieved with a half angle psi of 22 degrees to 26 degrees, with an optimum at preferably 24 degrees. The latter permits an aperture angle alpha in the refractive material of at least 9 degrees without cutting off the beam cone.

Here as well, the two acute angles psi in each mirror prism also respectively create an obtuse angle 2rho, whose value rho is determined by the difference of 90 degrees and the value of the acute angle psi. A vertical axis main beam path through every mirror prism can be achieved by observing this condition, which significantly minimizes the aberration in the optical system.

Furthermore, preferably two mirror prisms made of the same refractive material are arranged in a cyclical double beam interferometer for Fourier transformation spectroscopy, the mirror prisms each having only a single mirror surface. The two mirror prisms each have a first acute angle psi, a second acute angle 2 psi, and a third angle with the value 180 degrees minus 3 psi. At least three angles on the two mirror prisms then respectively match. Furthermore, a plane parallel plate made of refractive material is arranged between these two mirror prisms, and the plan parallel plate is fixed between these two mirror prisms by two optically transparent cement layers.

The two mirror prisms preferably are of at least approximately of geometrically equal construction. However, these are then shifted slightly in relation to each other so that the glass path lengths in the two revolving beam paths are equivalent.

In this case, a beam splitter layer is either firstly preferably applied on the side of the plane parallel plate facing the mirror prism, or alternatively, the beam splitter layer is applied on the mirror prism, preferably on the side of the plane parallel plate facing the plane parallel plate. This arrangement is readily adjustable and provides optimum conditions to minimize aberrations for the propagation of the beam. When cemented, the front faces of the mirror prisms can for adjustment purposes for example be polished subject to optical observation for the purpose of optically scanning the latter, for example using an auto-collimation telescope and focus sensors. At an angle of 26 degrees for the acute half angle psi, an aperture angle in the refractive material of 9 degrees can be reliably achieved in the cyclical double beam interferometer, which represents an optimum. This also applies for the acute half angle psi of 24 degrees. The two mirror prisms of equal construction are preferably manufactured in a single operation to thus at least approximately achieve construction equivalency.

A Fourier transformation spectrometer with at least partial hyperspectral single shot imaging of a measured object as a product of a calculation using a computer system to obtain spectrums by means of a Fourier transformation with an upstream lens as imaging system for the measured object has a cyclical double beam interferometer that is positioned upstream of the upstream lens, which generates an input beam.

This input beams are in this case generally understood to be an ensemble of input beams because it transports imaging information and a separate input beam is mapped to each image point, so that a plurality of input beams is then also mapped to a plurality of image points. An ensemble of input beams then exists. In the further description in the figures, a beam always ultimately refers to the ensemble of beams, and one beam is identified or shown in the figures as a representative for a plurality of beams.

The cyclical double beam interferometer comprises:
a beam splitter with a planar beam splitter surface
and a raster detector at the output of the double beam interferometer.

The beam splitter is used for both beam splitting in the beam splitter plane, thus forming two partial beams (TB1, TB2) from the input beam, and also for at least partial beam unification in the beam splitter plane using a lateral shear s between the two partial beams. Accurately formulated, a first ensemble and a second ensemble of partial beams is respectively created after the beam splitting because every partial beam is only mapped to one image point, but in this case images are created in the interferometer, which requires a plurality of beams, because for every image point, there is a beam associated with the latter.

A reference plane exists on the cyclical double beam interferometer, wherein the reference plane is spanned by the normal of the planar beam splitter surface and by the optical axis of the upstream lens on the input of the interferometer, The upstream lens arranged upstream of the cyclical double beam interferometer—taking into account the position of the measured object—generates an image or at least a partial image of the measured object in light direction, generally downstream of the beam splitter, but generally upstream of the raster detector. With the involvement of an anamorphic imaging stage arranged downstream of the cyclical double beam interferometer a plurality, but at least two, spatial interferograms are generated, wherein these spatial interferograms are rendered on the two-dimensional raster receiver, and wherein an object point on the measured object is mapped to every spatial interferogram, At least two spatial interferograms are generated at a minimum.

The cyclical double beam interferometer is firstly formed with two plane mirrors that form a periscope arrangement, wherein the two plane mirrors are equidistant from the beam splitter plane ET that contains the planar beam splitter surface and are at least approximately arranged vertically to the reference plane (RE). The equidistance between the two plane mirrors results in a symmetrically constructed cyclical double-beam interferometer.

The cyclical double beam interferometer is alternatively formed with two mirror surfaces, of which respectively exactly one is formed on one mirror prism each made of refractive material, thus creating a double mirror prism arrangement. The double mirror prism arrangement is formed with respectively exactly two mirror prisms. On this double mirror prism arrangement, the two planar mirror surfaces of a mirror prism are equidistant from the beam splitter plane ET that contains the beam splitter surface, and are at least approximately aligned vertically to the reference plane (RE). Here as well, the equidistance between the two mirror surfaces results in a symmetrically constructed cyclical double-beam interferometer.

An angle epsilon with double the value of the half angle psi exists between the two plane mirrors that form the periscope arrangement and/or between the mirror surfaces of the double mirror prism arrangement. Said angle epsilon is represented by two straight lines g1 and g2 projecting from the plane mirrors or from the planar mirror surfaces in the reference plane (RE), and the half angle line of the angle epsilon lies in the beam splitter plane ET. The half angle of epsilon, the half angle psi, is formed with a value greater than 20 degrees and with a value less than 30 degrees.

The symmetrically constructed cyclical double beam interferometer has a first image plane and a second image plane that are each determined by the upstream lens, the location of the measured object, and the double beam interferometer. The first image plane BEI1 is mapped to a first field of view discriminator and the second image plane is mapped to a second field of view discriminator in the double beam interferometer, and said two field of view discriminators are arranged in the symmetrically constructed cyclical double beam interferometer such that an at least approximate conjugation is created between these field of view discriminators, and in the cyclical double-beam interferometer, one optical functional assembly each to generate a beam shear is mapped to one field of view discriminator each between the plane mirrors or the mirror prisms in the revolving beam path that are directly mapped to the beam splitter, and the optical functional assemblies generate a beam shear in the preferably respectively opposing direction, thus generating a lateral shear s at the output of the cyclical double beam interferometer.

In particular, the optical functional assemblies are formed as two mirrored staircases in air or as two at least rhomboid-like mirror prisms to generate a beam shear in a cyclical double beam interferometer. The main beams of the partial beams downstream of the plane mirrors, which form a periscope arrangement in the cyclical double beam interferometer in the revolving beam path, are colinear in the common space between these plane mirrors until these main beams impact the mirrored staircases and/or the rhomboid mirror prisms. These mirrored staircases and/or mirror prisms cause a shear of the main beams, which is preferably in opposing direction to generate the largest possible lateral shear s at the output of the cyclical double-beam interferometer.

Furthermore, a field of view discriminator BFD1, BFD2 is preferably formed in the cyclical double beam interferometer as a gap aperture and/or as a narrow mirror. Both field of view discriminators can in this case each be formed as a gap aperture and/or as a narrow mirror. But one field of view discriminator can also be formed as a gap aperture and one field of view discriminator as a narrow mirror. But at least one field of view discriminator can preferably also be formed as a computer-controllable digital micro-mirror array (DMD).

In summary, the following applies: When two differently formed mirrored staircases are used in a cyclical double beam interferometer, it is then also possible to cause the distance d_ST, that is to say the distance of the intersection SP from the beam splitter plane ET, to approach zero. A strict symmetry then exists in the cyclical double-beam interferometer with respect to the position of the two plane mirrors and/or the mirror surfaces on periscope prisms. The already described mirrored staircases are comparatively small in comparison to the two plane mirrors and/or the mirror surfaces. These mirrored staircases are in terms of their type either formed as hollow bodies or are in terms of their type formed as mirror prisms with two mirror surfaces. The mirror prism is in this case preferably formed as a rhomboid mirror prism. The mirrored staircases preferably create a parallel shear of the partial beams, which is however not mandatory. It is sufficient when a shear with the same angle value is created.

A desired lateral shear s can be created between the partial beams using two of these mirrored staircases of the respectively same type. Based on the arrangement of the mirrored staircases, this lateral shear s is preferably created in opposing directions. The optical distances in the two revolving beam paths can also be adjusted by the embodiment of the two mirrored staircases such that slightly different distances are created in the two revolving beam paths for the main beams of the partial beams. This serves the objective of obtaining the spatial interferograms slightly shifted on the raster detector in order to slightly increase the spectral resolution.

Furthermore, a cyclical double beam interferometer for Fourier transformation spectroscopy preferably comprises a double mirror periscope reflector, with the two plane mirrors rotated by up to 6 degrees about the symmetry point S. The double mirror periscope reflector is then rotated out of the symmetry position in a cyclical double beam interferometer. However, a double mirror prism arrangement can preferably also be rotated with the two plane mirror surfaces by up to 6 degrees about the symmetry point S. The surfaces of the two mirror prisms are in this case adjusted in their angular position such that the main beams of the partial beams TB1 and TB2 each pass the mirror prisms vertically. For difficult construction framework conditions, this asymmetry can result in an advantage regarding the use of a large aperture angle alpha.

Furthermore, in a cyclical double beam interferometer for Fourier transformation spectroscopy, in the region Z, where no spatial overlap occurs between the two partial beams TB1 and TB2, a first plane parallel plate positioned at least approximately vertically in relation to the axis and having the geometric thickness h1 and made of optical material with the refractive index n1 is arranged in the partial beam TB1, and also a second plane parallel plate positioned at least approximately vertically in relation to the axis and having the geometric thickness h2 and made of optical material with the refractive index n2 is arranged in the partial beam TB2. A gap aperture that represents a field of view discriminator is in this case mapped to each plate.

When dimensioning the two plane parallel plates, the equation (2) must be at least approximately observed for their geometric thicknesses h1 and h2 and the refractive indexes n1 and n2:

$$h1*(n1-1)/n1 = h2*(n2-1)/n2. \quad \text{Equation (2)}$$

As a result, the axial image shift v1 and v2 introduced by the two plane parallel plates is equal. A complete compensation of the axial image shift is then generated between the two partial beams TB1 and TB2 at the output of the cyclical double beam interferometer.

In this case, the optical distance difference OPD_zykaP at the output of the cyclical double beam interferometer preferably does not exceed the amount of 1 mm based on the equation (3)

$$\text{OPD\_zykaP} = \text{Value}[n1*h1) - (n2*h2)] \quad \text{Equation (3)}$$

In many cases, this optical distance difference OPD_zykaP is preferably only 0.03 mm to 0.2 mm. In the prior art, this is primarily also owed to the availability of raster detectors, such as microbolometer arrays, in the NIR and MIR spectral range, which rarely have more than 1,000 pixels in the width bk of the sensor surface, generally a chip. By contrast, in the VIS spectral range, CMOS chips can have up to 10,000 pixels in the width bk of the chip, resulting in correspondingly higher values for the optical distance difference OPD_zykaP, which preferably do not exceed 2 mm here.

In many cases, a sensible value is when the optical distance difference OPD_zykaP is approximately 50% of the optical distance difference OPDr, which in turn in many cases is preferably about 0.15 mm for the NIR and the MIR range. This results in a maximum optical distance difference OPD_right of 0.225 mm for detecting a spatial interferogram. This results in a spectral resolution delta sigma as the inverse of the maximum optical distance difference OPD_right to delta sigma of 44.4 cm$^{-1}$. In order to calculate the phase correction when calculating the spectrum by means of fast Fourier transformation, a part of the left interferogram also remains in this case with an optical distance difference OPD_left of 0.075 mm. However, these relationships are widely known to persons skilled in the art of Fourier transformation spectroscopy.

The optical distance difference OPDr is determined by the lateral shear s, the available length bk of the raster detector, and the numerical aperture of the rotationally symmetric lens in the downstream anamorphic lens.

At the output of the cyclical double beam interferometer, the image translation v1 in the depth axis for the partial beam TB1 is then equal to the image shift v2 for the partial beam TB2, thus creating a compensation of the image shift in the depth axis. This is the condition for generating cylindrical waves with a respectively straight peak line on the raster detector, which are brought to interference there. This is a condition for generating spatial interferograms that are predominantly free of nonlinearities.

The image shift v1 is $$v1 = h1(n1-1)/n1 \quad \text{Equation (4)}$$

and the image shift v2 is $$v2 = h2(n2-1)/n2. \quad \text{Equation (5)}$$

The resulting optical distance difference OPD_zykaP is then an equal to zero, the value of which is determined with the already specified equation (3).

The different dispersion in the materials of the two plane parallel plates can be algorithmically canceled out with respect to falsifying influences by a phase correction when calculating spectrums. In this case, at least for the VIS and the NIR spectral range, the different dispersions can also be minimized by selecting the refractive materials both with respect to their refractive indexes and also with respect to their dispersions. In a double beam interferometer, not compensated dispersions ultimately generate the well-known chirping in spatial interferograms. However, by employing phase correction algorithms known from the prior art, this chirping largely has no influence on the calculated spectrum.

Furthermore, in a cyclical double beam interferometer for Fourier transformation spectroscopy, in the region Z, where no spatial overlap occurs between the two partial beams TB1 and TB2, an optical carrier plate of thickness h1 and with the refractive index n1 or a carrier plate of thickness h2 and the refractive index n2 is preferably mapped to the first and also to the second plane parallel plate. In this case, respectively one double gap aperture with two gap openings is positioned between the carrier plate and both the first and also the second plane parallel plate. If the optical carrier plate is formed with the thickness h2, which here represents the optical material with the higher refractive index, the carrier plate can be formed slightly thinner, which brings design advantages. In standard cases, the carrier plate is made of the optical material with the lower refractive index. The cost-effective Borkron Standard Glass BK7 can then be used as the optical material. However, two individual gap openings can preferably also be arranged in place of the double gap aperture.

Furthermore, in a double beam interferometer for Fourier transformation spectroscopy, the beam splitter is preferably formed with a polarizing beam splitter layer. Polarized light then leaves the beam splitter vertically and in parallel to the direction of incidence, and reaches both sides of the transmissive liquid crystal display. Following transmission of the latter, the polarization direction is rotated by 90 degrees in the addressed regions of the latter. Initially upon entering the cyclical interferometer on the polarization-optical beam splitter: reflected light is now transmitted. These relationships are widely known to persons skilled in the art. For the far infrared spectral range, the beam splitter can preferably also be formed as an arrangement with a fine, flat wire lattice surface.

Furthermore, a polarization analyzer is preferably arranged downstream of the double beam interferometer for Fourier transformation spectroscopy. The double beam interferometer is in this case preferably formed as a cyclical double beam interferometer. But the double beam interferometer can preferably also be formed as a Michelson-Type Interferometer or as a Mach-Zehnder Interferometer. A polarization analyzer is in this case generally arranged in combination with at least one other polarization-optical component, such as a beam splitter with a polarizing beam splitter layer. These relationships are widely known to persons skilled in the art.

Furthermore, the measured object for Fourier transformation spectroscopy is preferably mapped to a light source for illuminating the measured object, and said light source is formed with at least one luminescent field in the form of at least a single, preferably narrow light stripe. This illumination by means of a stripe is preferably used in a cyclical interferometer, because it is necessary to ensure that every pass-through area of a field of view discriminator is only illuminated by light in one revolving direction. When light in one revolving direction interferes with the second, generally immediately adjacent field of view discriminator in the cyclical interferometer, double beam interference is no longer created, which would render signal analysis significantly more difficult or entirely impossible. By contrast, the risk of interference does not apply in a Michelson-Type Interferometer and in a Mach-Zehnder Interferometer because the field of view discriminators are arranged in the two separated arms of the interferometer and are therefore discreetly separated. In a Michelson-Type Interferometer and in a Mach-Zehnder Interferometer, illumination by means of a light stripe is primarily intended to make effective use of light energy, but also to avoid undesirable light reflexes and scattered light. In order to obtain defined conditions for the lateral resolution of the measured object, it makes sense when the light stripe in this case fully covers the pass-through area of a field of view discriminator. The pass-through area of a field of view discriminator can be an opening with a gap shape and/or also a narrow, highly reflective area. The light source can also be formed as a flash source, which is particularly advantageous for moving scenes.

Furthermore, the measured object for Fourier transformation spectroscopy is preferably mapped to a light source for structured illumination of the measured object. In coordination with forming the field of view discriminators, the structured illumination of the measured object can take on an arbitrary pattern, preferably also in the form of a pattern with fine light spots on the measured object. This structured manner of object illumination with subsequent discrimination is known from confocal technology. In a double beam interferometer, the field of view discriminators then act as confocal discriminators in the space of the measured object, given the corresponding lateral structuring of said field of view discriminators with respect to the light pattern and given the corresponding focal range of the depth of field of the depicted light pattern. This is done by taking into account the rendering scale of the optics upstream of the double beam interferometer. Furthermore, means to shift the measured object and/or the measurement head are preferably arranged such that the measured object can be scanned spatially resolved in the depth axis with a relative movement to the measurement head, in order to then be spectrally analyzed.

Furthermore, preferably, the light source is in this case preferably formed as a computer-controllable, raster light source. The latter then has computer-controllable luminescent pixels. This light source is in this case preferably rendered by an OLED. This provides very high flexibility for illuminating the pass-through area of a field of view discriminator. As a result, incorrect positions of the field of view discriminators can then also be compensated. In this case, the computer-controllable, raster light source can preferably also be formed to interact with a spatial light modulator, preferably in the form of a computer-controllable micro-mirror array and/or a computer-controllable liquid crystal display. The measured object can preferably be illuminated with a fine pattern of light spots. In a double beam interferometer, the field of view discriminators then act as confocal discriminators in the space of the measured object, given the corresponding lateral structuring of said field of view discriminators as spatial light modulators with respect to the light pattern by means of a computer-controllable, raster light source and given the corresponding focal range of the depth of field of the depicted light pattern. The confocal approach can be used based on a relative movement of the measured object to the measurement head in the depth axis.

Furthermore, a compensation plate tilted, and at least approximately plane parallel to the beam splitter surface of a plate beam splitter, which is formed with at least one plane parallel plate, is preferably arranged upstream of the double-beam interferometer for Fourier transformation spectroscopy. The plate beam splitter is generally formed with two plane parallel plates. The compensation plate tilted toward the plate beam splitter is designed to avoid rendering errors, such as astigmatism and coma for generating images in the double beam interferometer. The compensation plate is in this case oriented such that an angle of the same value, but opposing direction, is created The plate thickness of said compensation plate arranged upstream of the double beam interferometer is equivalent to the at least approximately plane parallel beam splitter plate, or equal to the sum of the thicknesses of the two plates when using a plate beam splitter with compensation plate. For the upstream compensation plate, the same substrate material must be used that was also used for the beam splitter plate and/or the beam splitter plate pair. Due to the resulting effective plate thickness in the beam path, only an opening error then remains that can be corrected in the upstream lens.

Furthermore, a compensation plate tilted, and at least approximately plane parallel to the beam splitter surface of a plate beam splitter, which is formed with at least one plane parallel plate, is preferably arranged downstream of the double-beam interferometer for Fourier transformation spectroscopy. The plate beam splitter is generally however formed with two plane parallel plates. The compensation plate tilted toward the plate beam splitter is designed to avoid wave front deformations when detecting the interfering wavefronts. Here as well, the following applies analogously: The plate thickness of the compensation plate arranged downstream of the double beam interferometer is equivalent to the beam splitter plate, or equal to the sum of the thicknesses of the two plates when using a plate beam splitter with compensation plate. For the downstream compensation plate, the same substrate material must be used that was also used for the beam splitter plate and/or the beam splitter plate pair. Due to the resulting effective plate thickness in the beam path, only an opening error then remains that can be corrected in the downstream lens. The double beam interferometer can in this case be formed as a Michelson-Type Interferometer, as a Mach-Zehnder Interferometer, or also as a cyclical interferometer with two plane mirrors and/or plane mirror surfaces in the revolving beam path. In a Mach-Zehnder Interferometer, the plane parallel plates of a plate beam splitter are preferably arranged next to each other in planes parallel to each other, wherein a Mach-Zehnder Interferometer then has two splitter surfaces, one for beam splitting and one for beam reunification.

Furthermore, respectively one compensation plate tilted, and at least approximately plane parallel to the beam splitter surface of a plate beam splitter, which is formed with at least one plane parallel plate, is preferably arranged in each interferometer arm of the double-beam interferometer for Fourier transformation spectroscopy. When a plate beam splitter is functionally used to unite partial beams, as for example in a Mach-Zehnder Interferometer, this case is nevertheless referred to as a plate beam splitter.

Furthermore, in a double beam interferometer for Fourier transformation spectroscopy, the two tilted, at least approximately plane parallel compensation plates are preferably arranged in planes parallel to each other. This allows the thickness of all at least approximately plane parallel compensation plates to be equal. It is in this case also possible that the two plane parallel compensation plates in a Mach-Zehnder Interferometer are replaced by a single compensation plate of corresponding length with two pass-through areas for the beam. This can simplify the adjustment of the Mach-Zehnder Interferometer.

Furthermore, in a double beam interferometer for Fourier transformation spectroscopy, the optical distances in refractive, transparent material of the same type are preferably at least approximately made the same from the beam splitting up to the field of view discriminators BFD1 and BFD2 in the two arms of the double beam interferometer for the main beams HB of the partial beams TB1 and TB2. This is generally a solid, at least partially transparent optical material in the double beam interferometer, but a liquid and at least partially transparent optical material can also be used.

Furthermore, in a cyclical double beam interferometer for Fourier transformation spectroscopy, the optical distances (OPLB_1, OPLB_2) in refractive, transparent material of the same type at least approximately meet one of the following equations from the beam splitting up to the field of view discriminators (BFD1, BFD2) in the two arms of the double beam interferometer for the main beams of the partial beams (TB1, TB2):

$$AB+BC=AT+TE+EG, \quad \text{Equation (6)}$$

$$TB+BC=TE+EG, \quad \text{Equation (7)}$$

$$HB+BC=JE+EG. \quad \text{Equation (8)}$$

The paths AB, BC, AT, TE, TB, BC, EG, as well as HB and JE in this case each represent optical distances in refractive, transparent material of the same type. The heights h1 and h2 are made equivalent on mirror prisms with the same angles. This ensures that a double gap aperture and/or a liquid crystal display can be inserted vertically in relation to the axes of the main beams of the two partial beams in a cyclical double beam interferometer at least approximately on half the revolving optical path. The aberrations in the beam path in this case represent a chromatic opening error created by using periscope prisms with a vertical axis beam entry and beam exit with the effect of a thick plane parallel plate. These aberrations are then equal in the two opposingly revolving beam paths, and can therefore be corrected with upstream and downstream lenses, that also compensate chromatic opening errors. The compensation of the chromatic opening error permits the interference of waves with nearly ideal cylindrical wave form, which minimizes the highly undesirable nonlinearities in the spatial interferograms on the raster detector.

Furthermore, in a Michelson-Type Interferometer and/or in a Mach-Zehnder Interferometer, the use of refractive optical means preferably renders the difference of the optical image shift v1 and v2 in the depth axis and in the two arms IA1 and IA2 of the respective interferometer smaller than the wave optical depth of field focal range for the shortest wavelength calculated from the ratios of the shortest wavelength and the square of the numerical aperture determined by the aperture angle alpha_yz of the anamorphic lens arranged downstream of the Michelson-Type Interferometer and/or the Mach-Zehnder Interferometer. In this case, the optical distance difference OPD_zykaP between the two partial beams TB1 and TB2 at the output of the interferometer preferably has an order of magnitude value of one millimeter, when very high pixel count raster detectors in the VIS spectral range with an order of magnitude of 100 million pixels are used, as is already common in astronomical research.

This is designed to generate on the raster detector a two-sided spatial interferogram with a short, as conventionally rendered, left part in order to record with the largest possible optical distance difference on the right side of the interferogram. The location of the optical distance difference zero is therefore located in the proximity of the edge of the raster detector. This one-sidedness improves the spectral resolution, wherein a short-left piece of the spatial interferogram is typically necessary for the phase correction.

Furthermore, in a cyclical double beam interferometer, a plane plate group in region Z, where the two partial beams do not geometrically overlap, preferably renders the difference of the optical image shifts v1 and v2 in the depth axis smaller in the two revolving directions at the output of the interferometer than the wave optical depth of field focal range for the shortest wavelength determined by ratio of the shortest wavelength and the square of the numerical aperture determined from the aperture angle alpha of the anamorphic lens arranged downstream of the cyclical double beam interferometer, and wherein the optical distance difference OPD_zykaP in this case is up to one millimeter in the two partial beams TB1 and TB2. This is generally the aperture angle alpha in air. The introduction of an optical distance difference OPD_zykaP is designed to generate on the raster detector a two-sided spatial interferogram with a short, as conventionally rendered, left part in order to record with the largest possible optical distance difference on the right side of the interferogram. The location of the optical distance difference zero is therefore located in the proximity of the edge of the raster detector.

Furthermore, preferably two mirror prisms of equal construction are inserted in a cyclical double beam interferometer with a foil beam splitter and/or a wire lattice beam splitter for the midinfrared and/or far infrared range for Fourier transformation spectroscopy in the revolving beam path. Both of these are formed from the same refractive material, which for this spectral range is at least partially transparent, for example CaF2, KBr and/or ZnSe. These mirror prisms each comprise the acute half angle psi twice, respectively between the mirror surface and a nonreflective surface, which represent the entry and exit surface on a periscope prism. The same optical distances up to a field of view discriminator are then created for every revolving direction in the cyclical double beam interferometer. The field of view discriminator is positioned at half the optical distance in the revolution of the light in the cyclical double beam interferometer. On each of the two field of view discriminators, an in-focus image of the measured object can then be created, and a partial region of the image can be discriminated.

Furthermore, in a cyclical double beam interferometer, in the region Z, where no spatial overlap occurs between the two partial beam s TB1 and TB2, a plane parallel plate of thickness h1 and made of optical material with the refractive index n1 is preferably arranged in the partial beam TB1, and also a plane parallel plate of thickness h2 and made of optical material with the refractive index n2 is preferably arranged in the partial beam TB2. The thicknesses h1 and h2 are in this case determined based on the already specified equation (2). As a result, the respective image translation in the depth axis is equivalent in the two partial beams TB1 and TB2 at the output of the cyclical double beam interferometer, and the optical distance difference OPD_zykaP at the output of the cyclical double beam interferometer is determined by the already specified equation (3). The optical distance difference OPD_zykaP must be selected such that the inequality 0.1*OPDr<OPD_zykaP<0.9 OPDr is observed in this case.

The optical distance difference OPDr is determined by the lateral shear s, the used length bk of the raster detector, and the numerical aperture of the rotationally symmetric lens in the downstream anamorphic lens.

Here, the optical distance difference OPDr is the maximum achievable optical distance difference in the spatial interferogram on the edge of the raster detector, given a symmetric position of the spatial interferogram on the raster detector.

At the output of the cyclical double beam interferometer, the image translation v1 in the depth axis for the partial beam TB1 is then equal to the image shift v2 for the partial beam TB2, thus creating a compensation of the image shift in the depth axis. This is the condition for generating cylindrical waves with a straight peak line on the raster detector, and therefore for generating spatial interferograms rl without nonlinearities, and the optical distance difference OPD_zykaP at the output of the cyclical double beam interferometer is determined by the already specified equation (3).

Furthermore, in a double beam interferometer for Fourier transformation spectroscopy, the beam splitter for the far infrared range and/or the terahertz range is preferably formed as a fine wire lattice with a flat surface, with the wires arranged in parallel. This arrangement represents a polarizing beam splitter. But the double beam interferometer can preferably also be formed as a Michelson-Type interferometer and/or as a cyclical double beam interferometer. When a Mach-Zehnder Interferometer is used, two fine wire lattices are preferably used as beam splitters, one for beam splitting, and one for beam reunification

DESCRIPTION OF THE FIGURES

The following describes the details of several exemplary embodiments, wherein the invention is not restricted to the described exemplary embodiments. Individual features described in a particular embodiment can be arbitrarily combined, provided they do not exclude each other.

Moreover, various features provided together in the exemplary embodiments are not to be seen as restricting the invention.

Figure 3:
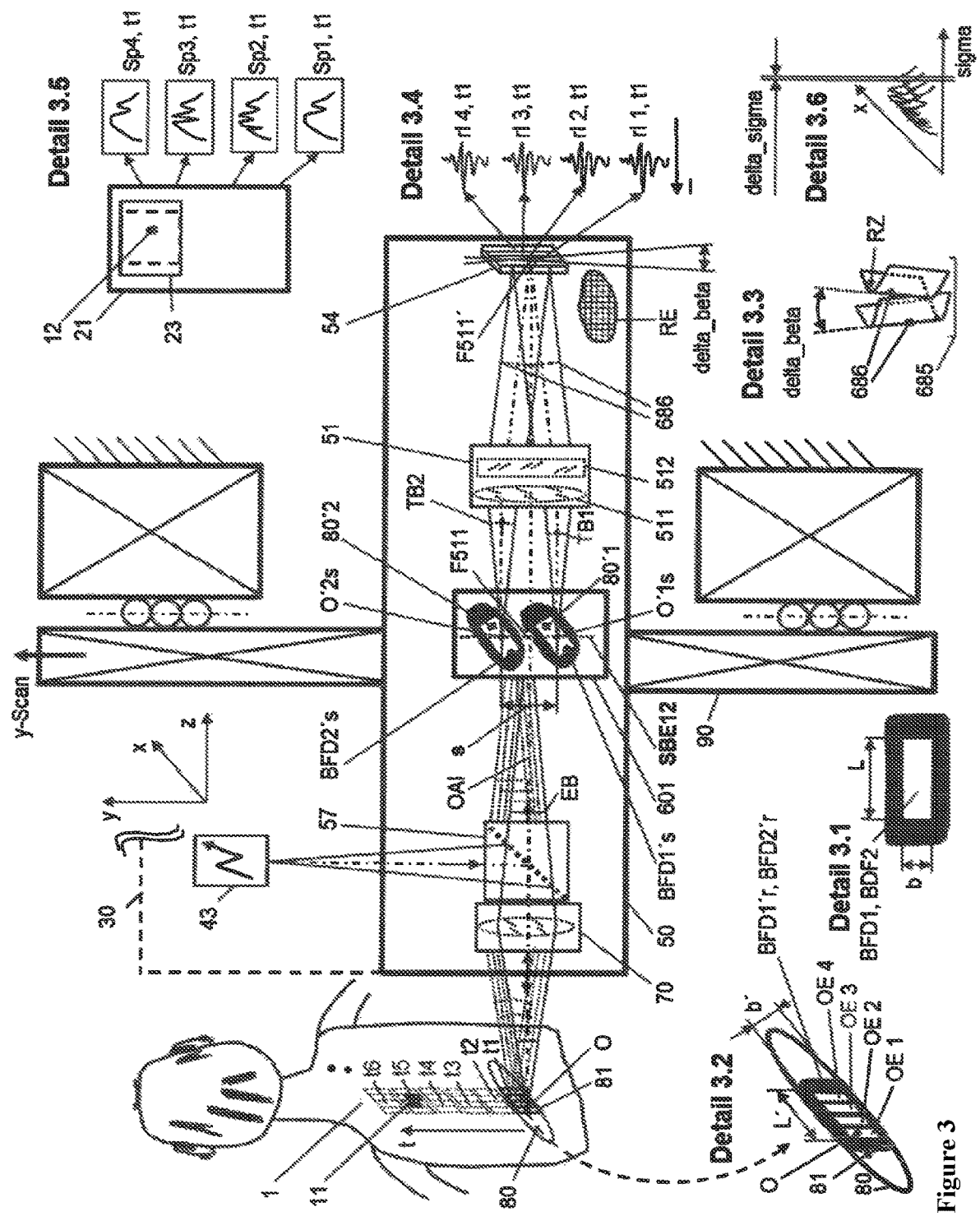
Figure 4:
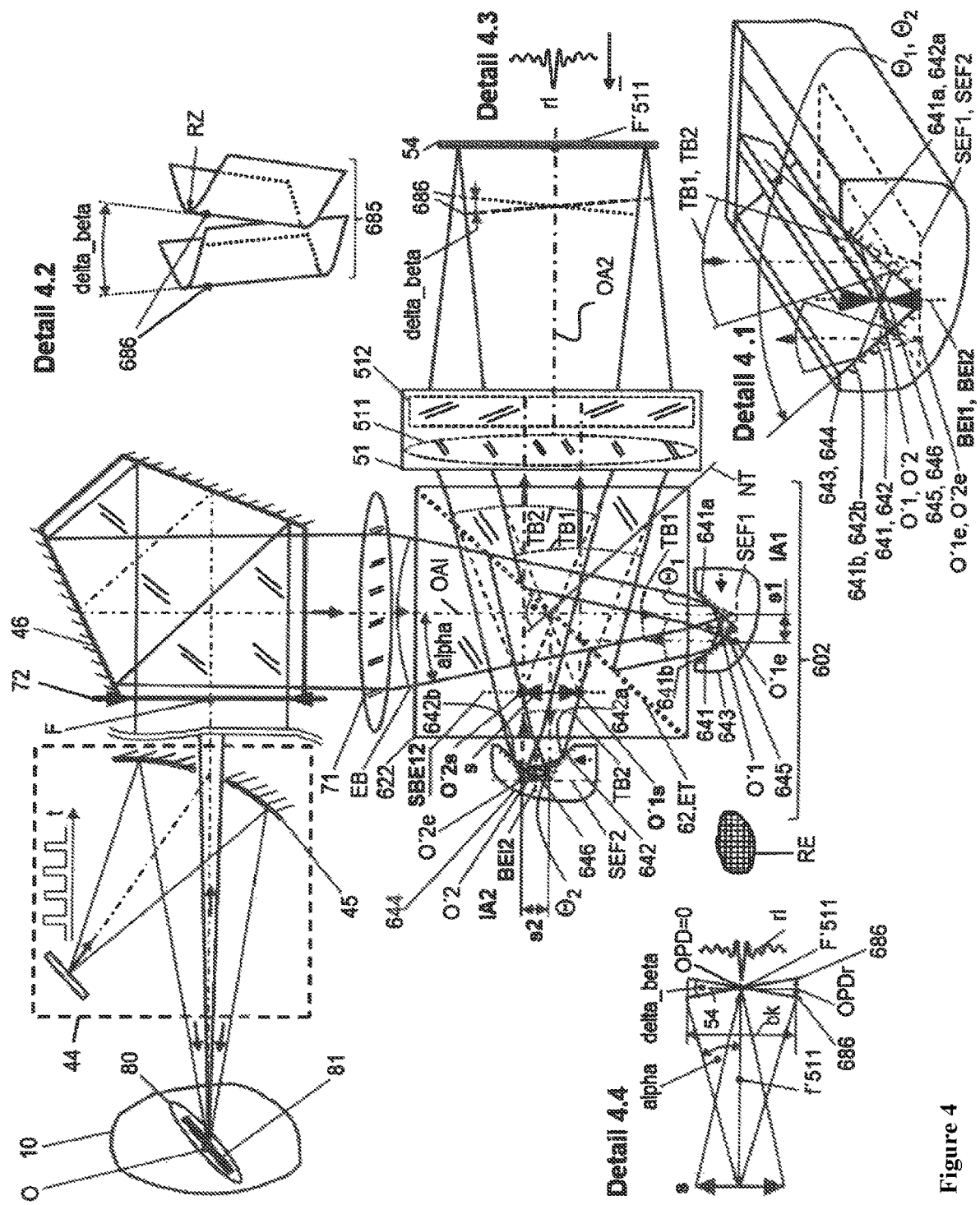
Figure 5:
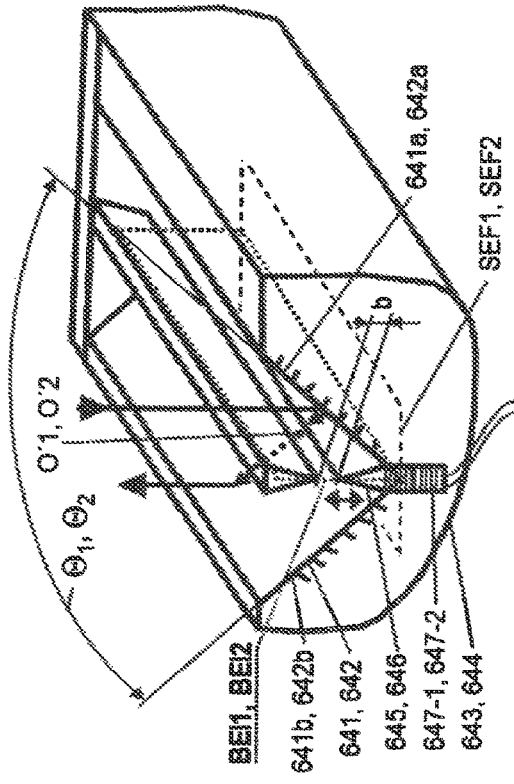
Figure 6:
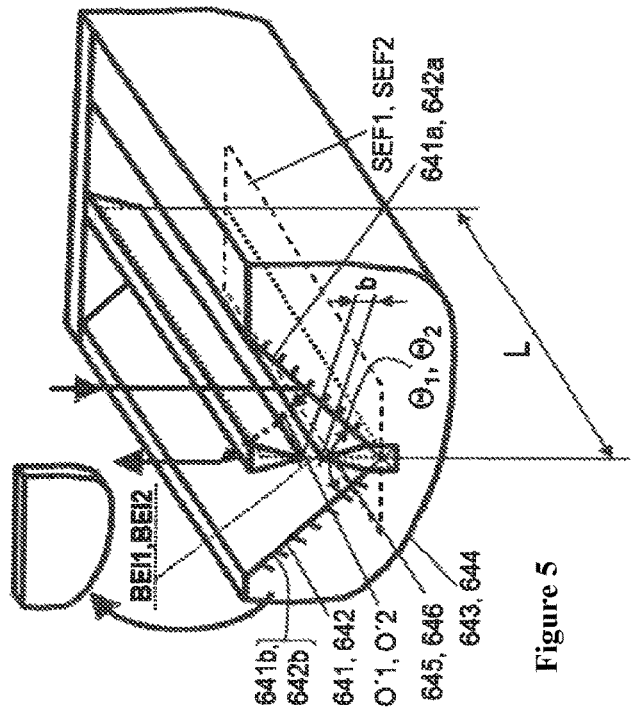
Figure 7:
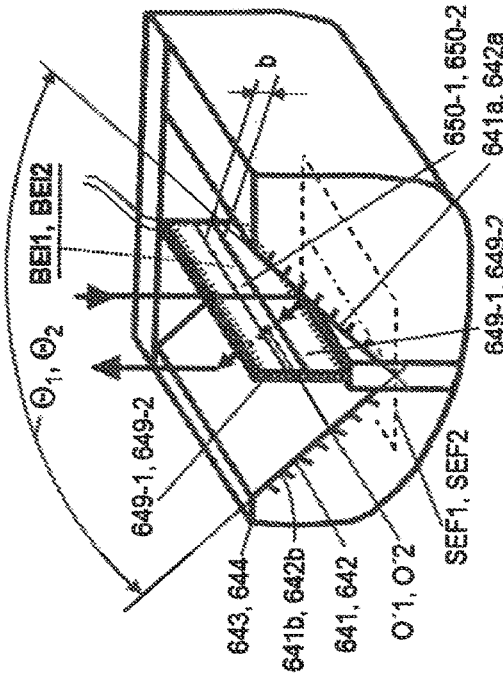
Figure 8:
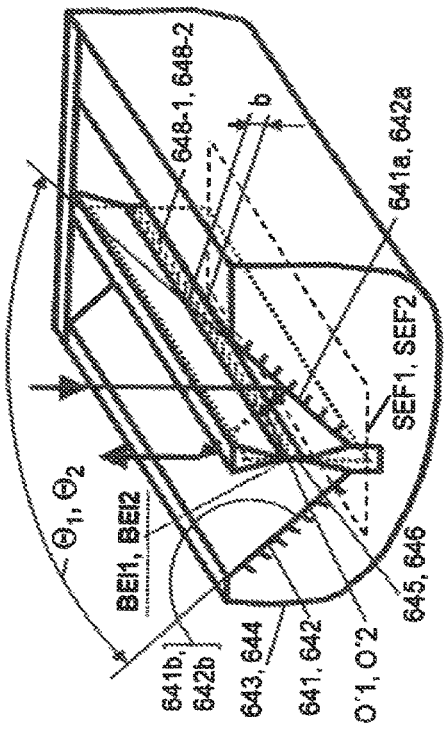
Figure 9:
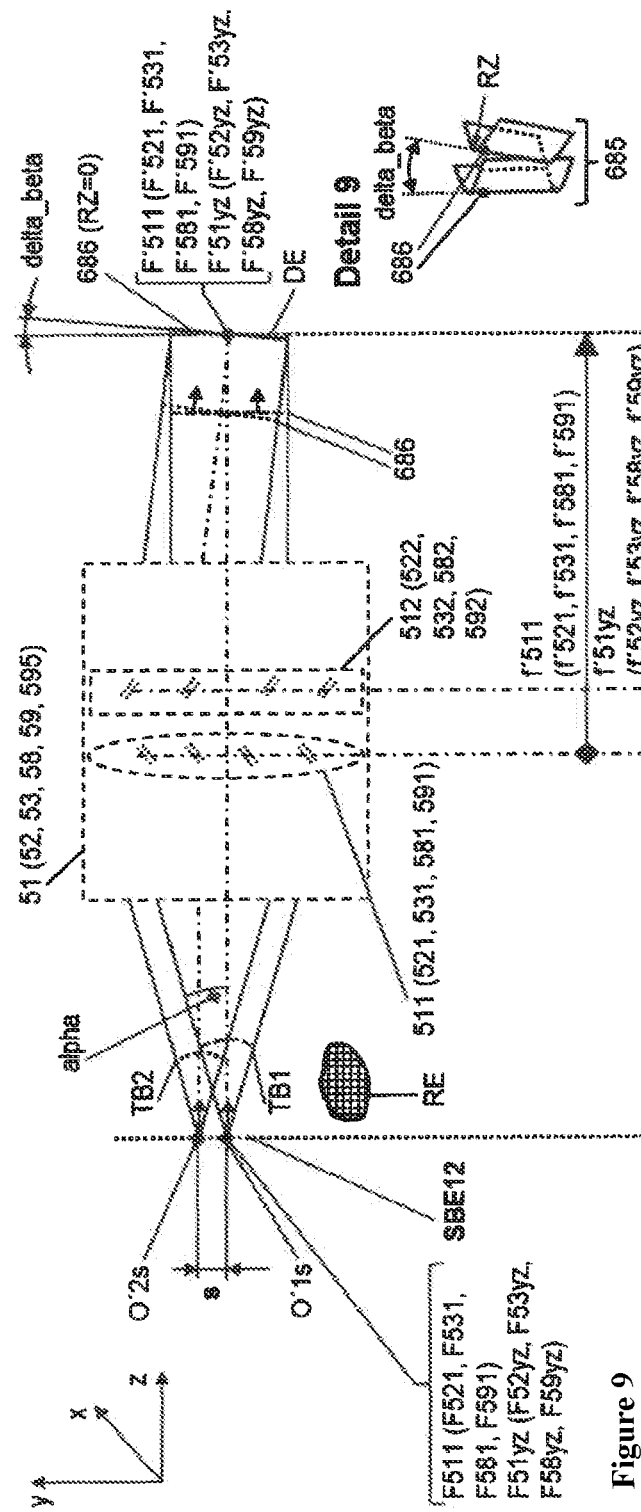
Figure 10:
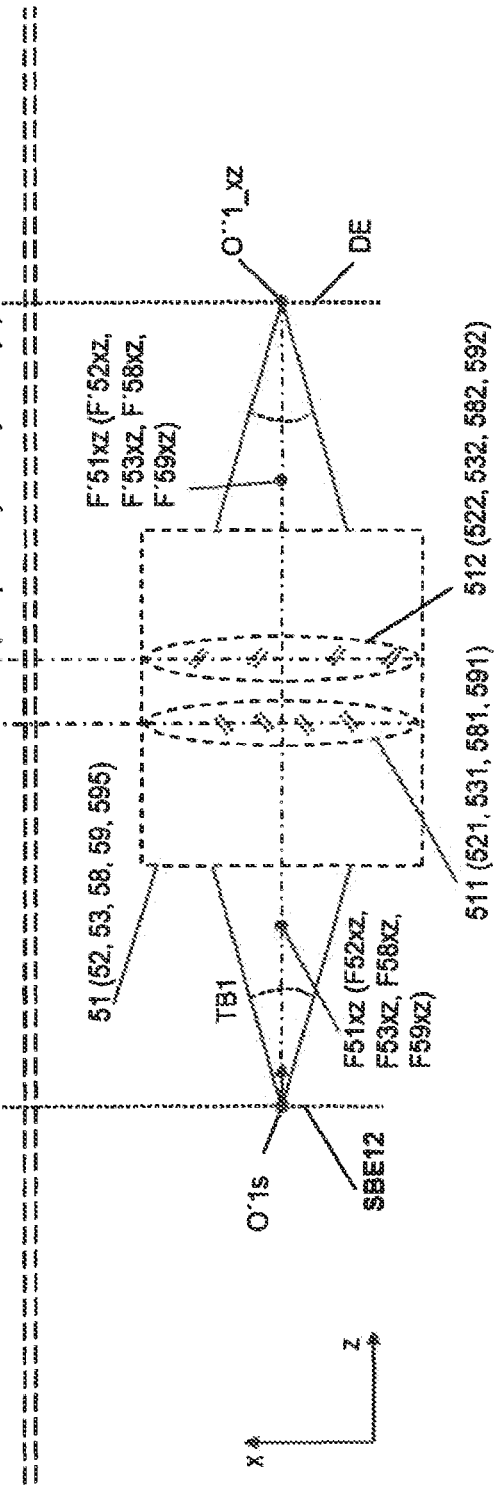
Figure 11:
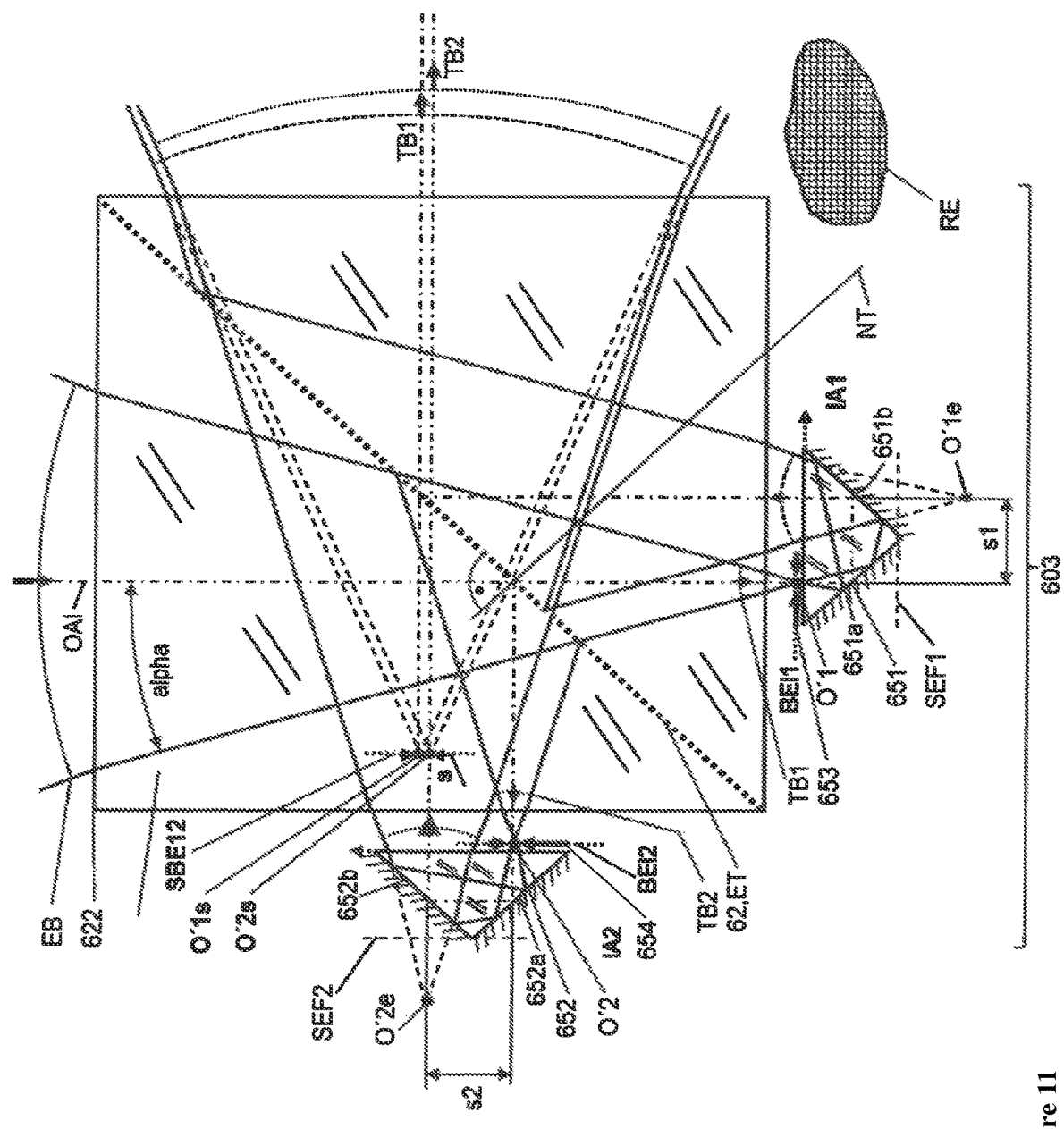
Figure 12:
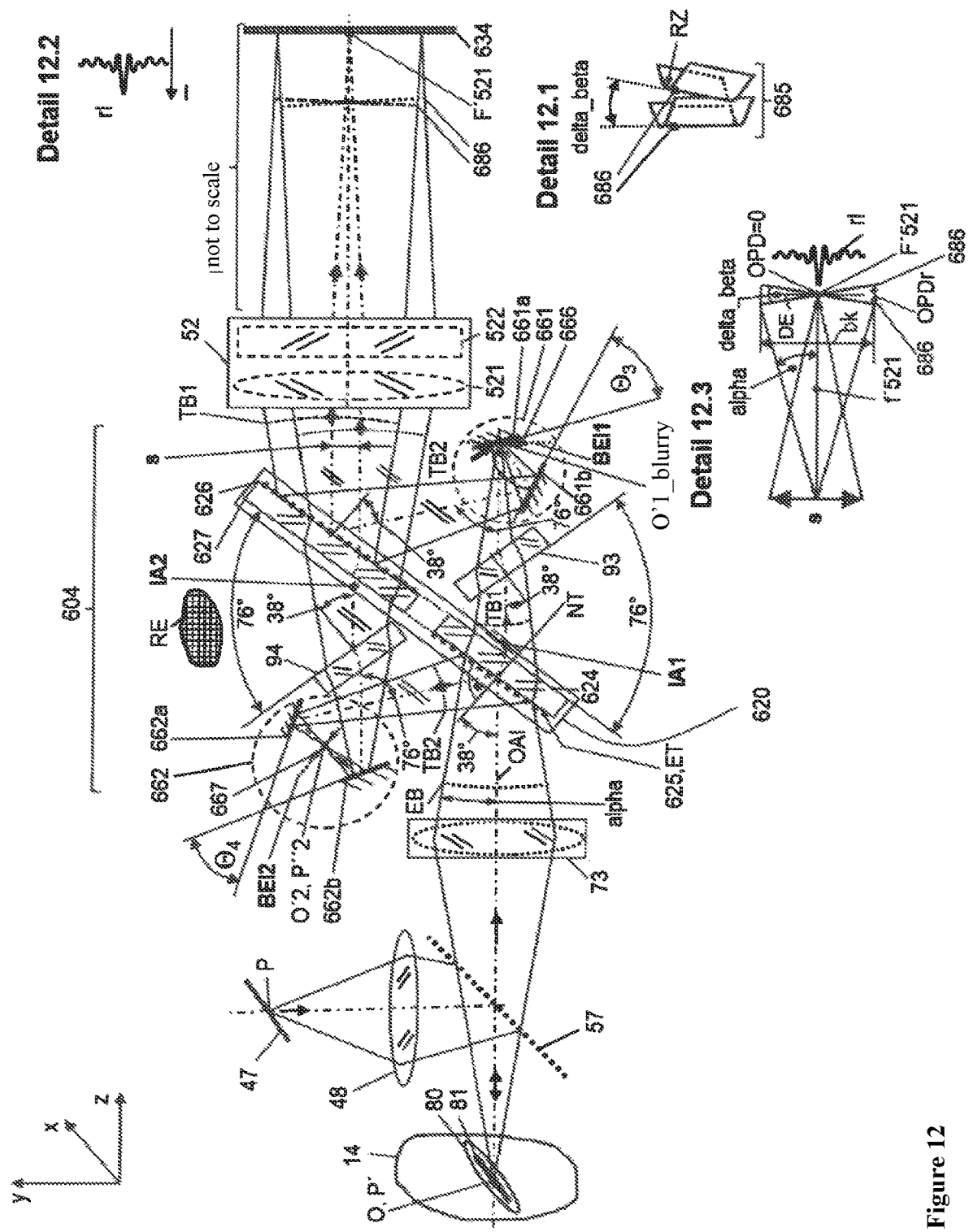
Figure 13:
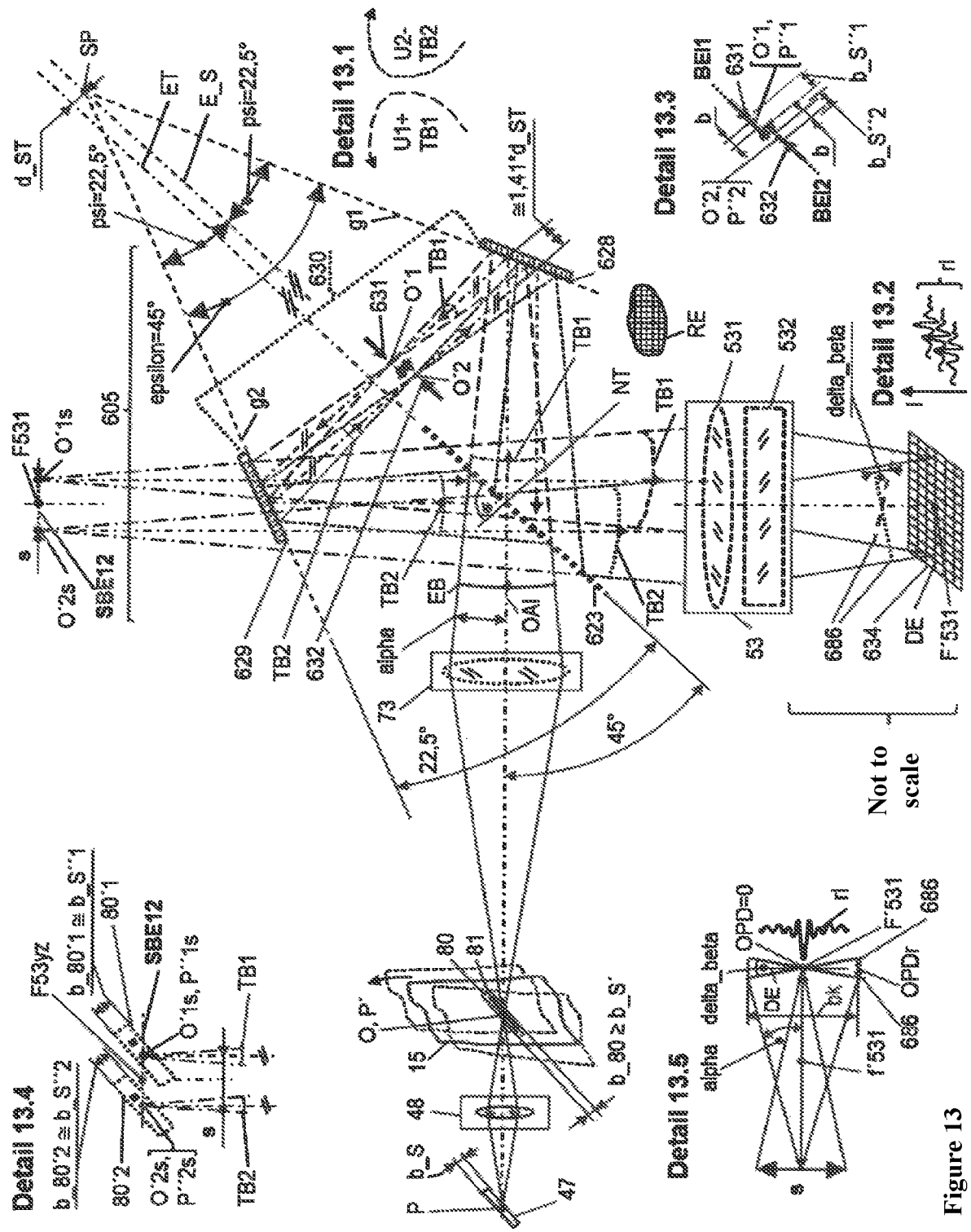
Figure 14:
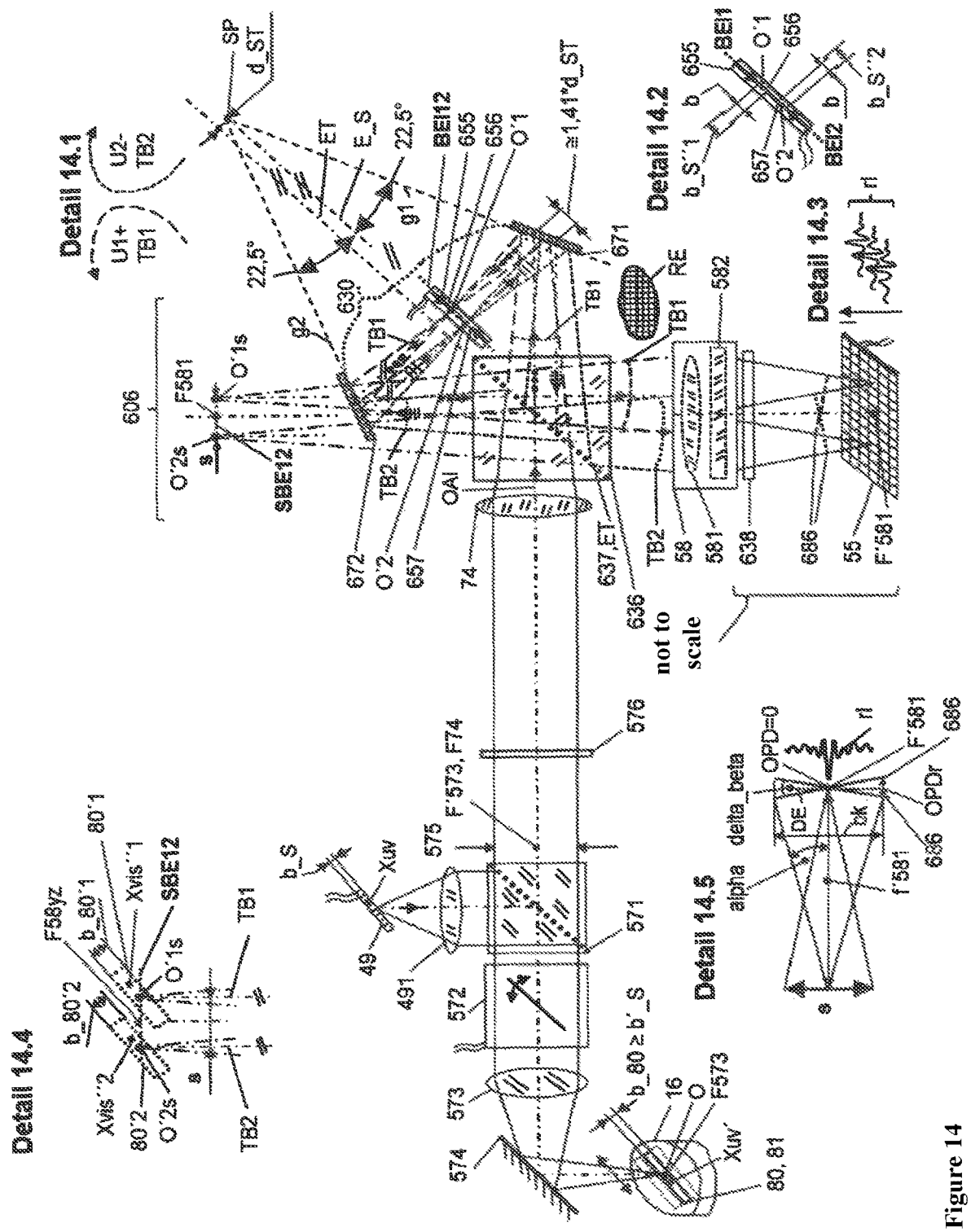
Figure 15:
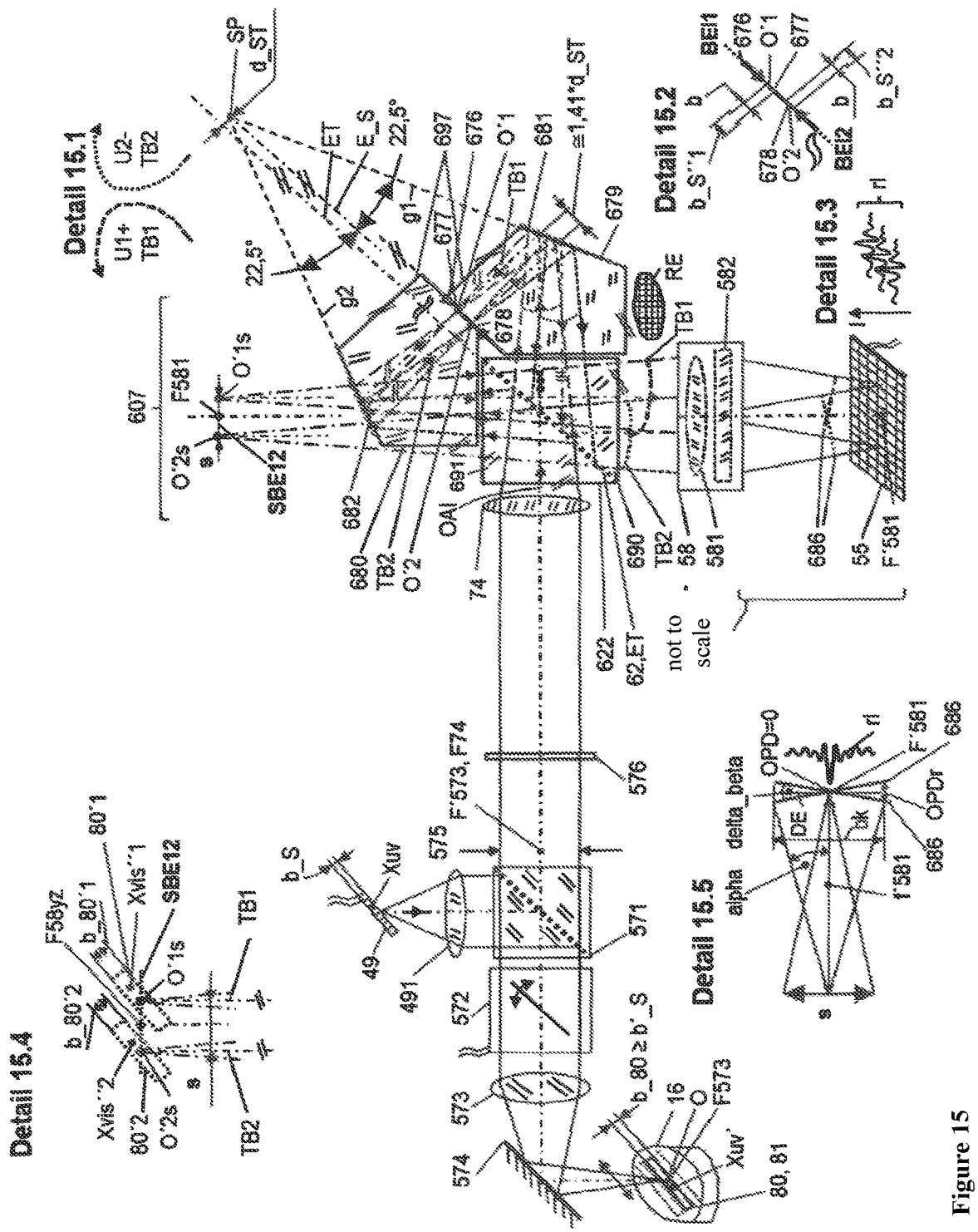
Figure 16:
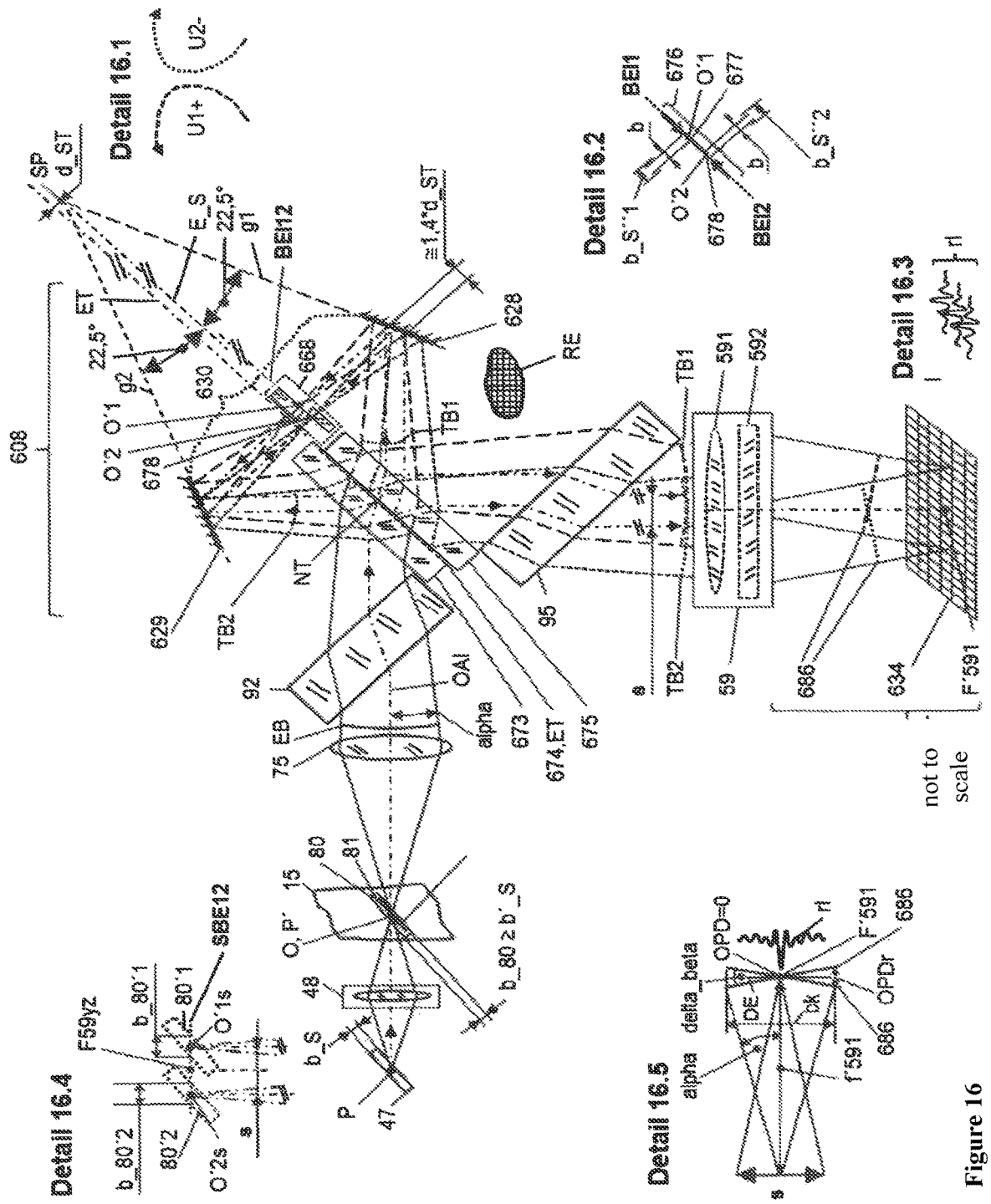
Figure 17:
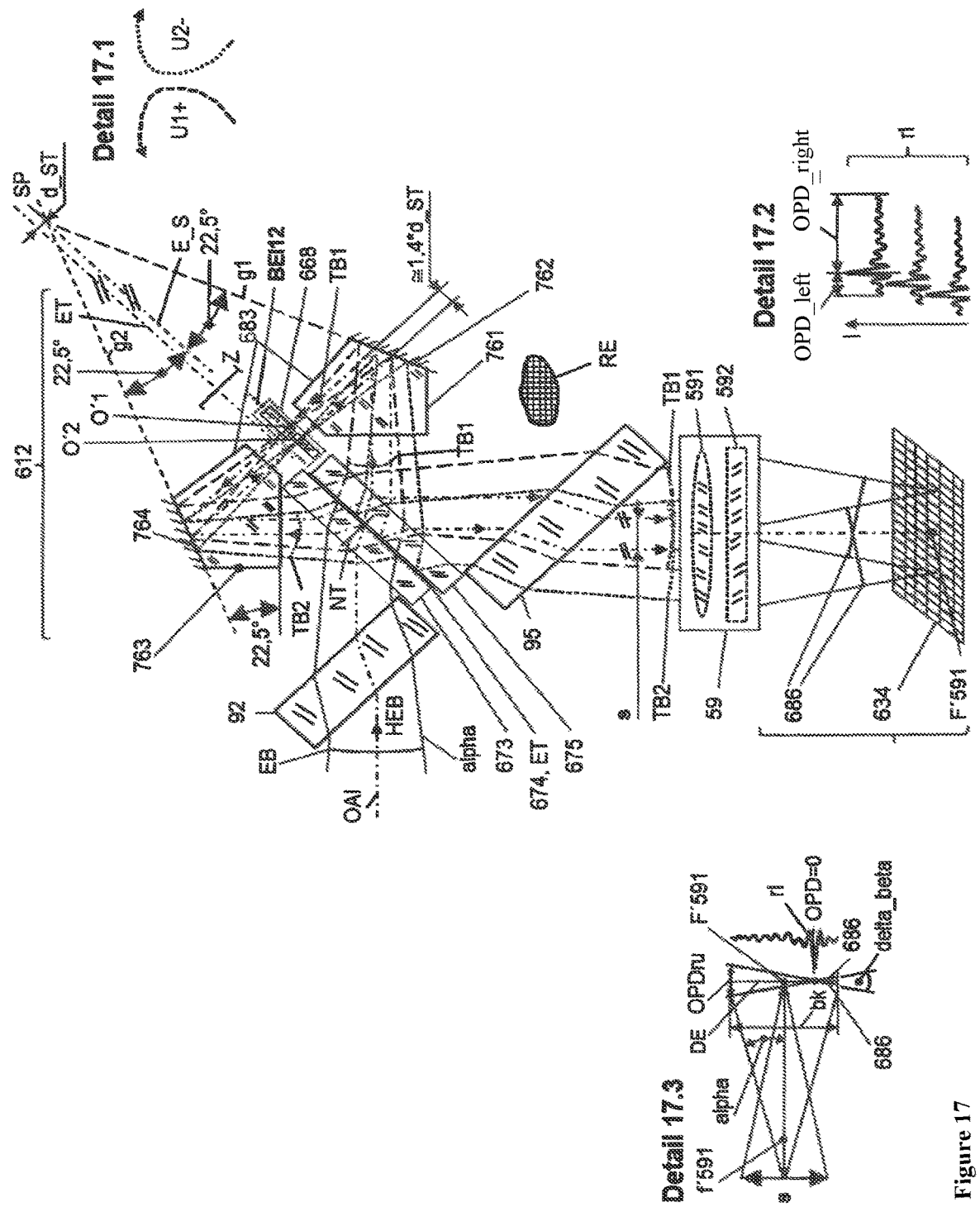
Figure 19A:
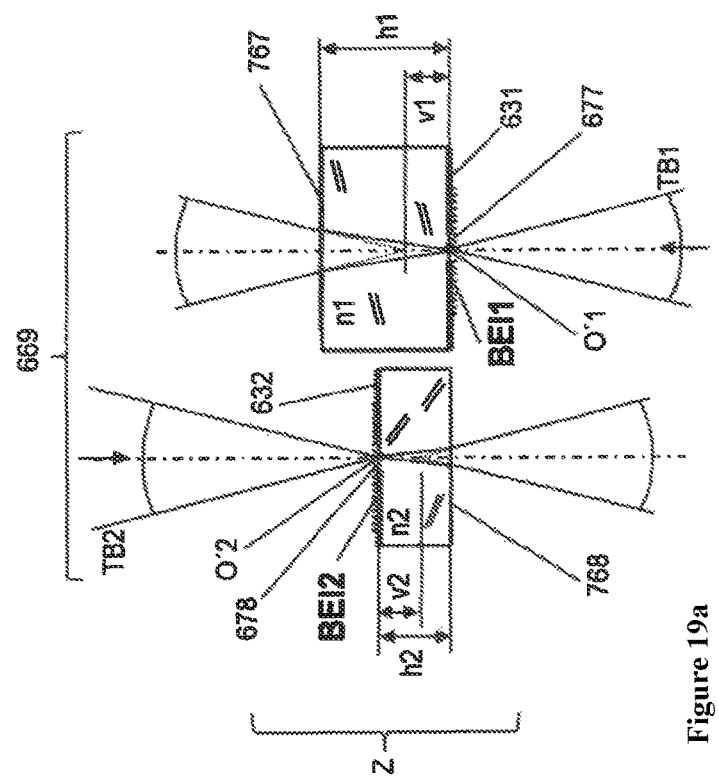
Figure 19B:
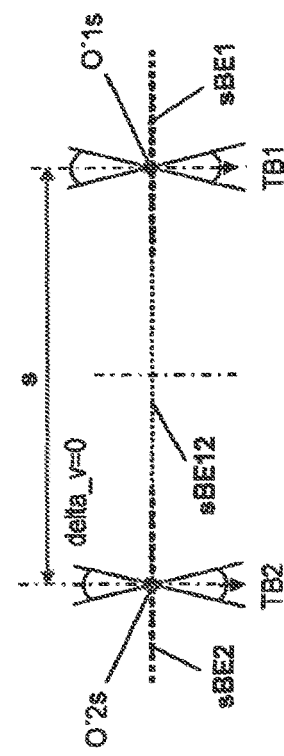
Figure 20:
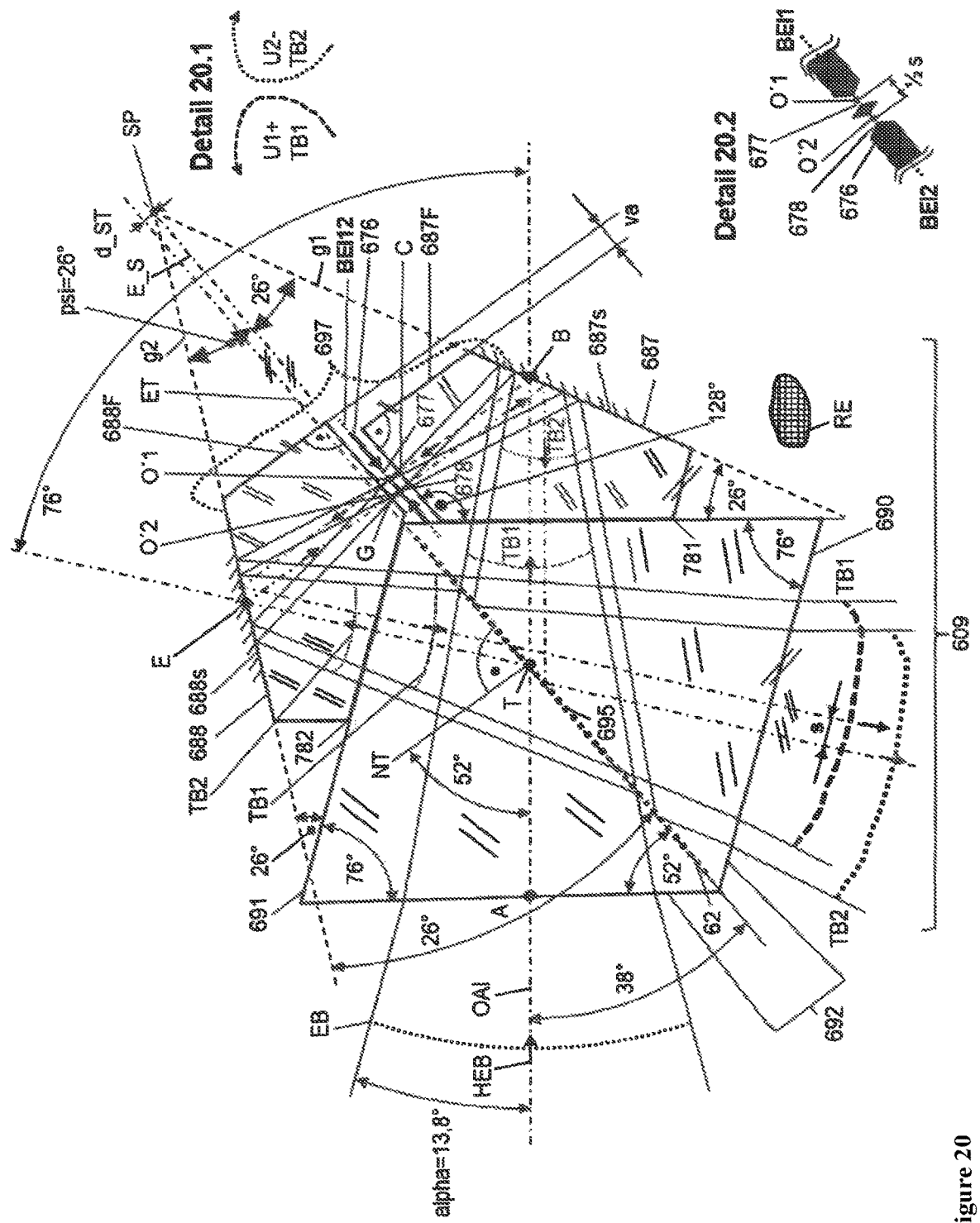
Figure 21:
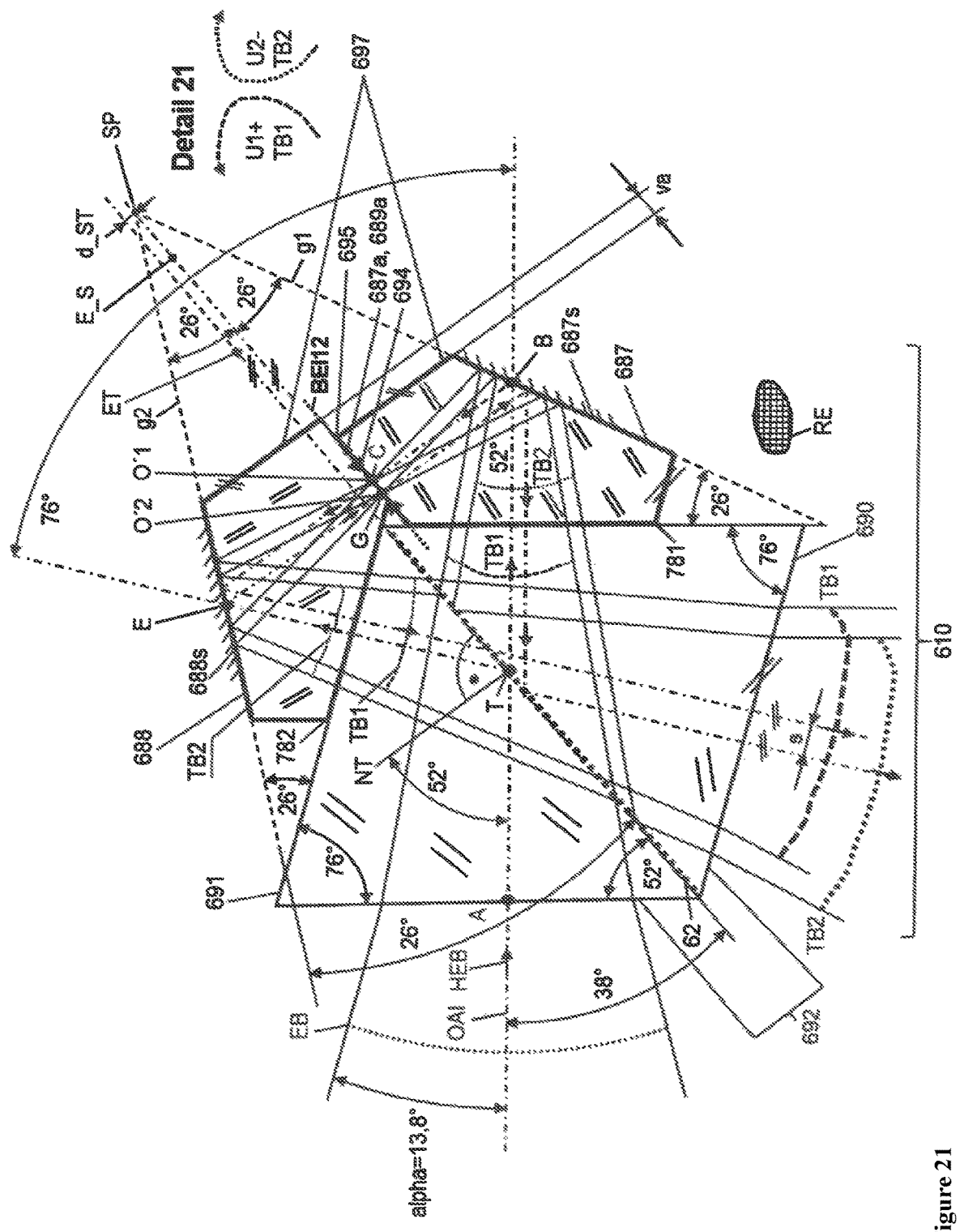
Figure 22:
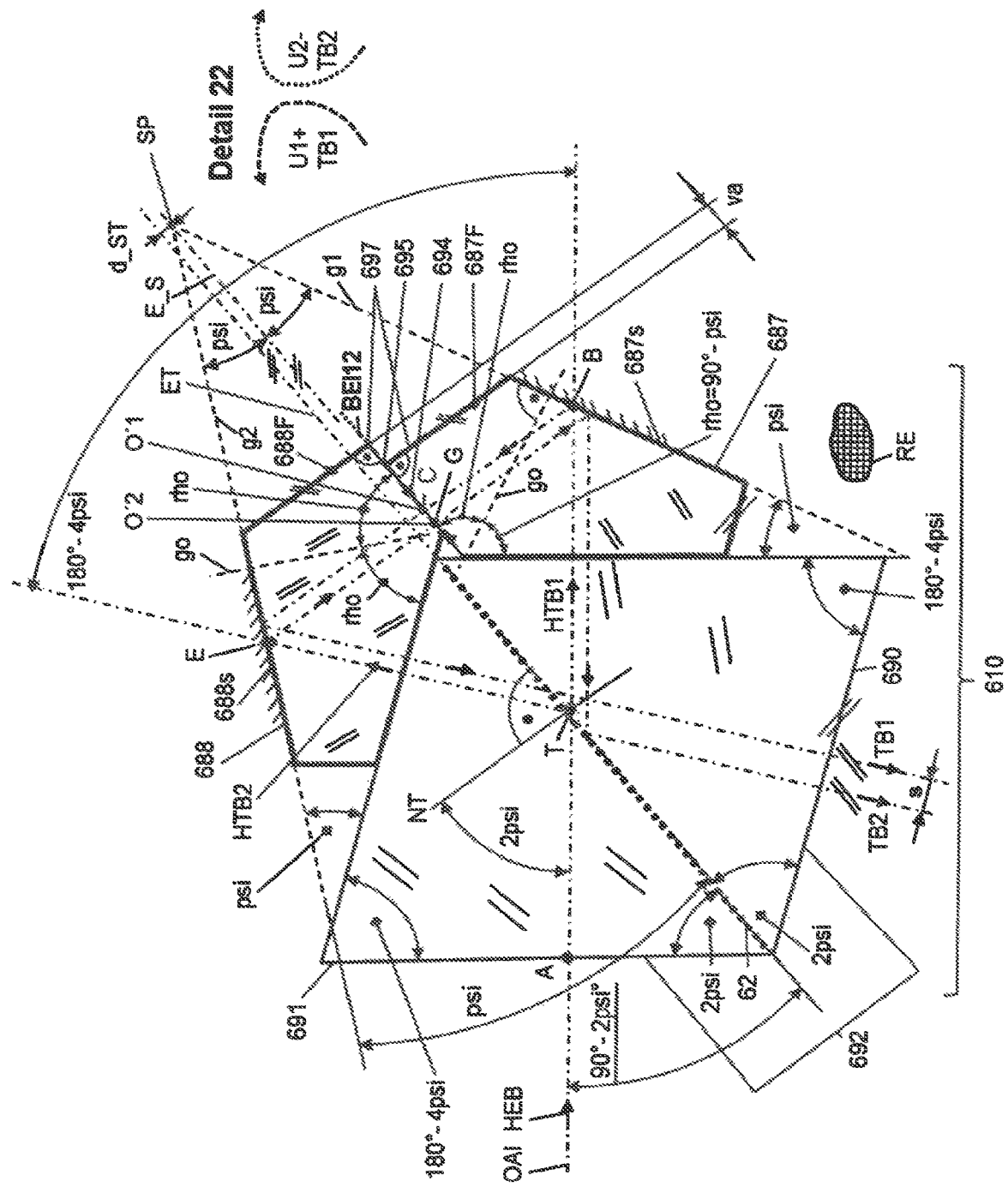
Figure 23:
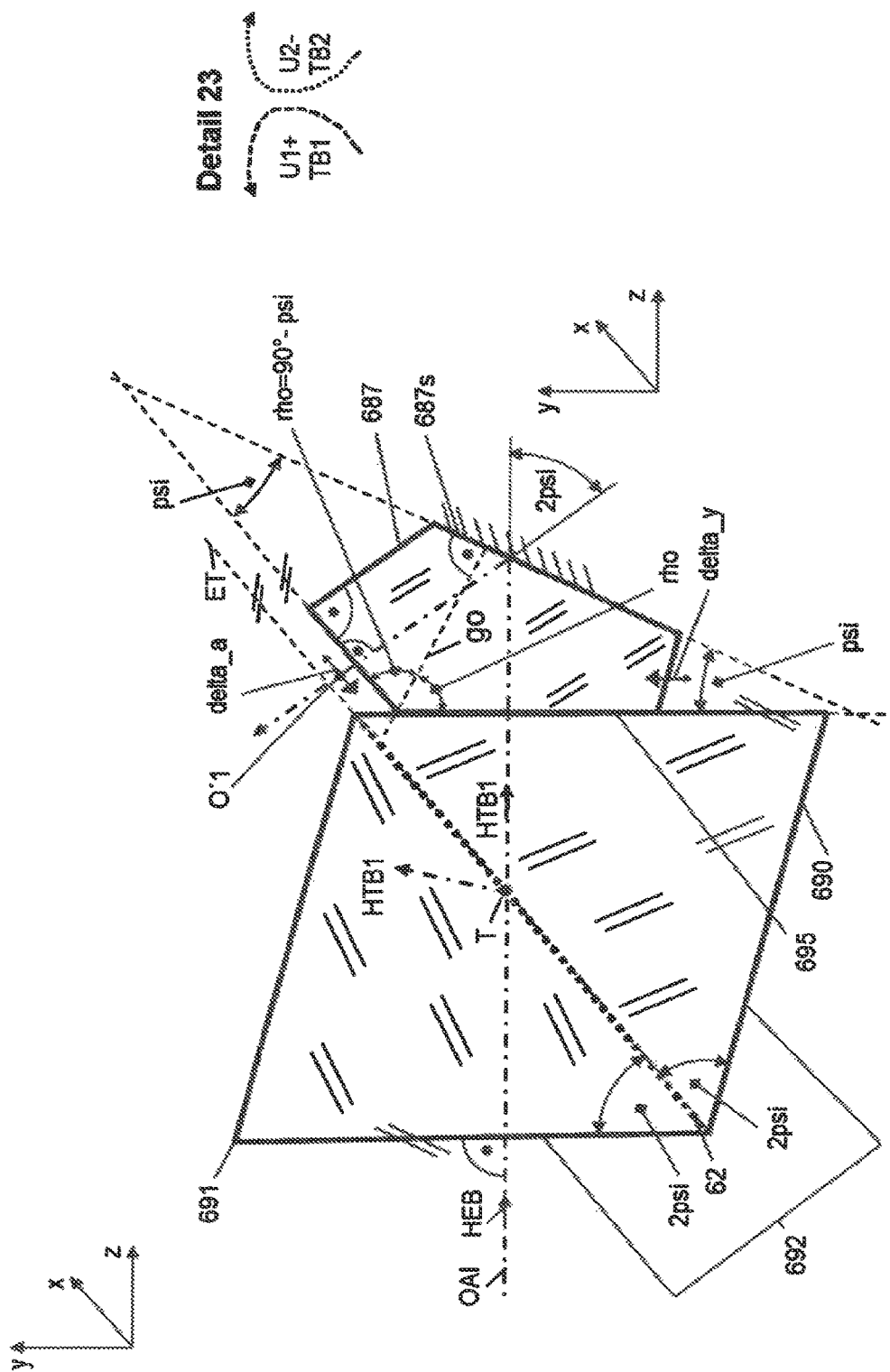
Figure 24:
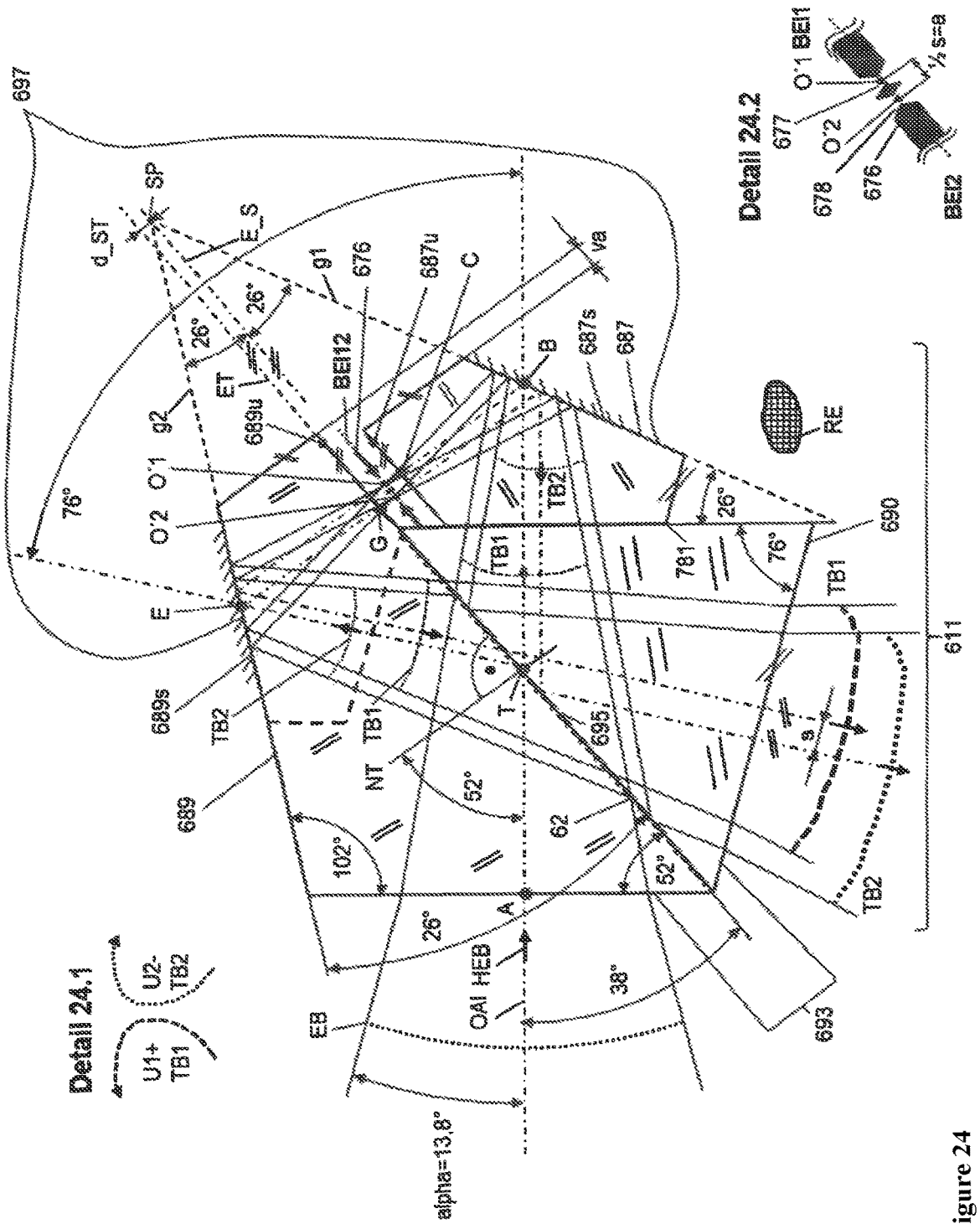
Figure 25:
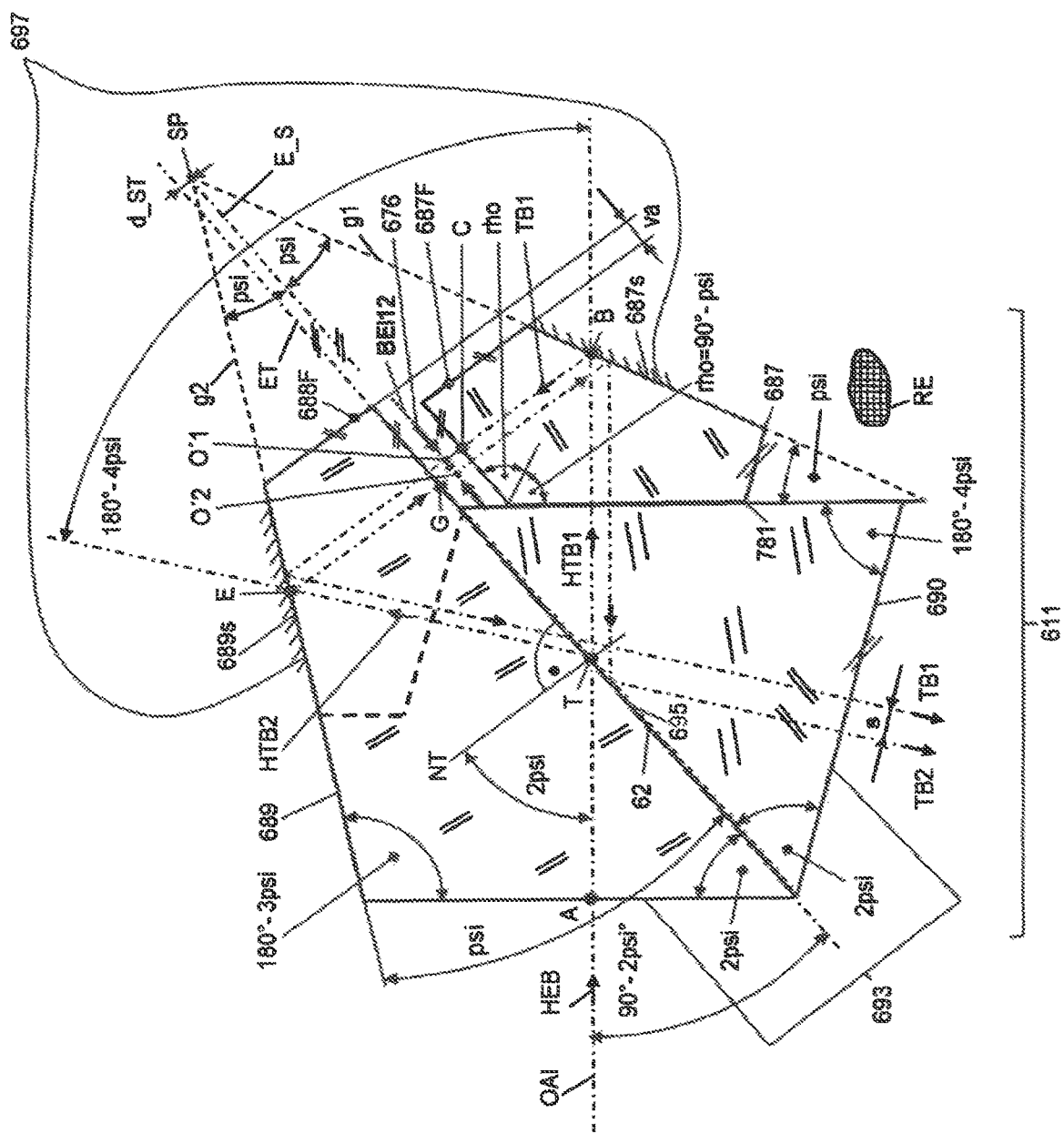
Figure 26:
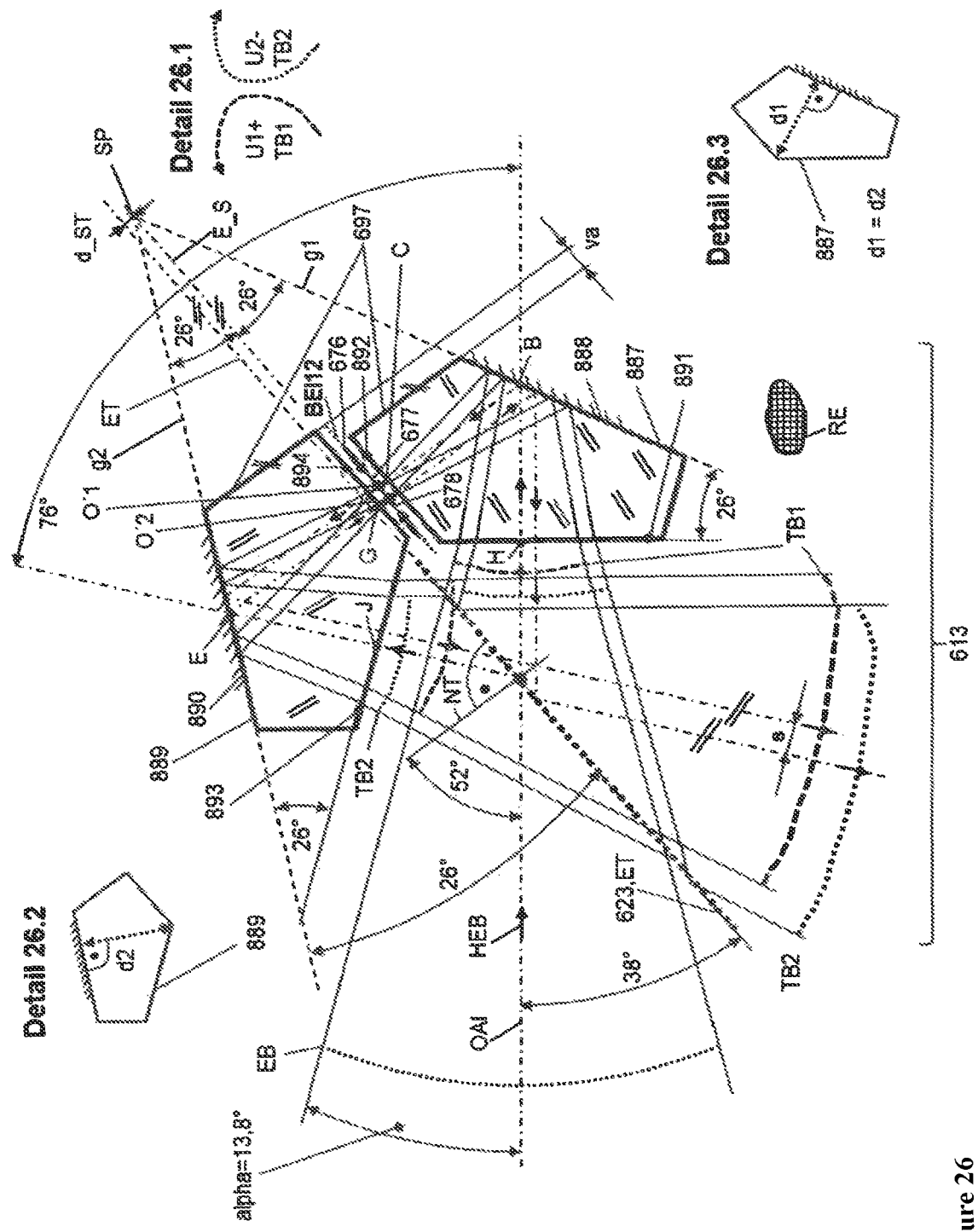
Figure 27:
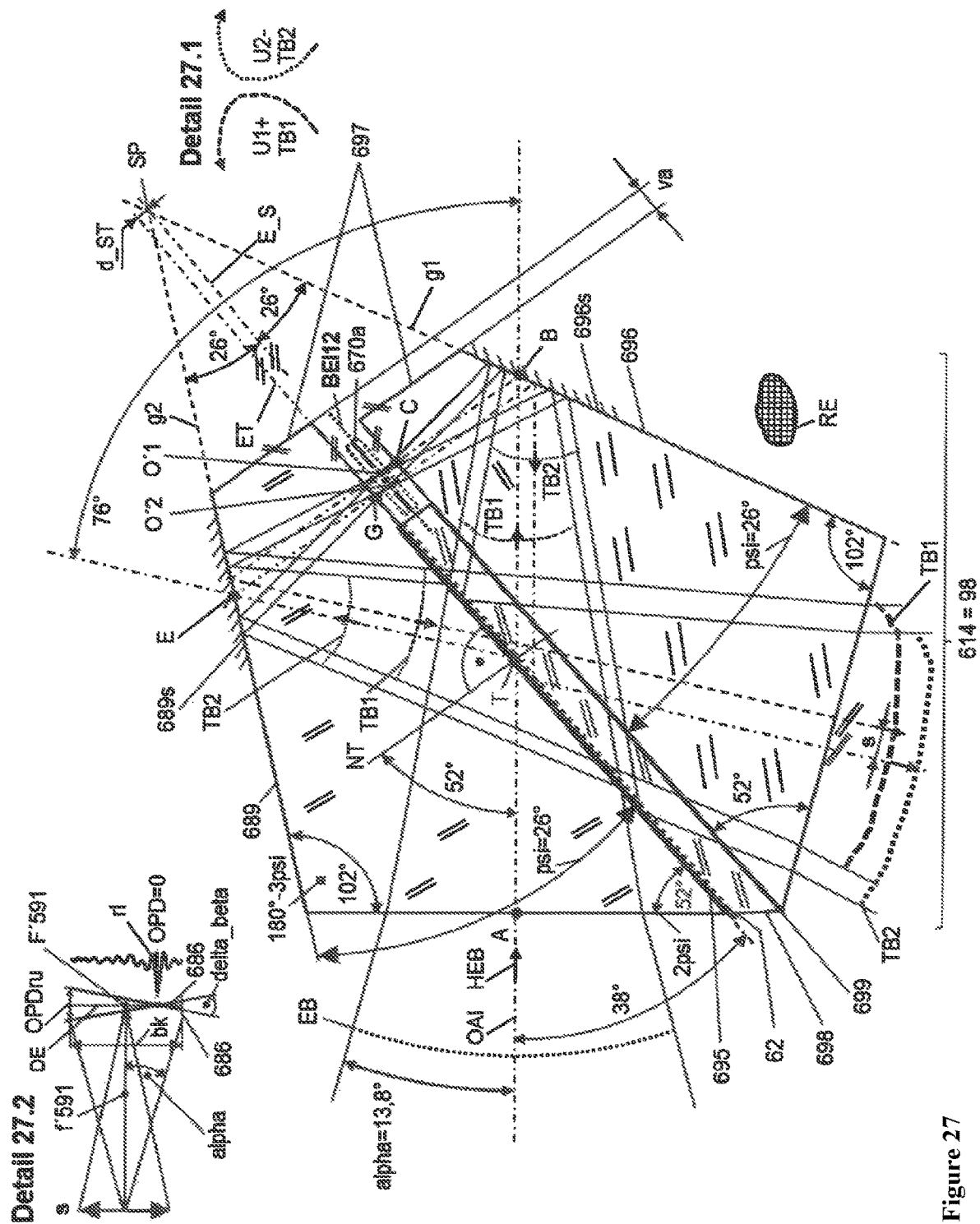
Figure 29:
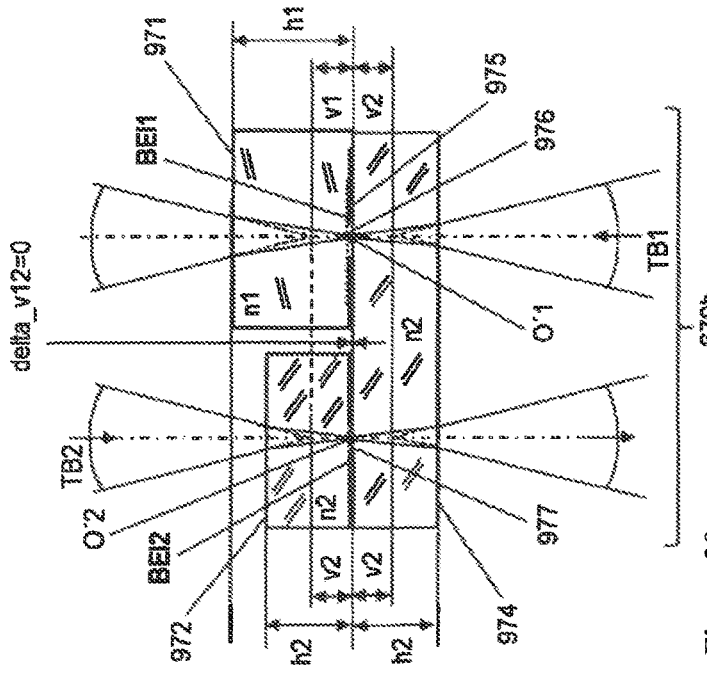
Figure 28A:
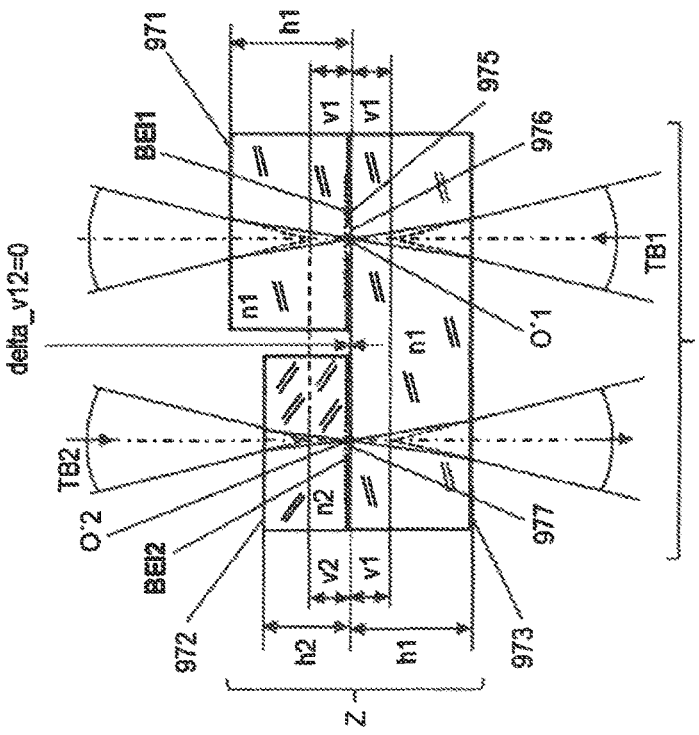
Figure 28B:
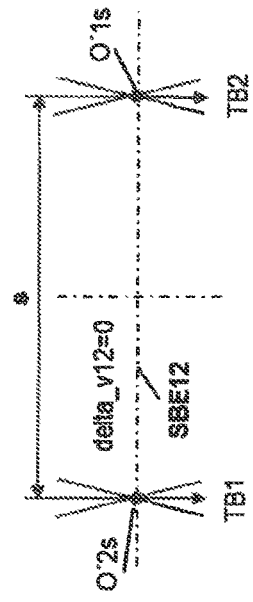
Figure 30:
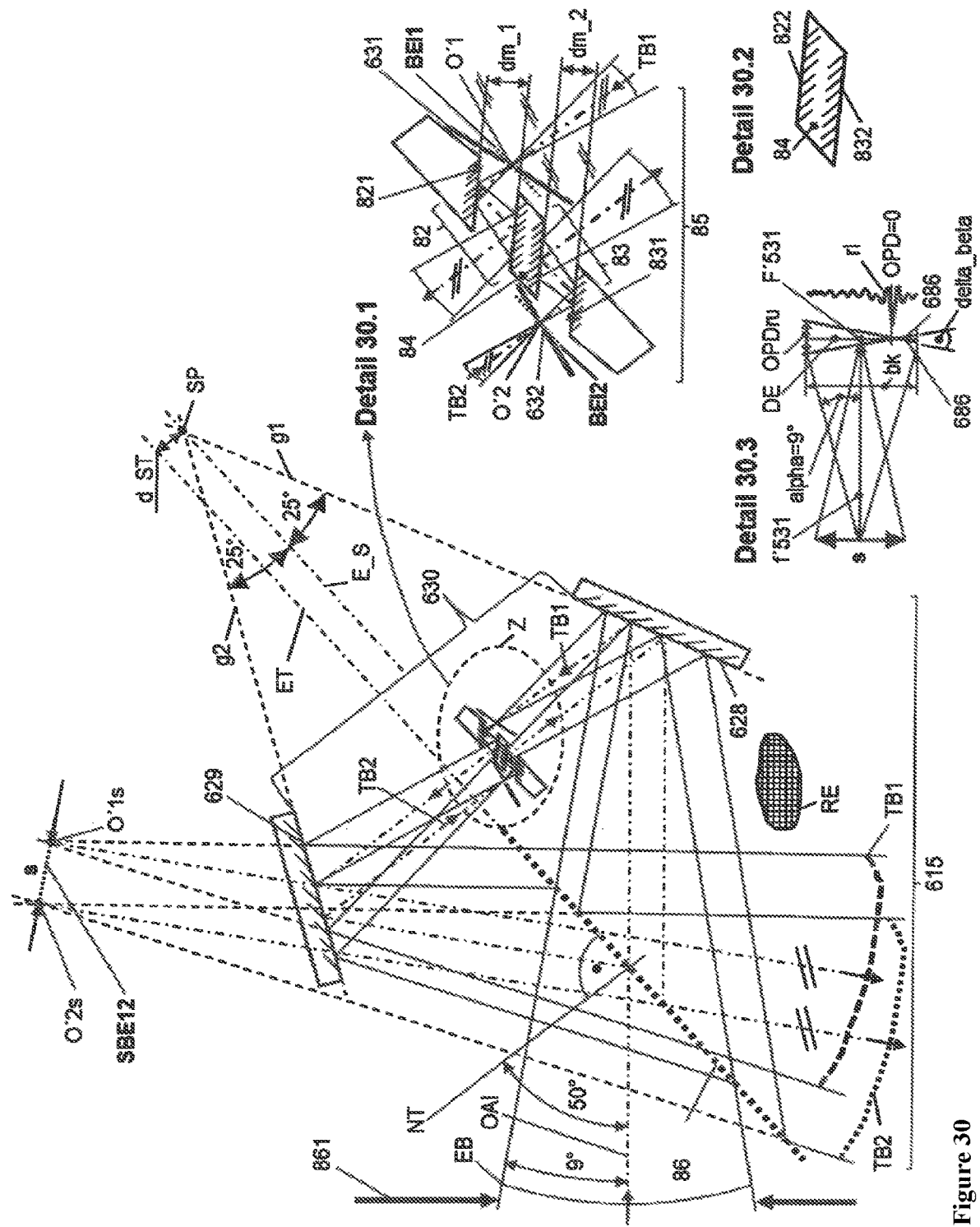
Figure 31:
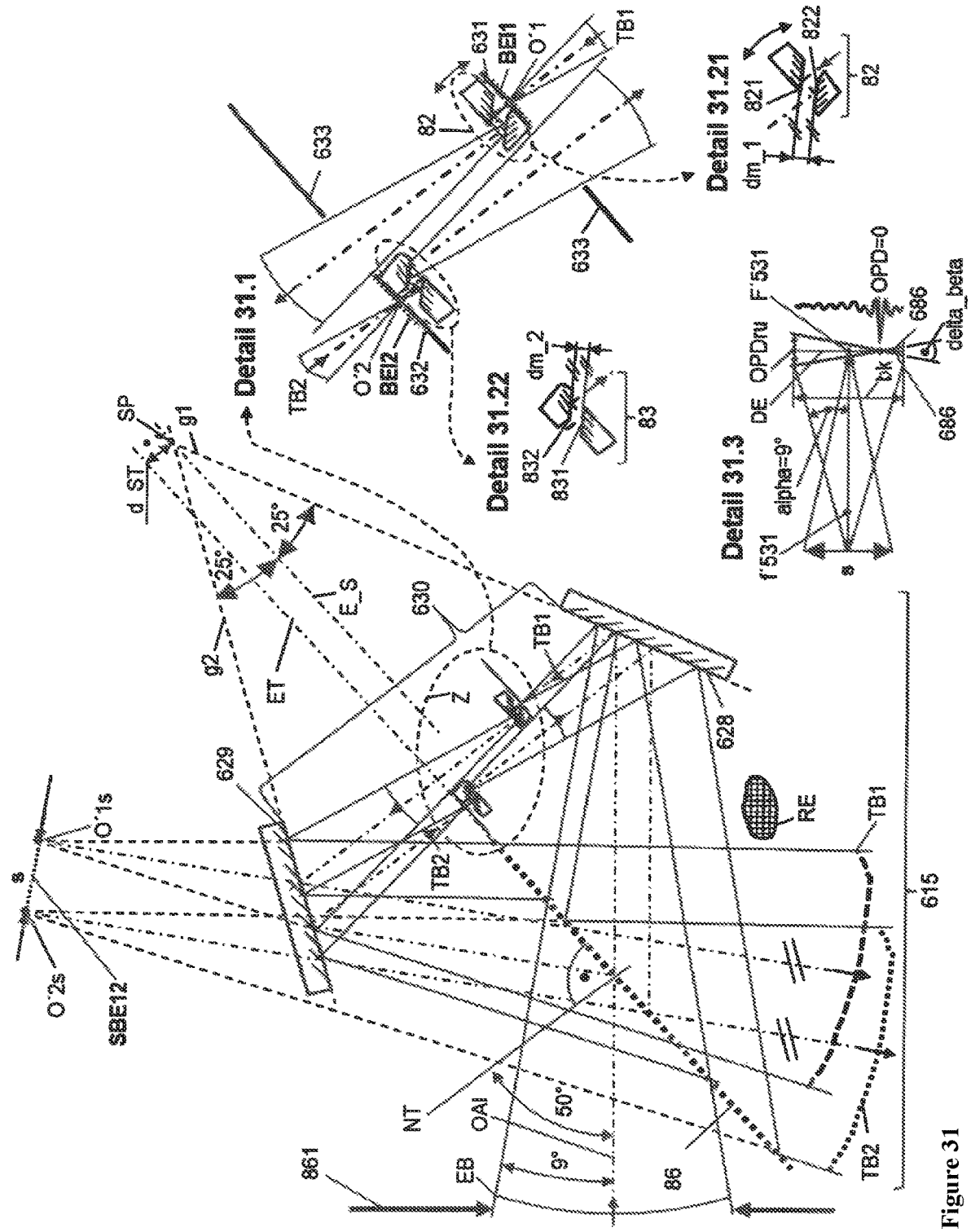
Figure 32:
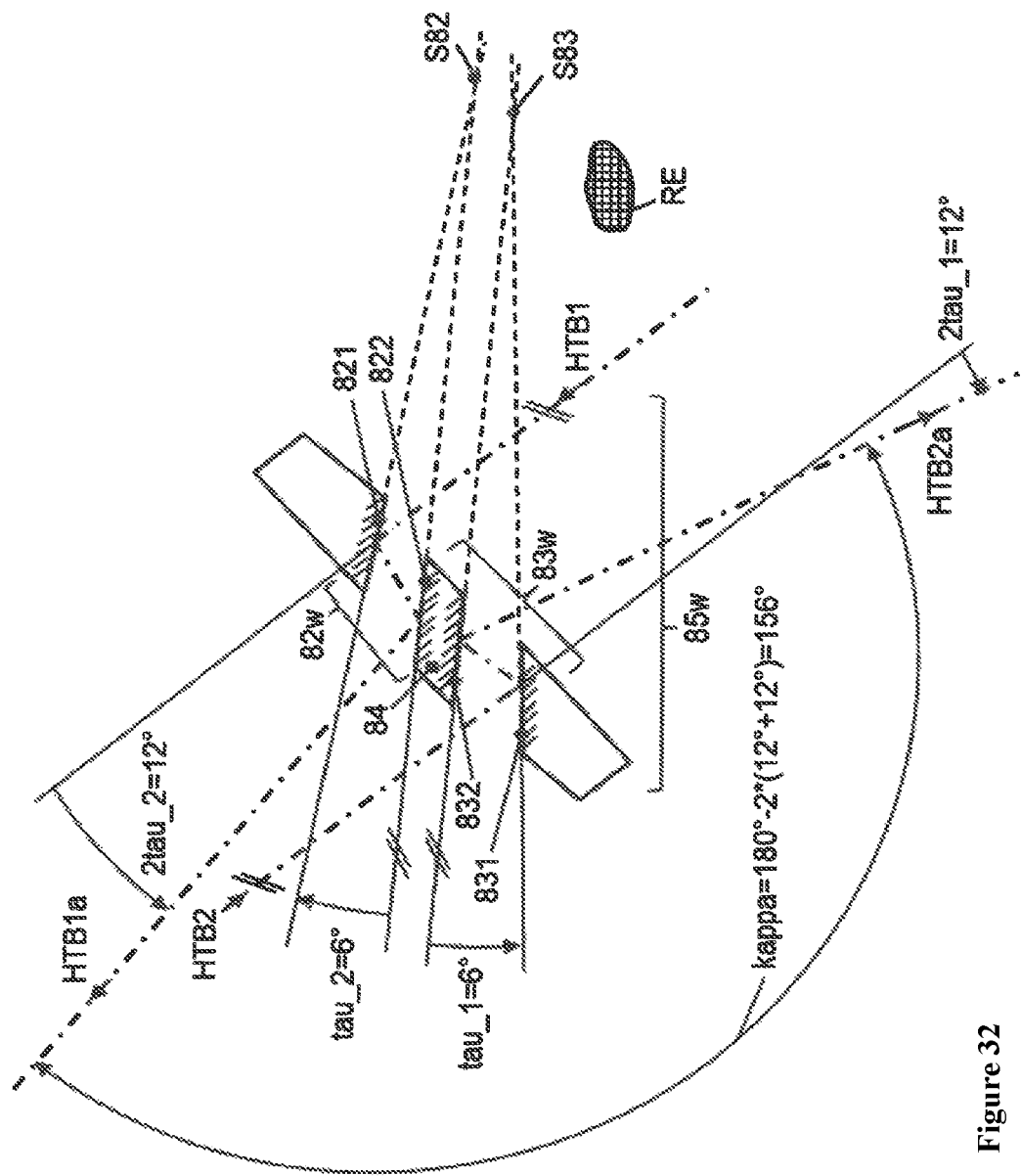
Figure 33:
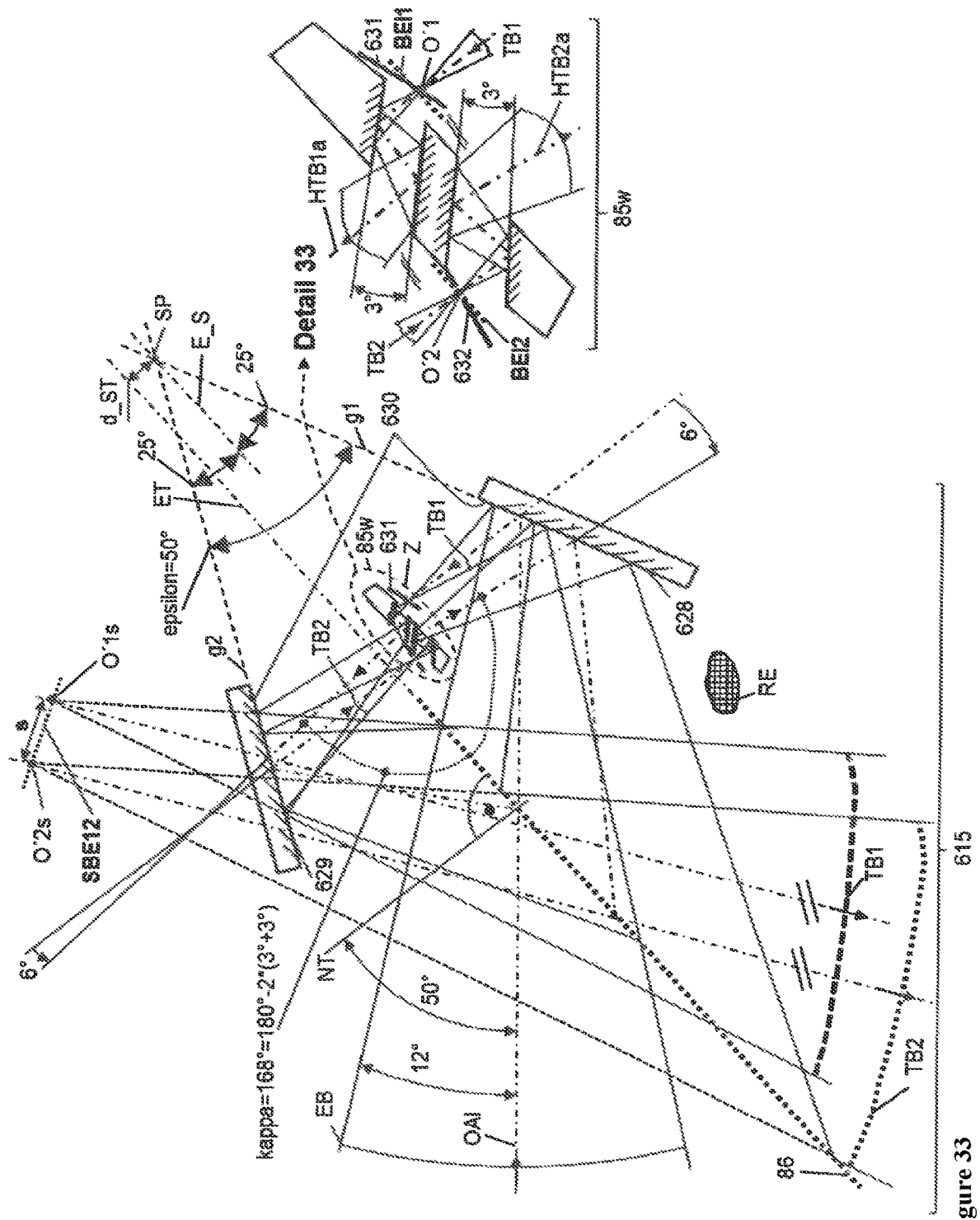
Figure 34:
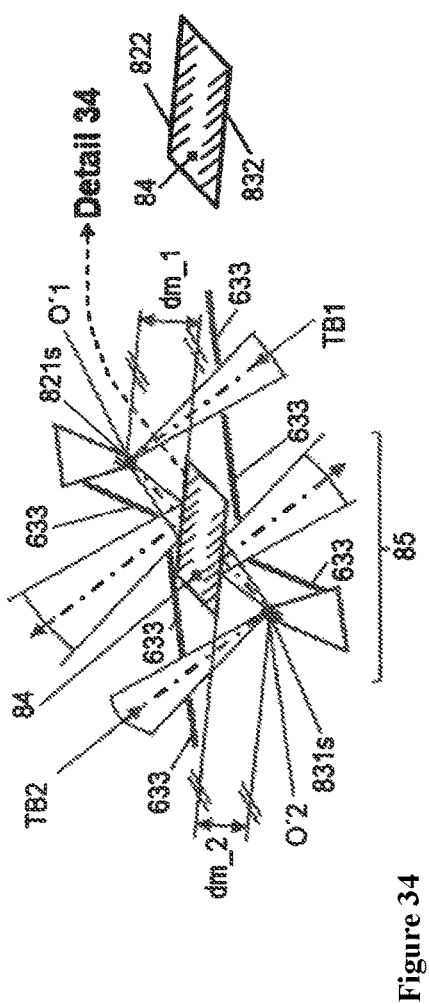
Figure 35:
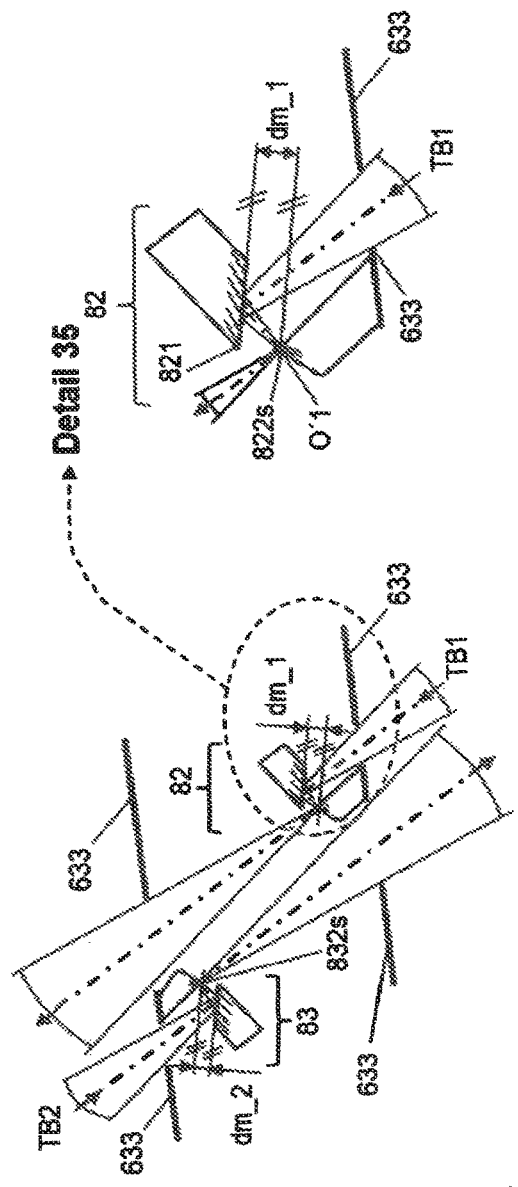
Figure 36:
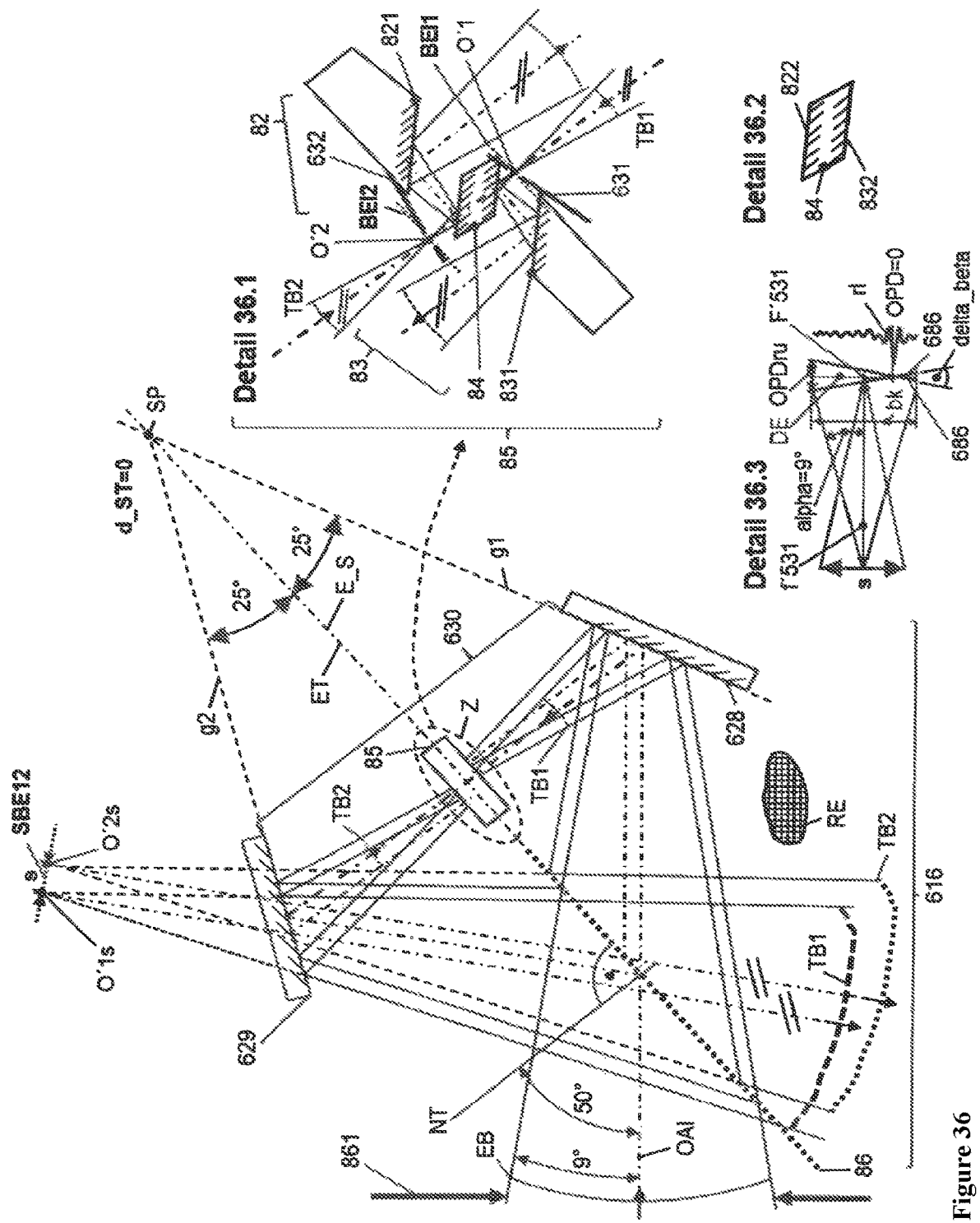

A description of the drawing follows, and the exemplary embodiments show:

FIG. 1 is a schematic side view of an exemplary use of an exemplary FT spectrometer on a patient;

FIG. 2 is a schematic reverse imaging of an exemplary use of an exemplary FT spectrometer on a patient;

FIG. 3 is a schematic view of an exemplary FT spectrometer, in particular of a single shot line spectrometer;

FIG. 4 is a schematic view of an exemplary Michelson-Type Interferometer;

FIG. 5 is a schematic view of an exemplary rooftop reflector;

FIG. 6 is a schematic view of an exemplary rooftop reflector;

FIG. 7 is a schematic view of an exemplary rooftop reflector;

FIG. 8 is a schematic view of an exemplary rooftop reflector;

FIG. 9 is a schematic view of imaging properties of an anamorphic and largely achromatic exemplary lens arranged downstream of the Michelson-Type Interferometer for detecting spatial interferograms;

FIG. 10 is a further schematic view of imaging properties of an anamorphic and largely achromatic example only lens arranged downstream of the Michelson-Type Interferometer for detecting spatial interferograms;

FIG. 11 is a schematic view of section of an exemplary Michelson-Type Interferometer;

FIG. 12 is a schematic view of an exemplary Mach-Zehnder Interferometer;

FIG. 13 is a schematic view of an exemplary cyclical double beam interferometer;

FIG. 14 is a schematic view of an exemplary cyclical double beam interferometer;

FIG. 15 is a schematic view of an exemplary cyclical double beam interferometer;

FIG. 16 is a schematic view of an exemplary cyclical double beam interferometer;

FIG. 17 is a schematic view of an exemplary cyclical double beam interferometer;

FIG. 18a is a schematic view of the optical effect of an exemplary plane plate group;

FIG. 18b is a schematic view of an image position difference in the depth axis delta_v;

FIG. 19a is a schematic view of an exemplary plane plate group;

FIG. 19b is a schematic view of an image position difference in the depth axis delta_v=0;

FIG. 20 is a schematic view of an exemplary cyclical double beam interferometer;

FIG. 21 is a schematic view of an exemplary cyclical double beam interferometer;

FIG. 22 is a schematic view of an exemplary cyclical double beam interferometer;

FIG. 23 is a schematic view of an exemplary cyclical double beam interferometer;

FIG. 24 is a schematic view of an exemplary cyclical double beam interferometer;

FIG. 25 is a schematic view of an exemplary cyclical double beam interferometer;

FIG. 26 is a schematic view of an exemplary cyclical double beam interferometer;

FIG. 27 is a schematic view of an exemplary cyclical double beam interferometer;

FIG. 28a is a schematic view of an exemplary plane plate group;

FIG. 28b is a schematic view of an image position difference in the depth axis delta_v=0;

FIG. 29 is a schematic view of an exemplary plane plate group;

FIG. 30 is a schematic view of an exemplary cyclical interferometer;

FIG. 31 is a schematic view of an exemplary cyclical interferometer;

FIG. 32 is a schematic view of an exemplary double mirrored staircase;

FIG. 33 is a schematic view of an exemplary cyclical double beam interferometer;

FIG. 34 is a schematic view of an exemplary double mirrored staircase;

FIG. 35 is a schematic view of an exemplary arrangement with two separated mirrored staircases;

FIG. 36 is a schematic view of a cyclical double beam interferometer; and

Figure 37:
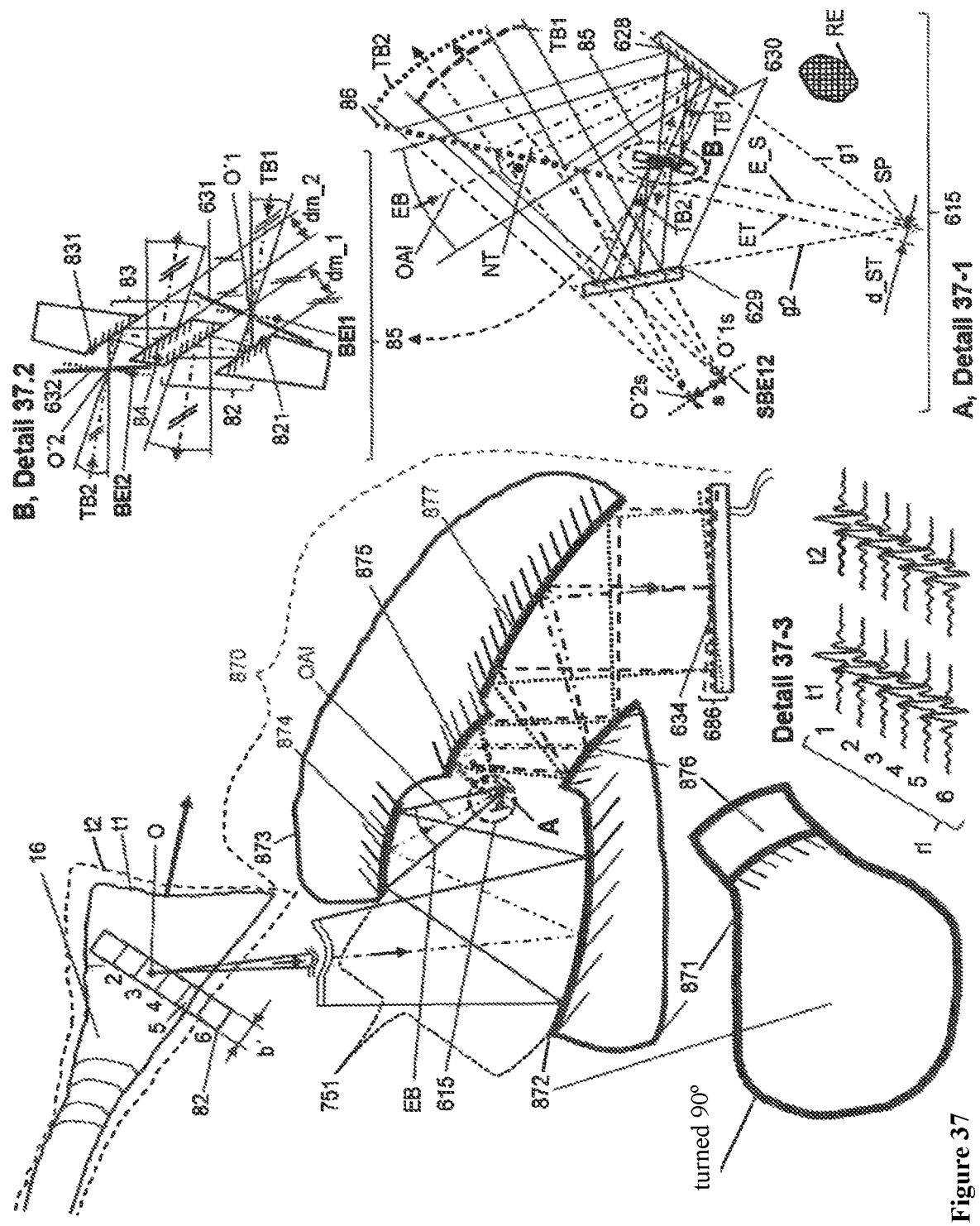

FIG. 37 is a schematic view of an exemplary spectrometer system in use.

A description is provided by means of FIG. 1 to FIG. 37 and by means of eleven exemplary embodiments, each without a figure (not shown schematically based on a drawing).

In the description to follow, the term 'light' is essentially used as a synonym for electromagnetic radiation, in particular from the UV up to the terahertz range, including infrared radiation, in particular thermal radiation. Herein, the term "Spectrometer System" in particular refers to a Single Shot Fourier Transformation Spectrometer with a double beam interferometer, which is designed to generate a lateral shear s. This can either be based on an active illumination of the measured object, which preferably can also represent a structured illumination, and/or the measured object can be self-luminescent; external light can in particularly be scattered from the surface of the measured object. The term "Single Shot" essentially refers to obtaining or generating or capturing spatial interferograms by means of double beam interferometry with a single recording of a raster detector, generally an image recording in a comparatively short time. This is generally the integration time of a camera in the UV, in the VIS, in the NIR, or in the MIR range. Depending on the camera type and depending on the recording conditions, this integration time can comprise a range from the single-digit microsecond range up to the single digit second range.

FIG. 1 shows a use of an exemplary FT spectrometer. FIG. 1 is a schematic illustration, in particular of an arrangement of a patient with safety goggles, wherein a medically conspicuous skin feature 2 on the back 1 of the patient is to be examined. In particular, the diagnostics are tasked to determine whether the skin feature 2 is a birthmark or a melanoma. The complicated diagnostic procedure is to be validated as objectively as possible, preferably by means of a spectral measurement, and in particular by means of a spectrometer system 20.

For purposes of the examination, the dermatologist can for skin screening make use of an essentially mobile measurement head 30 in single shot mode, which is formed as a handheld device for scanning over a measured object, in this case the region of a back 1. This device can be mapped to a pulsed NIR light source 40 for active illumination in stripe shape and/or for a fine structured illumination of the back 1 and an optics unit 50 with an integrated double beam interferometer 601.

This mobile measurement head 30 is essentially slowly guided by hand, e.g. with a speed of approximately v=1 cm/s over the back 1 of the patient, here from bottom to top, or essentially in +y direction.

Although not shown here, a camera, in particular a VIS monitoring camera, is integrated in this case in the mobile measurement head 30 for diagnostic purposes of the skin surface on the back 1. The imaging data recorded with this monitoring camera can—where appropriate—additionally be used to support the construction of a hyperspectral image, in particular when the scan movement of the mobile measurement head 30 by hand is essentially not performed at a constant speed. Two position markers not shown here are for this purpose applied on the back 1. The spatial interferograms rl incrementally collected during a moderate movement of the mobile measurement head 30, and which can generally be obtained in single shot mode using an InGaAs camera 54 for the near infrared spectral range, in this case along a line in horizontal direction, can be converted into spectrums SP and can be assembled into a hyperspectral image set. The camera, which can in particular be an InGaAs camera 54, can preferably in this exemplary embodiment—as also the pulsed light source, which in particular is formed as, or comprises, an NIR light source 40—be formed essentially controllable by the computer 21. These two components can preferably also be synchronized.

The spatial interferograms rl are generally recorded in a single shot using a double beam interferometer 601 and can therefore be computationally processed into spectrums along the line in horizontal direction using a computing program to execute fast Fourier transformation (FFT). This can be accomplished line by line for the selected skin area on the back 1 for the spatial interferograms rl that are recorded by the optics unit 50 of the mobile measurement head 30. After the recording of spatial interferograms rl is completed in an upward motion that covers the skin region of medical interest, the calculated spectrums can be mapped point by point to an image map of the examined skin region. It is in this case seen as admissible when potentially not perfectly or not optimally uniform, and essentially not perfectly laterally guided hand motions of the dermatologist while using the mobile measurement head 30 causes the image point raster to have certain elongated and compressed areas, but is essentially without gaps. Using an analysis program 22 for analyzing the spectrums SP, where appropriate, executed on a high-performance computer 21 and/or a computing system, in particular risk and high-risk regions can be identified based on the spectral signatures of the spectrums SP. In this case, algorithms for spectrum analysis, for example based on the Principal Component Analysis approach, can be used and/or approaches with artificial intelligence can be candidates. The algorithms for evaluating and analyzing the spectrums SP for purposes of assessing a tumor risk are not an area of focus for purposes of this invention, because the present invention in particular relates to the fast provisioning of optical primary data, or spatial interferograms rl. The results of the evaluation and analysis of the spectrums SP can be shown on a monitor 23.

Different than shown in FIG. 1, the illumination can in a further exemplary embodiment 1 (not shown schematically based on a drawing) be performed coaxially by coupling in the light using a beam splitter. In particular in this case, a projected light stripe and the measurement field at all times overlap based on an arbitrary position of the measurement field. In this case, a zoom function can also readily be integrated into the optics unit 50 of the mobile measure head 30. This approach with coaxially coupling in the light to illuminate the back 1, is for example used in FIG. 3.

FIG. 2 shows a schematic illustration of the back of view of the patient. The exemplary projected light stripe 80, which is created on the back 1 of the patient using an NIR stripe light source, is essentially significantly longer than the measurement field 81 of the optics unit 50 of the mobile measurement head 30. The measurement field can then be fully illuminated even for moderate distance changes of the measurement head 30. During measurement, the mobile measurement head 30 can be moved, in particular by hand and laterally across a region of the back. In this case, the interferometer 601 at least intermittently, and the optics unit 50 constantly—that is to say without significant interruptions and/or in chronological intervals—record multiple spatial interferograms rl in single shot mode, wherein the light source 40 generates a synchronized flash light for the purpose of illuminating the measurement field 81 in the shape of a stripe 80.

The spectrometer system can alternatively or additionally also be used to examine a tissue region during a surgical procedure for purposes of tissue differentiation.

FIG. 3 shows the principle for the approach for a single shot line spectrometer with an illumination of the back 1 with a stripe 80. A y-scan can be executed here using a transport carriage 90 with a stepper motor drive not shown here. This y-scan is executed in particular using the mobile measurement head 30 essentially laterally in relation to the stripe 80 across the back 1 of a patient preferably sitting still. The back 1 can in this case be subject to intense illumination in the form of a stripe 80 using a pulsed stripe light source 43. In particular a coupling beam splitter cube 57 is used to coaxially couple the light into the optics unit 50 of the mobile measurement head 30. The measurement field 81 is in particular illuminated in this manner using a stripe 80. The region on the back 1 illuminated in this manner is in particular rendered by using an upstream lens 70, essentially in focus into the double beam interferometer 601 by a plurality of individual beams. Approximately one beam is mapped to each object point. A representative beam is shown with solid lines, the beam belonging to an object point O on the optical axis. Three further beams, representing a plurality of beams, are drawn as dotted lines in FIG. 3.

In this case, telecentricity applies at least approximately for the object rendering on the side of the upstream lens 70 facing the double beam interferometer 601 with the optical axis OAI, however, a telecentricity aperture is not shown here. The upstream lens 70 or the lens 70 arranged in front thereof further comprises an autofocus function. The object distance determined with the latter is handed over to the analysis program as information during the recording, in particular at least intermittently constantly or permanently and/or in chronological intervals because a distance change changes the imaging scale during in the imaging, which can be taken into account during the analysis and rendering of the hyperspectral image.

The double beam interferometer 601 generates a lateral shear s and in each of the two interferometer arms has a field of view discriminator BFD1 and BFD2 of essentially equal construction, which is shown in the detailed FIG. 3.1 of FIG. 3 as the field of view discriminator BFD1 with the width b and the length L. FIG. 3 shows a symbolic or schematic drawing (additionally rendered visible by rotating out in perspective) of the apparent images BFD1's and BFD2's of the field of view discriminators BFD1 and BFD, see detailed FIG. 3.1, in the likewise symbolically or schematically shown double beam interferometer 601 in the apparent image plane SBE12.

At least one point each of one of these apparent images BFD1's and BFD2's of the field of view discriminators is conjugated with respectively one apparent image point O'1s and O'2s of the object point O, wherein the image points O'1s and O'2s are optically conjugated in the double beam interferometer 601 by beam splitting, and given that the double beam interferometer 601 is accurately adjusted essentially lie together in the apparent image plane SBE12 and also represent coherent image points. For the downstream anamorphic lens 51, the apparent image plane SBE12 in turn represents the object plane.

Consequently, pairs of essentially coherent partial beams are preferably created at the output of the double beam interferometer 601 that are shown here as examples in the figures as two partial beams TB1 and TB2, which are however generally representative for a plurality partial beams.

The two field of view discriminators BFD1 and BFD2 are preferably arranged in the double beam interferometer 601 such that an optical conjugation is created for these. The field of view discriminators BFD1 and BFD2 are in this case expanded essentially laterally such that in spite of discrimination, several beams of several object points can nevertheless pass these. It is implied that one point is always mapped to one beam. An image 80'1 is created on the field of view discriminator BFD1 by imaging, and an image 80'2 of the stripe 80 is generated on the field of few discriminator BFD2 by imaging. In each interferometer arm, a part of the light from each of these two images 80'1 and 80'2 can pass the discriminators BFD1 and BFD2 with a field of width b and length L. Light outside of this field is preferably excluded from the further imaging, and is therefore preferably lost. The reverse imaging of the two field of view discriminators BFD1 and BFD2 determines the width of the measurement field b' and their length L' on the back 1 with the imaging scale of the upstream lens 70, as shown in the detail FIG. 3.2.

The measurement field 81 recorded on the back 1 is solely determined by reverse imaging the two field of view discriminators BFD1 and BFD2 using the upstream lens 70. As representatives for many, the detailed FIG. 3.2 in this case only shows four object elements with appropriately small surface area, namely OE1 to OE4, with the height increased for better visibility. The actual number of object elements is however typically at an order of magnitude of approximately 500 in the NIR spectral range, with the appropriate use of an MIR camera with approximately about 500 pixels in x direction. For every object element OE, the measurement method determines exactly one spectrum SP, in particular when this object element OE is sufficiently cooperative for a measurement, or can supply a recordable spatial interferogram rl. The width of the measurement field b' on the back 1 is in this case approximately 0.2 mm. Moreover, the detailed FIG. 3.2 indicates or schematically renders the two coincidental images BFD1'r and BFD2'r of the two field of view discriminators BFD1 and BFD2 that are created by imagined or imaginary reverse imaging of the latter on the back 1.

The illuminated field of view discriminators BFD1 and BFD2, which represent two coherent light sources, are rendered on the output of an anamorphic lens 51 arranged downstream of the double beam interferometer 601, wherein the lens 51 is also chromatically corrected. The imaging of the object 51, which is formed with a rotational component 511 and also with a cylindrical component 512, generates from an object point respectively two cylindrical waves essentially tilted toward each other, which here are projected onto a camera as a raster detector, in particular an InGaAs camera 54, wherein each pair of cylindrical waves respectively forms one spatial interferogram rl that is mapped to an object element OE. An object element OE can in this case be so small that it is perceived as a point because it is no longer laterally resolved by the downstream optics, or with its image extent in x direction approaches the order of magnitude of a pixel of the raster detector when imaged on the raster detector, shown here as an InGaAs camera 54.

The cylindrical wave fronts 385 tilted toward each other are shown in the detail FIG. 3.3 with the peak lines 386 that are essentially tilted towards each other by delta_beta. This special optical function of the anamorphic lens 51 is illustrated or schematically visualized in FIG. 9 and FIG. 10. The interferometer has been accurately adjusted, including a matching of the optical distances of the arms of the double beam interferometer 601. It is noteworthy in this case that due to the comparatively low value of the width b of 0.2 mm, the requirements for adjusting an end mirror and/or a double periscope group in the double beam interferometer 601 are not very high in the present case, which represents a significant advantage, for example in rough ambient conditions and with comparatively fast temperature changes. In general terms, the lower the selected value b, the less critical the adjustment of the interferometer 601. Even a tilt of an interferometer mirror about a tilt axis in the double beam interferometer 601 that is parallel to the reference plane RE is comparatively noncritical. This absence of sensitivity to tilting—albeit within certain limits and at all times by observing the scanning theorem well known to persons skilled in the art—is in particular the product of the spatial resolution of the spatial interferograms rl using raster receivers. The detail FIG. 3.4 shows examples of several spatial interferograms rl.

The somewhat varying optical path differences of the field of view in the spatial interferograms rl caused by a not entirely perfect adjustment of the double beam interferometer 601 do not typically represent a significant problem for the numerical analysis of the spatial interferograms rl, given the prior art.

A high signal-to-noise ratio can only be achieved in the spectrum when the contrast of the spatial interferograms rl is sufficiently good or large. Is therefore important that the interferometer hardware ensures or achieves a highest possible or relatively high contrast of the spatial interferograms rl, because the search for spectral signatures, in particular in biological measured objects, are not significantly pronounced or do not exhibit significantly high identifying characteristics.

The field of view discriminators BFD1 and BFD2 in the exemplary embodiment in FIG. 3 can also be and/or comprise narrow plane mirrors of with width b and length L. Light that falls outside such a plane mirror can enter light traps and/or impact a matte-black mask of the narrow plane mirror of width b.

The detail FIG. 3.5 shows examples of spectrums Sp1 to Sp4 calculated from an exemplary image recording from which the spatial interferograms rl in the detail FIG. 3.4 are obtained, which according to the detail FIG. 3.5 are in this case mapped to the x coordinate according to the detail FIG. 3.6 or applied versus the x coordinate. The spectral resolution is indicated as delta sigma in the detail FIG. 3.6. By means of a y scan, the known data cube or the multi-dimensional data ensemble in the diagram (x, y, wave number) and/or (x, y, wavelength) can be determined for a region of the back 1 or can be mapped to a region of the back 1.

In a further exemplary embodiment 2 (not shown schematically based on a drawing), a multi-axis robot arm is used to move the mobile measurement head 30. The latter permits reaching a particularly high degree of flexibility, in particular in comparison to a linearly operating transport carriage 90. During a surgical procedure, such an exemplary embodiment 2 is particularly advantageous due its flexible local positioning.

FIG. 4 is a schematic representation of a relatively compact Michelson-Type Interferometer 602 that is in particular designed for use in the NIR range. A pulsed light source 44 is essentially intended to project a light stripe 80 onto the (biological) measured object 10 and for this purpose comprises beamforming optics 45 in mirror form that are integrated into the light source 44. The light emitted by the light source 44 is coupled through an opening in the former essentially coaxially into the illumination beam path using a telecentric aperture 72 and a pentaprism 46, and enters the Michelson-Type Interferometer 602 as a focused incident beam EB through an upstream lens 71. An example of this Michelson-Type Interferometer 602 is herein formed with a beam splitter cube 622, for example with an edge length of approximately 10 mm and beam splitter layer 62. The beam splitter cube 622 preferably comprises a glass, and the half opening angle alpha in the glass of the beam splitter cube 622 is for example preferably about 12 degrees. This exemplary angle is a comparatively large angle and as a result in particular causes a large share of the light emitted by the measured object 10 to be captured. The beam splitter cube 622 for example comprises borosilicate crown glass (BK7). Alternatively or additionally, a beam splitter, in particular a beam splitter cube, can in particular comprise other materials commonly used for optical elements, such as quartz glass, crown glass, flint glass, and similar materials. An input beam EB (shown here as an example for many) is in particular split on the beam splitter layer 62 in the two arms IA1 and IA2 of the Michelson-Type Interferometer 602. The passing through or transmitted partial beam TB1 preferably impacts a double mirror periscope reflector in the arm IA1 of the Michelson-Type Interferometer 602, in particular a 90-degree rooftop reflector 641 for a 180° deflection, comprising metal, in particular manufactured from metal with single point diamond machining. This rooftop reflector 641 is in particular arranged in a metal base body 643. A gap aperture 645 with the function of a field of view discriminator is preferably arranged in the 90-degree rooftop reflector 641, as is for example indicated in the detail FIG. 4.1. By performing a correspondingly preferred adjustment in the depth axis of the upstream lens 70, the position of the image plane BEI1 coincides with the gap of the gap aperture 645, preferably with the image point O'1. In the figure, the 90-degree rooftop reflector 641 is shifted to the left, that is to say shifted essentially vertically in relation to the optical axis OAI of the upstream lens 71 from the former by a distance, thus resulting in a lateral shear s1 for the partial beam TB1 reflected on the 90-degree rooftop reflector 641 that in particular and essentially corresponds to the distance of the shift vertically in relation to the optical axis OAI.

The shift of the 90-degree rooftop reflector 641 specified here is performed or created in the present figure or embodiment in a horizontal lateral direction "to the left". The detail FIG. 4.1 indicates the 90-degree rooftop reflector 641 as an enlargement with the gap aperture 645, which coincides with the image plane BEI1. Because the 90-degree rooftop reflector 641 is of equal construction as the 90-degree rooftop reflector 643, the reference symbols in FIG. 4 also shown for the latter.

In general terms, a beam splitter cube specified in this description can also be replaced by another beam splitter, for example a beam splitter in foil form or formed with a membrane (Pellicle beam splitter)

The partial beam TB2 reflected on the beam splitter layer 62 also impacts a double mirror periscope reflector in the arm IA2 of the Michelson-Type Interferometer 602, in particular a 90-degree rooftop reflector 642, which is preferably and essentially of equal construction as the rooftop reflector 641. The 90-degree rooftop reflector 642 is likewise shifted laterally, upward in this case, that is to say essentially parallel in relation to the optical axis OAI of the upstream lens 71, and essentially vertically in relation to the optical axis OA2 of the InGaAs camera 54, and from this optical axis OA2 by a distance. The shift of the 90-degree rooftop reflector 642 specified here is in other words performed or created in the present figure or embodiment in a vertical lateral direction "upward". The resulting lateral shear s2 in particular and essentially corresponds to the shift vertically in relation to the optical axis OA2 or parallel to the optical axis OAI. But this is contrarian with respect to the symmetry to the beam splitter layer 62, so that the lateral shear s2 resulting in the arm IA2 is added to the sum of s1 and s2 equal s. This addition due to the geometrical arrangement represents an opportunity to achieve a comparatively large resulting lateral shear s.

After reflecting on the beam splitter layer 62 in the arm IA1 respectively after passing the former in the arm IA2, the two partial beams TB1 and TB2 at least partially enter the anamorphic and largely achromatic lens 51 at the output of the Michelson-Type Interferometer 602, the former consisting of an essentially rotationally symmetrical component 511 and a cylindrical component 512. For a detailed understanding of the anamorphic lens 51, reference is made to FIG. 9 and FIG. 10 and the discussion related to these.

After exiting the anamorphic lens 51, cylindrical waves are formed that are indicated in the detail FIG. 4.2 as cylindrical wave fronts 685. In order to improve the illustration, these are shifted in the depth axis and in particular shown in a perspective view to indicate the spatial projection. The interference of the cylindrical waves 685 preferably generates spatial interferograms rl on the camera, which in particular comprises an InGaAs camera 54. The angle delta_beta between the cylindrical wave fronts 685 interfering with each other, specifically the angle delta_beta between the two peak lines 686, is indicated here in greatly enlarged form. The light of the coherent apparent light source points O'1s and O'2s respectively causes the generation of a spatial interferogram rl as interference of cylindrical waves, wherein the peak lines 686 of the wavefronts of the former are located on the detector surface of the InGaAs camera 54 or in the immediate surroundings of the latter. This spatial interferogram rl is here essentially formed centered on the chip of the camera, which can be an InGaAs camera 54, because the location in the center here with the optical distance difference OPD is preferably equal to zero by synchronizing the Michelson-Type Interferometer 602. A measured object scanning mechanism for the y direction can preferably be available, which is however not indicated in the drawings here.

The maximum achievable optical distance difference OPDr in the double beam interferometer, given an essentially symmetrical location of the spatial interferogram rl, can be approximately calculated based on the illustration in detail FIG. 4.4. When the example calculation assumes a numerical aperture A=sin(alpha) of approximately 0.1, which in air corresponds to an aperture angle of approximately 5.7 degrees and represents a comparatively small value, and given a lateral shear of approximately s=1.04 mm, this results in a maximum distance difference OPDr at the edge of the chip in the InGaAs camera 54 in the detection plane DE of the lens 51, which comprises the lens 511, of OPDr=A*s or approximately 0.104 mm. In this case, the spatial interferogram rl preferably lies or is created centered on the chip. Given an assumed triangular apodization of the intensity values of the spatial interferogram rl when calculating the spectrum using fast Fourier transformation, a spectral resolution delta sigma of approximately 96 $cm^{-1}$ can be achieved with the reciprocal value of the optical distance difference OPDr, here for example approximately 1/0,102 mm. Given a wavelength of approximately 1000 nm, this corresponds to a spectral resolution in the wavelength region of approximately 9.6 nm. Given a focal length f' 511 of approximately 60 mm for the rotationally symmetric component 511, the formula a=2A*f' 511 is used to determine the required minimum edge length of the InGaAs camera 54 at approximately 15.0 mm. Without limitation, the camera can for example in the present case be an InGaAs camera of type Goldeye P-032 SWIR from Allied Vision and comprises a width bk of approximately 15.9 mm and a pixel pitch of approximately 25 μm and approximately 636×508 pixels. Assuming compliance with the scanning theorem, an in particular symmetrical, spatial interferogram rl can be fully recorded with the optical distance difference at the edge of the chip OPDr with the value of approximately 0.104 mm in the spectral range from approximately 900 nm to 1700 nm, because the interference stripes of the shortest wavelength of approximately 900 nm on the camera chip—here preferably with an interference stripe width of approximately about 52 μm—are wider than double the pixel pitch of this InGaAs camera chip. The interference stripe width can be approximated from the quotient f' 511 divided by the lateral shear s and multiplied with the respective wavelength.

In an exemplary embodiment 3 (not shown schematically based on a drawing), such an arrangement—with corresponding modifications—can also be used to measure spectrums of fluorescent light, in particular when an excitation light source in the ultraviolet spectral range and a dichroic beam splitter are used.

In an exemplary embodiment 4 with at least one derivative of the embodiment from FIG. 4 (not shown schematically based on a drawing), the beam splitter cube 622 can also be formed somewhat asymmetrically, so that the glass paths or the two optical distances through the glass material or the glass in the two interferometer arms IA1 and IA2 however exhibit at least minor differences, typically in an order of magnitude up to a maximum of 1 mm. The path differences resulting from the different optical distances can for example be between about 3 nm and 3 mm, in particular between about 200 nm and 2 nm and preferably between about 500 nm and 1.5 mm. During detection, spatial interferograms can then be generated that have an optical distance difference or a difference between the two optical distances or a path difference essentially unequal to zero in the center of the camera, in particular in the center of the InGaAs camera. Due to the unequal glass paths in the two interferometer arms, the peak lines of the interfering cylindrical waves are then only approximately straight-lined for a wavefront from an interferometer arm, or are slightly curved, since there is a residual opening area because the upstream lens 71 can only be corrected for a specific glass distance. The unchangeable correction of the upstream lens 71 in the optics design for a specific glass distance—so that the opening error does not occur—can then only be perfect for a specific glass distance of an interferometer arm. The residual opening error that then remains for the other interferometer arm due to a here slightly different glass distance, for which there is no perfect correction, can ultimately result in nonlinearities in the spatial interferogram and may require a numerical correction of the interferogram rl as needed.

However, it is also in particular possible in a further exemplary embodiment 5 according to FIG. 4 (not shown schematically based on a drawing) to form one of the two plane mirrors as a comparatively very narrow, elongated plane in the proximity of the rooftop. The narrow plane mirror, for example with dimensions of 0.5 mm×10 mm can then by itself act as a field of view discriminator, wherein such an arrangement can only be used to obtain a comparatively very coarse hyperspectral image, for example with only 10 to 20 image lines in the image height.

FIG. 5 to FIG. 8 comprise various embodiments, in particular for forming the rooftop reflectors with integrated field of view discriminators, which are respectively preferably arranged in the image plane BEI1, for a Michelson-Type Interferometer. In particular, two field of view discriminators of essentially equal construction are respectively inserted into each arm of a Michelson-Type Interferometer. For this reason, the reference symbols for the rooftop reflectors are respectively indicated in the two interferometer arms. Alternatively, the field of view discriminators can essentially differ in their construction, optical properties, dimensioning, material, etc. FIG. 5 to FIG. 8 and also the detail FIG. 4.1 show the apparent end mirror surfaces SEF1 and SEF2 created by unfolding the rooftop reflectors 641 and 642; the former can be used for simplified imaging.

FIG. 5 shows a 90-degree rooftop reflector 641 machined by single point diamond, in particular made of metal for a 180° beam deflection. This 90-degree rooftop reflector 641 can in particular be used or arranged in the first arm IA1 of the Michelson-Type Interferometer 602, as shown in FIG. 4. The field of view discriminator is in this case in particular formed or equipped with a gap aperture 645 with the gap width b, which is formed essentially of equal construction as the gap aperture 646 in the second arm IA2 of the Michelson-Type Interferometer 602.

FIG. 6 shows a preferably computer-controllable piezo actuator 647 that can preferably be mapped to the gap aperture 645 in the rooftop reflector 641 and can permit an adjustment of the gap width b, and can therefore influence the lateral resolution. The two arrangements shown in FIG. 5 and FIG. 6 in particular permit a comparatively large spectral range, because this in particular relates to arrangements at least partially in air.

In an exemplary embodiment 6 (not shown schematically based on a drawing), a rooftop reflector 641 can also be inserted or arranged in a Michelson-Type Interferometer, given the use of a plate beam splitter for the optical MIR wavelength range, in particular with substrates that can comprise or be CaF2 and/or KBr.

FIG. 7 shows an arrangement with an elongated pinhole array 648 for precision field of view discrimination for a Michelson-Type Interferometer. As a supplement to this exemplary embodiment shown in FIG. 7, there is a further exemplary embodiment 7 wherein the measured object is illuminated with transmitted light and/or incident light with a light spot pattern matched to the pinhole array 648 and whose light is then confocally discriminated in the Michelson-Type Interferometer 602. This can also occur in the MIR range, given use of a corresponding plate beam splitter with substrates comprising CaF2 and/or KBr and a beam splitter layer suited for the MIR spectral range.

FIG. 8 is a schematic illustration of an option to embed an essentially elongated, light-permeable region 650-1 of width b in the visible spectral range with a transmissive liquid crystal display (LCD) 650, by using further optical polarization components not shown here but widely known among persons skilled in the art.

FIG. 9 and FIG. 10 show the imaging properties of an anamorphic and predominantly achromatic lens 51 arranged downstream of the Michelson-Type Interferometer and used for detecting spatial interferograms rl. Here, the function of this anamorphic lens 51 is explained in particular in conjunction with or in use with the metrology arrangement shown in FIG. 4. The drawing plane in FIG. 9 is the yz plane, which in this case represents the exemplary reference plane RE, and wherein this yz plane contains the apparent image points O'1s and O'2s that result following an unfolding of the beam paths. By way of amplitude splitting in the double beam interferometer, these image points O'1s and O'2s represent optically coherent image points of a scanned object point O. A particularly good and effective correction of the aberration is advantageous in the yz plane, essentially for the entire, but at least for the partially, used spectral range of the Fourier spectrometer, that is to say in particular originating from the object up to the raster detector, so that the spatial interferograms remain largely undisturbed.

The drawing plane in FIG. 10 corresponds to the xz plane indicated therein, and which is essentially vertical to the reference plane RE. This xz plane also comprises the apparent image point O'1s. Due to the additive refractive power of the cylindrical component 512 in the xz plane, the total refractive power of the anamorphic lens 51 is in the xz plane at least approximately twice as large compared to the total refractive power of the yz plane. In particular cylindrical wavefronts 685 are created in the detection plane DE, and whose peak lines 686 are essentially tilted toward each other, and which are essentially oriented parallel to the yz plane. The point O"1_xz in the detector plane DE is in particular the penetration point of the cylindrical wave, resulting in particular from the apparent image point O'1s, through the xz plane. The raster detector, shown here for example as an InGaAs camera 54, is essentially positioned in the detection plane DE. These relationships in particular also apply for the further downstream, anamorphic, and largely achromatic lenses 52, 53, 58 and 59, and also for the anamorphic mirror lens in FIG. 36, which is formed with the free-form surfaces 875, 876 and 877.

FIG. 11 shows the Michelson-Type Interferometer 603 in a further exemplary embodiment. The latter is designed in particular for at least partial operation in the VIS spectral range and/or at least partial operation in the NIR range. The input beam EB focused by an upstream lens (not shown here), with a half opening angle alpha of for example about 16 degrees, can in particular enter the beam splitter cube 622 with the beam splitter layer 62. The two partial beams TB1 and TB2 can be generated on the beam splitter layer 62, and can each be deflected by approximately 180 degrees by a prism 651 and 652 that can for example be formed as an about 90° rooftop prism. The 90° rooftop prisms 651 and 652 in particular each comprise an essentially elongated, gap-shaped gap aperture 653 and 654 or are respectively combined with the gap aperture 653 and 654. The schematic shown here illustrates that the unfolded image points O' 1e and O'2e of the measured object essentially lie respectively outside of the apparent end mirror surfaces SEF1 and SEF2 in the two arms of the Michelson-Type Interferometer 603. Here, the 90° rooftop prisms 651 and 652 are shifted laterally by slightly unequal values s1 and s2 in the same orientation in relation to the beam splitter layer 62. The resulting lateral shear s of the apparent image points O'1s and O'2s formed by the Michelson-Type Interferometer 603 after the beam unification is then determined by the difference of the values, based on the formula s=s2−s1. This resulting lateral shear s has at least approximately the same amount for all apparent image points of the measured object. If required, a very small lateral shear can in particular also be created by shifting the 90° rooftop prims 651 and 652 in the same orientation. This can in particular also be executed or realized with computer-controlled motion and control means not shown in FIG. 11. FIG. 11 schematically illustrates that even for a given location of the field of view discriminators—respectively shown here by the gap-shaped gap apertures 653 and 654—that is essentially not located in the apparent end mirror surface SEF1 and SEF2, a quite large half opening angle alpha can nevertheless be used to detect comparatively large amounts of light from the measured object, in that an input beam EB with an opening angle of for example up to 15 degrees can exist, which is however materially co-determined for the beam splitter cube by the refractive index of the employed optical materials.

FIG. 12 is a schematical illustration of a Mach-Zehnder Interferometer 604, in particular and at least partially for the MIR range, and in particular for a measured object 14 for incident light measurement. The Mach-Zehnder Interferometer 604 is for example formed as an arrangement in the form of the letter X, abbreviated as X arrangement, in particular with a beam splitter that can comprise CaF2 substrates. The angle of incidence for the main beam onto the beam splitter layer 625, on which the two partial beams TB1 and TB2 are generated is for the example shown here 38°; an angular range from 35° to 50° can also exist in particular. For each main beam in an arm of the Mach-Zehnder Interferometer 604, there is in particular a main beam essentially parallel thereto in the other arm. The correspondingly exemplary angle of incidence for the main beam onto the beam splitter layer 626 for beam unification is in this case also approximately 38°. A double mirror periscope reflector 661, preferably with two periscopes 661a and 661b is located in the arm IA1 of the Mach-Zehnder Interferometer 604, and a further double mirror periscope reflector, preferably with two periscopes 662 is likewise located in the arm IA2. Both arrangements of the periscopes 661 and 662 have a beam deflection of for example about 76°. An angular range from 70° to 100° can also exist in particular. In this case, the gap apertures 666 and 667 are each at least partially arranged between the respectively two mirrors of the periscopes 661 and 662.

In FIG. 12, the plane parallel plates 624 and 627 and the beam splitter layers 625 and 626 form a unit referred to as a beam splitter unit 620. This beam splitter unit 620 then has two elements, that is to say the plane parallel plate 624 with the beam splitter layer 625 and the plane parallel plate 627 with the beam splitter layer 626. Both elements can each split or separate and unite a light beam or a beam path. In the arrangement, the plane parallel plate 624 with the beam splitter layer 625 is designed to split the input beam EB into the partial beams TB1 and TB2, and the plane parallel plate 627 with the beam splitter layer 626 is designed to at least partially reunite the partial beams TB1 and TB2.

Given this arrangement, in particular a relatively focused image can be generated after the beam splitting on the beam splitter layer 625 in the periscope 662 in the second interferometer arm IA2. The upstream lens 73 does not necessarily need to have an opening error correction, because a tilted plate is preferably not located in the beam path upstream of the periscope 662 with the gap aperture 667 However, a relatively unfocused image of the measured object 14 is generated in the first interferometer arm IA1, because an opening error is generated therein upstream of the gap aperture 666 by the essentially tilted plates 624 and 93 located in the beam path. A gap aperture 666 slightly coarser compared to the gap aperture 667 is therefore preferably located at the point of the smallest beam constriction, the former having for example the fourfold gap width of the gap aperture 667, or 0.5 mm for the midinfrared range in the example shown here. For this reason, this interferometer arrangement is in particular suited for a comparatively coarse image resolution, which then ultimately results in a hyperspectral image that in x direction, see FIG. 10, only has about 50 resolvable image increments.

The partial beams TB1 and TB2 are then united on the beam splitter layer 626. A lateral shear s is created between the partial beams TB1 and TB2; in other words, the partial beams TB1 and TB2 are shifted in relation to each other by the value of the lateral shear s. The opening error caused by the plane parallel plates 625, 627, 93, 94 in the Mach-Zehnder Interferometer 604 is in particular at least partially corrected in the anamorphic lens 52, so that largely undisturbed cylindrical waves are formed at the output of the lens 52 that are brought to interference in the Fourier plane. In order to improve the clarity of the illustration, an illustration of the unfolded apparent image points O'1s and O'2s was omitted in FIG. 12. These are in particular created by the reverse extension of the edge beams of the partial beams TB1 and TB2. For reasons related to technical drawing, the apparent end mirror surfaces SEF1 and SEF1 and the apparent image plane SBEI12 are also not shown here in FIG. 12.

The detail FIG. 12.1 shows an example of cylindrical waves tilted toward each other with their cylindrical wave fronts 685. The detail FIG. 12.2 shows an example of a spatial interferogram rl formed on the microbolometer array 634, and the detail FIG. 12.3 is a schematic illustration of the relationship between the lateral shear s and the optical distance difference OPDr resulting at the edge of a display or a detector, in particular of a microbolometer display 634 in the detection plane DE, from which the spectral resolution can be derived, in particular calculated. For this purpose, also refer to the description in detail FIG. 4.4, which can be applied to the relationships in FIG. 12.

In an exemplary embodiment 8 (not shown schematically based on a drawing) on the basis of the arrangement in FIG. 12, a mirror in one of the double mirror periscope reflectors can be replaced by a computer-controllable micro-mirror array.

FIG. 13 is a schematic illustration of a cyclical double beam interferometer 605, in particular for at least partial operation in the FIR spectral range. The cyclical double beam interferometer 605 has a beam splitter 623, in particular with a thin mylar foil and two plane mirrors 628 and 629. In pairs, the plane mirrors 628 and 629 form at least a part of a periscope arrangement, in particular of a double mirror periscope reflector 630.

This cyclical double beam interferometer 605 is in particular also known as a Sagnac Interferometer and/or as a cyclical triangle interferometer. The arrows drawn in detail FIG. 13.1 indicate the directionality of the light of the partial beams TB1 and TB2. An essentially active, stripe-shaped illumination occurs with comparatively short light impulses—with pulse lengths in the range from several milliseconds in the low single-digit range—of a thin, moving, and at least partially transparent measured object 15 for a transmitted light measurement using a narrow IR light source 47, which has the exemplary width b_S of 1 mm, and an exemplary length of 20 mm. An illuminated stripe 80 is created on the measured object 15, which corresponds to the width b_S' of the image of the narrow IR light source 47, because in an ideal case, there is a no light scatter worth mentioning here that could cause a significant width increase of the stripe 80.

The cyclical double beam interferometer 605 as a beam splitter plane ET that is schematically shown by the beam splitter preferably with a mylar foil 623, on which in particular also the at least partial beam reunification occurs subject to the influence of the lateral shears. The straight lines g1 and g2 extended by the plane mirrors 628 and 629 intersect at the intersection SP in the reference plane RE, which in this case essentially corresponds to the drawing plane. This intersection SP, which is essentially located in the symmetry plane E_S, has a distance d_ST to the beam splitter plane ET, which in this case for example can range between approximately 0.1 mm to 7 mm and in particular between approximately 1.5 mm and 3 mm and is preferably 2.5 mm. Here, the value of 2.5 mm corresponds to about 100 wavelengths of the largest wavelength in the exemplary spectrum of 25 µm, which corresponds to a wave number of 400 cm$^{-1}$.

As shown here, two comparatively coarse field of view discriminators can be arranged at least partially between the plane mirrors 628 and 629, the field of view discriminators shown here as examples with the gap apertures 631 and 632, and which have the exemplary width of approximately b=1 mm. The width can for example also range between approximately 0.1 mm and 10 mm, and in particular between approximately 0.5 mm and 3 mm. The gap apertures 631 and 632 each contain an image O'1 respectively O'2 of the measurement point O and, as indicated in the drawing by the shift in the perspective view, are shifted slightly in the depth axis of the image This depth axis shift is in this case in particular determined from the location of the upstream lens 73, which has a certain location error in particular in the depth axis. This location error is tolerable within certain limits. It is in particular desirable that each of the images O'1 respectively O'2 of the measurement point O lie in a common plane, and that the gap apertures 631 and 632 therefore preferably also lie in a common plane This is shown in FIG. 15, where the two gap openings 677 and 678 are represented by a double gap aperture 676. The light in the FIR spectral range discriminated in FIG. 13 on the gap apertures 631 and 632 at least partially over the beam splitter 623, which in particular comprises mylar foil, reaches a detector through the anamorphic lens 53 as partial beams TB1 and TB2 propagating essentially in parallel with a lateral shear s, wherein the detector is in particular a microbolometer array 634 for interference in form of cylindrical waves tilted toward each other having the peak lines 686. This anamorphic lens 53 for example also comprises a cylindrical component 532 for at least a part of the FIR spectral range that in terms of its overall optical function principally corresponds to the lens 51. This overall function is found in the descriptions for FIG. 9 and FIG. 10. The intensity graphs of the spatial interferograms rl are shown in the detail FIG. 13.2.

The reverse extensions of the beams of the partial beams TB1 and TB2 form the largely unfolded and optically coherent apparent image points O' 1s and O'2s in the apparent image plane SBE12, which in particular also essentially corresponds to the focal plane of the lens 531 with its focal point F531.

Because there is no opening error due to the beam splitter 623, which preferably comprises a thin mylar foil, the half opening angle alpha can in this case be made comparatively large, or in particular also larger than shown here in FIG. 13, for example by 8 degrees. The maximum for the half opening angle alpha is in this case determined by the cyclical double beam interferometer—depending on the design—for example at approximately 10 degrees. The half opening angle alpha can in particular range between approximately 2 and 12 degrees, preferably between approximately 5 and 10 degrees.

Detail FIG. 13.3 is a schematic illustration of the geometric relationships at the gap apertures 631 and 632. The exemplary image of the comparatively narrow IR light source 47 has a value of approximately 2 mm for the respective widths of the light stripe b_S"1 and b_S"1. This value can in particular range between approximately 0.5 mm and 5 mm, preferably between approximately 1 mm and 3 mm. These image widths b_S"1 and b_S"2 are then less than the distance of approximately d_ST=2.5 mm, and there is essentially no optical interference between the revolving beam paths, even when the light stripe 80 is still somewhat widened by scattered light on the measured object 15 Optical interference in this case means that light content from the partial beam revolving in one direction in an undesirable manner infringes on the partial beam of the other revolving direction, and is also detected.

The detail FIG. 13.4 illustrates the situation in the apparent image plane SBE12, which is arranged upstream of every anamorphic lens 53, and is the object plane for this lens 53. The figure shows the two images 80'1 and 80'2, which are essentially located in the apparent image plane SBE12 of the light stripe 80. The widths of the two images, b_80'1 and b_80'2, in this case at least approximately correspond to the widths b_S"1 and b_S"2 created by the geometric rendering of the light source 47. When a finer local resolution is to be achieved of the measured object 15, the gap widths b can for example be reduced to 50 micrometers to 200 micrometers, and thus also the width of the light source 47.

Given a calculation example with an exemplary numerical aperture A=sin(alpha) of approximately 0.1, see detail FIG. 13.5, and given an exemplary lateral shear of approximately s=2.82*2.5 mm=7.05 mm, this results in the following exemplary maximum optical distance difference in the interferogram in the detection plane DE of lens 53, of approximately about 0.705 mm, based on the formula A*s. Given an assumed triangular apodization of the intensity values of the spatial interferogram rl when calculating the spectrum using fast Fourier transformation (FFT=fast Fourier transform), an exemplary spectral resolution of approximately 14 cm$^{-1}$ can be achieved with the reciprocal value of the optical distance difference (1/OPD), here for example approximately 1/0.705 mm. Fast Fourier-Transformation (or fast Fourier transform, and therefore typically abbreviated as FFT) is an algorithm for efficiently calculating the Discrete Fourier Transformation (DFT).

Given a comparatively small opening angle alpha, for example of less than approximately 5 degrees, in particular for example of 2 degrees to 4 degrees, and a compact construction of a cyclical interferometer 606 appropriately essentially constructed asymmetrically, it is however also possible in an exemplary embodiment 9 (not shown schematically based on a drawing) on the basis of an arrangement shown in FIG. 13 that the partial beams TB1 and TB2 do not overlap at all or at least do not overlap partially on one of the two plane mirrors of the cyclical interferometer. Different, adjacent regions of a plane mirror are then at least partially used for reflection. In this case, one of these plane mirrors 628 or 629 can in particular also be split. Each partial beam TB1 and TB2 is then at least partially mapped to a dedicated, now comparatively small plane mirror that is in particular designed to reflect the respective partial beam, and for example has a size of 5 mm×20 mm. In this case, one of the two smaller mirrors is preferably arranged somewhat shifted in the depth axis, thus creating a step in the depth axis between the two smaller plane mirrors. It is then in particular possible to introduce an additional optical distance difference in the cyclical interferometer. The objective of this is to obtain on the raster detector essentially laterally shifted spatial interferograms rl with a larger optical distance difference, which then results in an improved spectral resolution of the spectrometer. In a further exemplary embodiment 10 (not shown schematically based on a drawing), at least one of the two smaller mirrors has a comparatively very weak curvature, and therefore essentially represents a plane mirror, in order to again compensate the image shift in the depth axis created by the step. It is advantageous when in a further exemplary embodiment 11 (not shown schematically based on a drawing) both smaller mirrors have a week curvature, and the value of the curvature is at least approximately identical, wherein however one mirror is formed essentially convex and one mirror is essentially formed concave. This can in particular reduce the aberrations.

FIG. 14 is a schematic illustration of a cyclical double beam interferometer 606, in particular for at least partial operation in the VIS spectral range. The cyclical double beam interferometer 606 is preferably designed for tumor detection in tissue, and has two plane mirrors 671 and 672 that in pairs form a periscope arrangement, in particular a double mirror periscope reflector 630. On this cyclical double beam interferometer 606, the symmetry plane E_S, which also comprises the half angle line, has a parallel shift d_ST in relation to the beam splitter plane ET at least partially between the plane mirrors 671 and 672, wherein the parallel shift in this case for example ranges between approximately 0.1 mm and 5 mm, and is preferably about 1 mm, and in this case corresponds to about 1429 wavelengths of the largest wavelength of for example about 700 nm in the spectrum.

An exemplary biological measured object 16 in particular comprises fluorescent markers and is at least partially illuminated by a projected light stripe 80, at least partially in the UV spectrum, wherein the light stripe 80 is generated by a computer-controllable, raster UV light source 49. A dichroic coupling beam splitter cube 571 with a reflection surface for at least a part of the UV light couples the corresponding UV light at least partially into the illumination beam path. The raster UV light source 49 is rendered by the collimator lens 491, and the microscope lens 573 is rendered on the exemplary biological measured object 16. A luminescent pixel Xuv is then rendered onto the biological measured object 16 at least approximately focused, and shown here reduced in scale as the image Xuv' of the luminescent pixel Xuv. The width of an image Xuv' for example ranges between 6 µm and 600 µm, in particular between approximately 20 µm and 100 µm, and is preferably about 60 µm and therefore also the width of a light stripe 80, given completely or at the least partially switched on and therefore luminescent pixels. In order to reduce interference by stray light between the individual measurement points, for example the even numbered and the odd-numbered pixels can however be alternatingly illuminated, in particular for each image recorded by a camera, in particular a CMOS camera 55.

A scanner, in particular a one-dimensional, computer controllable galvano mirror scanner 572 can be used to surface-scan the measured object 16. A UV fluorescence generates light in the VIS range on the measured object 16. This fluorescent light in the VIS range can pass the coupling beam splitter cube 571 with transmissive properties of the splitter layer for fluorescent light. The remaining UV light that could at least partially still pass the coupling beam splitter cube 571 can additionally be blocked using a UV blocking filter 576, for example above approximately 700 nm. Essentially visible light then enters the cyclical interferometer 606 through the upstream lens 74. The microscope lens 573 and the upstream lens 74 in particular form a microscopic beam path with a two-fold enlargement, wherein the upstream lens 74 is in particular formed with an opening error correction for the polarizing beam splitter cube 636.

The light entering the cyclical double beam interferometer 606 therein renders at least partially in the two revolving beam paths according to the detail FIG. 14.1 the measured object 16, which is at least partially illuminated with stripes, onto a display, in particular a transmissive liquid crystal display 655 with the comparatively focused, real images O'1 and O'2 of the object point O, in an essentially focused manner. Two narrow pass-through areas 656 and 657 of approximate width b=100 µm that are separated by about 1.41*d_ST about the center distance or the distance between two centers of about 1.41 mm and that form a double gap are arranged in the liquid crystal display 655, which can be used from both sides. For this purpose, a rotation of the polarization direction of the light or no rotation of the polarization direction of the light is necessarily generated in the pass-through areas 656 and 657 of the liquid crystal display 655 addressed for the double gap. The polarization direction is in particular preserved. By contrast, a phase difference of approximately 180 degrees rotates the polarization direction by about 90°, in particular in the blocking regions of the liquid crystal display or the LCD 655. Two relatively effective, narrow pass-through areas are then created in the image plane E_BF by the interaction with the polarization analyzer 638 when the light is coupled out from the cyclical interferometer 606. In this case, the image of the light stripe 80 in the interferometer 606 at least partially covers respectively one pass-through area of the two pass-through areas 656, 657, in particular because for example a relatively narrow light stripe with an approximate width of 60 µm is created on the biological measured object 16, whose image can have an exemplary width of b_S"1 respectively b_S"1, equal to approximately 120 µm, on the liquid crystal display 655. This is shown in the detail FIG. 14.2.

The computer-controllable raster UV light source 49 is in pulse mode preferably essentially chronologically synchronized with the display, in particular the transmissive liquid crystal display 655, and is formed to control luminescent pixels that—as already discussed—are optically conjugated to a transmissive liquid crystal display 655.

The light discriminated on the pass-through areas 656 and 657 at least partially reaches the camera through the polarization beam splitter cube 636 as essentially parallel propagating partial beams TB1 and TB2 through the anamorphic lens 58, wherein the camera is in particular a CMOS camera 55, for interference in form of cylindrical waves essentially tilted toward each other, with the indicated peak lines 686

This anamorphic lens 58 is also formed with a cylindrical component, and in terms of the overall optical function principally essentially corresponds to the lens 51. The intensity graphs of the spatial interferograms rl are shown in the detail FIG. 14.3. The rearward extensions of the beams of the partial beams TB1 and TB2 form the essentially unfolded and optically coherent apparent image points O' 1s and O'2s in the apparent image plane SBE12, which in particular also essentially corresponds to the focal plane of the lens 581 with its focal point F581.

The detail FIG. 14.4 illustrates the situation in the apparent image plane SBE12, which is arranged upstream of every anamorphic lens 58, and comprises the object plane for this lens 58. The figure shows the two images 80'1 and 80'2 in the apparent image plane SBE12 of the light stripe 80. The widths of the two images, b_80'1 and b_80'2, in this case—due to scattered light—do not correspond to the widths b_S"1 and b_S"2 created by geometric rendering of the light source 47. The widths b_80'1 and b_80'2 of the images of the light stripe 80 are widened by the stray light by up to approximately 500 µm. Nevertheless, there is also in this case essentially no optical interference between the partial beams TB1 and TB2.

The detail FIG. 14.5 is a schematic illustration of the relationship between the lateral shear s and the optical distance difference OPDr resulting at the edge of the microbolometer array 634 in the detection plane DE, shown here by a camera, in particular by a CMOS camera 55 for the visible spectral range, wherein the spectral resolution can be calculated in particular from said distance difference. For this purpose, also refer to the description in detail FIG. 4.4, which can be applied to the relationships in Fig. [ . . . ]

The distance d_ST in this case is for example about 1 mm, and corresponds essentially to about 1429 wavelengths of the largest wavelength of approximately 700 nm in the spectrum.

FIG. 15 is also a schematic illustration of a cyclical double beam interferometer 607 for the visible spectral range, but in this case with two mirror prisms 679 and 680 of equal construction that are polished on all five surfaces. The mirror prisms 679 and 680 are in particular manufactured in a common operation. As a result, the dimensions can match in particular in the single-digit micrometer range, and the deviations of the prism angles from each other can also be far below one angular minute. A double gap aperture 676 with the gap openings 677 and 678 is in particular at least partially arranged between these mirror prisms 679 and 680, in particular cemented in, and which are shown in the detail FIG. 15.2. The gap widths b of these gap openings 677 and 678 are in this case comparatively large and for example range between approximately 0.05 mm and about 1 cm, in particular between approximately 0.1 mm and 0.3 mm, and are preferably about 0.2 mm. This in particular reduces the requirements for the adjustment precision, but the lateral resolution is also reduced, the latter being at least partially co-determined by the gap width b. The mirror prisms 679 and 680 of equal construction were prearranged subject to optical observation, in particular cemented. This is for example accomplished by using optical aids, in particular using an auto-collimation telescope and/or an autofocus sensor. After the adjustment, the optical distances in glass and in air are at least approximately equal in both arms IA1 and IA2. Deviations in the order of magnitude of approximately 0.02 mm are essentially still tolerable. In this case, the cyclical double-beam interferometer 607 is as a functional assembly preferably aligned laterally and in the depth axis in relation to the upstream lens 74, so that the focused partial beams TB1 and TB2 target the gap openings 677 and 678 essentially in their center or centrally.

FIG. 16 is a schematic illustration of a cyclical double beam interferometer 608, in particular for at least partial operation in the MIR spectral range with an active illumination by means of a narrow IR light source 47, in particular for stripe-shaped illumination of the measured object 15 to measure in transmission in the near range. The cyclical double beam interferometer 608 in particular comprises two plane mirrors 628 and 629. In pairs, the plane mirrors 628 and 629 form a periscope arrangement, in particular a double mirror periscope reflector 630. In particular, a detector can be used in this example that comprises a raster detector, preferably a microbolometer array 59.

A beam splitter that in this case preferably comprises a plate beam splitter with the plates 673 and 675 and the beam splitter layer 674, can generate an astigmatism and coma. These aberrations are in particular compensated with regard to an opening area by a plate 92 preferably having a thickness that corresponds to the sum of the thickness of the plates 673 and 674 (of equal thickness), wherein the opening area can preferably already be corrected in the upstream lens 74. An essentially focused image of the measured object 15 can then be generated in the image plane E_BF, where the double gap aperture 676 is located and each gap opening 677 and 678 forms a field of view discriminator.

Imaging errors, in particular such as astigmatism and coma of the plates 673 and 675 are compensated with regard to an opening area preferably at the output of the interferometer 608, in particular by a plate 95 with a thickness that corresponds to the sum of the thicknesses of the plate 673 and 675 of equal thickness, wherein the opening area can already be corrected in the downstream anamorphic lens 59, wherein the downstream anamorphic lens can preferably in addition to the opening error correction also have a field correction. An illustration of the unfolded apparent image points O'1s and O'2s was omitted in FIG. 16.

The arrangement in FIG. 17, which is designed for the mid-infrared spectral range, at least partially corresponds to the elements in the embodiment shown in FIG. 16. But the arrangement shown here is a double mirror prism arrangement 683 in the cyclical double beam interferometer 612 with two mirror prisms 761 and 763, in particular made of CaF2, that is therefore designed for the mid-infrared spectral range. Furthermore, in the arrangement or embodiment in FIG. 17, e.g. a plane plate group 668 is inserted in the beam path of the cyclical double beam interferometer 612 in region Z, in particular for adjusting and/or influencing the optical distance difference OPD_zykaP, for the purpose of having the ability to enlarge the optical distance difference. This plane plate group 668 is for example also shown in FIG. 18a, wherein the plane plate group 668 in particular comprises two plane parallel plates 765 and 766 that each comprise ZnSe.

The plane plate group 668 for adjusting and/or influencing the optical distance difference OPD_zykaP can be used to generate asymmetrical spatial interferograms rl on a detector, in particular a microbolometer array 634. This is for example also shown in the detail FIG. 17.2 with the maximum optical distance difference OPD_left on the left side of the spatial interferogram rl and the maximum optical distance difference OPD_right on the right side of the spatial interferogram rl. Spatial interferograms formed somewhat biased to one side on the microbolometer array 634 (see detail FIG. 17.3) at least partially permit a somewhat higher spectral resolution due to the now larger optical distance difference OPDru at the edge of the detector, which can comprise a microbolometer array 634. It is noteworthy in this case that due to the effect of the plane plate group 668 for adjusting and/or influencing the optical distance difference OPD_zykaP, the apparent image points O'1s and O'2s do not exactly lie in a common plane, and that there are deviations of several $\frac{1}{10}$ millimeters, and that there is therefore also in particular no common apparent image plane. Within limits, this may be tolerable when the image location difference in the depth axis delta_v is significantly below the optical wave depth of field focal range for the shortest wavelength in at least a part of the employed spectrum. Notable and interfering nonlinearities are created in the spatial interferograms rl for larger image location differences, or for example significantly above 100 µm.

OPD_zykaP in particular represents an additional optical distance difference that is created in particular by inserting at least one plane parallel plate each into every partial beam TB1 and TB2 in the region Z in a cyclical double beam interferometer, where the spaces of the partial beams essentially do not overlap.

FIG. 18a is a schematic illustration of the optical effect of the plane plate group 668 for adjusting and/or influencing the optical distance difference OPD_zykaP. This plane plate group 668 is in this case in particular formed for operation in at least a partial range of the MIR spectral range, and has two plane parallel plates 765 and 766 that are essentially of different thickness, exposed, and at least partially transparent for the MIR spectral range, the plane parallel plates having the exemplary thicknesses between respectively approximately 0.2 mm and 5 mm, in particular between approximately 0.7 mm and 2 mm, preferably of approximately h1=1 mm and h2=0.9 mm. The plane parallel plates 765 and 766 preferably comprise at least partially the respectively same optical material, that is to say in particular zinc-selenium (ZnSe), with the approximate refractive index of n1=2.43 at an approximate wavelength of 5 µm. Each plane parallel plate 765 and 766 comprises a gap aperture 631 and 632 and/or is mapped to a gap aperture 631 and 632. The plane parallel plates 765 and 766 essentially lie at different positions along the depth axis in the beam path. This plane plate group 668 is used to purposefully generate an additional optical distance difference OPD_zykaP in the cyclical double beam interferometer.

The optical distance difference OPD_zykaP is in particular calculated with the equation (9):

$$OPD\_zykaP = \text{value}[n1*(h1-h2)] \qquad \text{Equation (9)}$$

The respective thicknesses of the plane parallel plates 765 and 766 are in this case in particular approximately 0.2 mm to 5 mm, in particular approximately 0.7 mm to 2 mm, and the thickness of a plane parallel plate 765 is preferably h1=1 mm, and the thickness of the plane parallel plate 766 is preferably h2=0.9 mm, and the refractive index n1 of ZnSe is specified at approximately n1=2.43 at a wavelength of approximately 5 µm, based on which a value for OPD_zykaP of approximately 243 µm is determined by equation (9). This results in a preferred lateral shear of the spatial interferograms rl on the chip of the spatial detector, for example on the microbolometer array 634. The image location difference in the depth axis d is in this case in particular determined with the equation (10)

$$\text{delta}\_v = (h1-h2)*(n1-1)/n1 \qquad \text{Equation (10)}$$

or an approximate value of 59 µm. Given a spectrum above approximately 5 µm and a numerical aperture of a downstream anamorphic imaging stage that is in particularly less than approximately 1, preferably less than approximately 0.5, and particularly preferably approximately 0.2, and that does not yet exhibit noticeable nonlinearities in the spatial interferograms rl, this value generates [ . . . . ]. The arrangement in FIG. 18a in particular causes and in and of itself undesirable image shift in the depth axis delta_v. However, the latter principally cannot be completely compensated with two plane parallel plates having a same refractive index n1.

No complete compensation of the image shifts in the depth axis can be achieved with the two plane parallel plates 765 and 766 in FIG. 18a. FIG. 18b shows that an image location difference in the depth axis delta_v at all times remains. The apparent image planes SBE1 and SBE2 then do not coincide, and there is no common apparent image plane SBE12.

By contrast, FIG. 19a is a schematic illustration of a plane plate group 669, in particular for purposefully influencing the optical distance difference OPD_zykaP, which can affect an essentially complete compensation of the image shifts in the depth axis. Here too, at least a part of the MIR range is addressed. In this case, the plane plate group 669 comprises two essentially exposed, transparent plane parallel plates 767 and 768 of different thickness, each with different optical materials, with a thickness h1 and the refractive index n1 for the plane parallel plate 767 and the thickness h2 and the refractive index n2 for the plane parallel plate 768 respectively. Each plane parallel plate 767 and 768 is respectively mapped to a gap aperture 631 and 632 with the gap openings 677 and 678, or each plane parallel plate 767 and 768 respectively has a gap aperture 631 and 632 with the gap openings 677 and 678. These gap apertures 631 and 632 in particular lie in the beam path at essentially the same position along the depth axis and coincide with the image planes BEI1 and BEI2 respectively. In this case, the first plane parallel plate 767 comprises calcium fluoride (CaF2) with the approximate refractive index of n1=1.399 at a wavelength of approximately 5 µm, and the second plane parallel plate 768 comprises zinc selenium (ZnSe) with the same refractive index of approximately n2=2.43 at essentially the same wavelength. The illustration shown here is not (necessarily) true to scale. The height differential h1−h2 between the two plane parallel plates 767 and 768 and the specified refractive indexes n1 and n2 of the optical materials of the plane parallel plates 767 and 768 by way of the resulting OPD_zykaP determine the lateral shear of the spatial interferogram rl on the microbolometer array 634, so that an asymmetric location of the spatial interferograms rl can be preferably generated thereon.

The plane plate group 669 in FIG. 19a can be used to achieve an essentially complete compensation of the image shifts in the depth axis, in particular when the thickness h2 is determined for a given thickness h1 and the given refractive indexes n1 and n2 using the already specified equation (2) after converting the latter to the equation (11)

$$h2 = h1*[(n1-1)*n2]/[(n2-1)*n1] \qquad \text{Equation (11)}$$

Given a plate thickness of approximately h1=1 mm and the specified refractive indexes n1 and n2, this equation (11) results in a plate thickness of approximately h2=0.4846 mm, and a value for OPD_zykaP of approximately 220 µm based on Equation (3). The coherent image points O'1s and O'2s generated from a measurement point O can then ultimately be brought into a common apparent image plane SBE12 by a corresponding focus location variation of an upstream lens that is not shown here. This is shown in FIG. 19b.

FIG. 20 to FIG. 27 show schematic illustrations of cyclical double-beam interferometers 609, 610, 611, 613 and 614 on which the main beams of the partial beams TB1 and TB2 each have an angle of less than approximately 90 degrees, in this case approximately 76 degrees in relation to each other after the beam splitting. This is in particular intended for a preferred shortening of the optical distance OPL in the cyclical double beam interferometer in comparison to an arrangement with approximately 90 degrees between the main beams and the partial beams TB1 and TB2. A slightly larger aperture angle can then principally be achieved in the refractive material. For reasons of clarity, all illustrations in FIG. 20 to FIG. 27 in this case omitted an illustration of the apparent image plane SBE12.

FIG. 20 is a schematic illustration of a cyclical double beam interferometer 609 that comprises four prims 690, 691, 687 and 688 that are joined or arranged together, in particular cemented together. The two triangle prims 690 and 691 and the two mirror prisms 687 and 688 are each essentially of equal construction because these can preferably each be manufactured in pairs in a single manufacturing operation. The mirror prisms 687 and 688 each have an angle psi respectively between the mirror surface 687s and the mirror surface 688s and a nonreflective surface. A throat-shaped airgap is formed between the two mirror prisms 687 and 688 in which the double gap aperture 676 is preferably securely arranged in the common image plane BEI12.

For each of the four prisms 687, 688, 690 and 691, the beam entrance for the main beam is preferably at least approximately vertical. The arrangement is in this case based on a relatively acute half angle psi of approximately 26 degrees, from which all the relevant angles of the four prisms 690, 691, 687 and 688 are determined when an essentially vertical beam entry and beam exit of the main beams is to be achieved on all surfaces.

During assembly subject to optical observation, the mirror prism 687 can preferably be arranged or cemented as the last mirror prism. The lateral shear s is then adjustable once in particular with a precision shift of the mirror prism 687 and can also be adjusted in relation to the double gap aperture 676 which is then also fixed once, in this regard also refer FIG. 22. The target value for the distance a of the gap openings of the double gap aperture 676 is approximately half the lateral shear s. The deep-black double gap aperture 676 is shown in the detail FIG. 20.2, and in this case in particular comprises nano-structured surfaces for reflex suppression.

In a preferred precision fabrication, a person skilled in the art can calculate the preferred or suited and/or required center distance of the gap openings of a double gap aperture 676 after cementing the four prisms 687, 688, 690, and 691 of the cyclical double beam interferometer 609 with the angle psi of 26 degrees from the spatial frequency of the interference pattern, given a reference wavelength that can be measured on a chip in the focal plane of a downstream measured object. The precision fabrication can be executed by computer-control using 3-D printing.

FIG. 21 is a schematic illustration of a further cyclical double beam interferometer 610 that has four prisms 687, 688, 690 and 691 of which the two triangle prisms 690 and 691 and the two mirror prisms 687 and 688 are preferably and essentially of equal construction. In this case, there is in particular no air gap. A thin, deep-black double gap aperture 694 with a thickness of only a few micro meters can preferably be applied onto and cemented into the common image plane BEI12 on the mirror prism 688. This double gap aperture 694 is in this case preferably formed with comparatively wide gap openings with a size ranging between approximately 0.05 mm and 0.8 mm, in particular between approximately 0.1 and 0.3, and preferably is about b=0.2 mm.

FIG. 22 is a general illustration of the angle relationships for the cyclical double beam interferometer 609 and 610, which can be derived from a specified half angle psi, for the purpose of achieving a generally and essentially vertical beam entrance and beam exit for the main beams HTB1 and HTB2 of the two partial beams TB1 and TB2. The angle psi on the two mirror prisms 687 and 688 is in this case respectively created between an essentially nonreflective and the essentially reflective surface 687s and the essentially reflective surface 688s respectively. The angle psi is in this case then at least approximately created twice on each of the two mirror prisms 687 and 688. The angle 2rho, with approximately rho=90°-psi, is the obtuse angle respectively between the two essentially non-reflective surfaces of the mirror prisms 687 and 688 used in the interferometric beam path. The angle created on the beam splitter surface of the two triangle prisms 690 and 691 with triangular face respectively has the angle 2 psi.

FIG. 23 schematically illustrates the effect of a parallel shift of the mirror prisms 687, in particular for a onetime adjustment, e.g. when cementing with observation. Due to the vertical beam entrance and beam exit, the parallel shift does not change the optical distances. However, the main beam is shifted by delta_a essentially parallel in relation to the beam splitter plane ET. Firstly, this guarantees the essentially vertical beam entrance and exit of the main beams HTB1 and HTB2 of the partial beams TB1 and TB2. Secondly, this can simplify adjusting the location of the field of view discriminators in relation to the image point O'1 of the measured object since this eliminates the need to refocus the upstream lens after each adjustment step in the cement. The half-angle line of the obtuse angle 2rho is essentially parallel to the plumb line go of the opposing essentially reflective surface of the mirror prism 687. The beam deflection angle has the value 2 psi on the mirror prism 687, which applies likewise for the mirror prism 688 of equal construction.

FIG. 24 is a schematic illustration of a cyclical double beam interferometer 611 that essentially comprises three adjoining, in particular cemented together components, that is to say a triangle prism 690 and two mirror prisms 689 and 687. Thereof, the two mirror prisms 689 and 687 have the in particular essentially same angle psi of approximately 10° to approximately 50°, in particular from approximately 20° to approximately 30°, and preferably of approximately 26°. The lateral shear s is not variably adjustable which can represent an advantage for the ruggedness of the arrangement. The angles stated here result on the cyclical double beam interferometer 611 when for example psi is equal to approximately 26 degrees. The beam deflection angle on the two mirror prisms 689 and 687 in particular for example has the approximate value of 2 psi=52 degrees respectively.

FIG. 25 shows the generalized angle relationships that result from the essentially acute half angle psi for an arrangement with three cemented together components, that is to say a triangle prism 690 and the two mirror prisms 689 and 687, in order to also here generally achieve a vertical beam entrance and beam exit for the main beams HTB1 and HTB2 of the two partial beams TB1 and TB2.

FIG. 26 is a schematic illustration of a cyclical double beam interferometer 613 that comprises mirror prisms 887 and 889 that can each comprise zinc selenium. The transmission surfaces are non-reflective. A beam splitter 623 made of mylar foil is used for beam splitting. The detail FIGS. 26.2 and 26.3 show the mirror prisms 887 and 889 whose heights d1 and d2 are made as equal as possible. In the example in FIG. 26, the required double gap aperture 676 in the common image plane BEI12 is fabricated to size with regard to the required center distance of the gap openings a after the arrangement is assembled.

FIG. 27 is a schematic illustration of a cyclical double beam interferometer 614, in particular for at least partial operation in the VIS and/or in the NIR range. The illustration of the upstream lens and a downstream anamorphic lens was omitted. This cyclical double beam interferometer 614 comprises two mirror prisms 689 and 696 having the same angles and construction that form the [ . . . ] 697, and a plane parallel plate 698 arranged, in particular cemented into, the double beam interferometer 614, for example comprising the thickness of approximately 2 mm, onto or on which the beam splitter layer 62 is arranged. These mirror prisms 689 and 696 respectively comprise a first acute angle psi, a second acute angle 2 psi, and a third angle with the value 180 degrees minus 3 psi; as a result, in particular at least three angles on the two mirror prisms respectively essentially match. The mirror prisms 689 and 696 preferably have an acute angle of approximately psi=26 degrees.

The distance d_ST between the intersection SP from the beam splitter plane ET generates a lateral shear s and is for example approximately 2 mm. The distance d_ST can generally range between approximately 0.1 mm and approximately 5 mm, in particular between approximately 1 mm and approximately 3 mm, and preferably between approximately 1.5 mm and approximately 2.5 mm. A plane plate group 670a is arranged or embedded in the gap that is filled with air, in particular representing an air gap, for the purpose of adjusting the optical distance difference OPD_zykaP with an essentially complete compensation of the image shift in the depth axis. This is in particular intended to obtain spatial interferograms rl shifted in the detection plane DE (see detail FIG. 27.2), in particular to obtain or achieve a highest possible spectral resolution. The plane plate group 670a can be fabricated to size after the arrangement is assembled, for example after cementing the cyclical double beam interferometer 614 after the latter is measured optically.

FIG. 28a is a schematic illustration of a plane plate group 670a, in particular for adjusting the optical distance difference OPD_zykaP with an essentially complete compensation of the image shift in the depth axis between the two partial beams TB1 and TB2. In particular for operation in at least a partial range of the VIS and/or the NIR range, the plane plate group 670a as at least partially transparent layers, in particular transparent cement layers, and comprises two at least partially transparent plane parallel plates 971 and 972 of essentially different thicknesses, comprising the different thicknesses h1 and h2. The thickness h1 is for example approximately 2 mm. The thickness h1 can generally range between approximately 0.1 mm and approximately 5 mm, in particular between approximately 1 mm and approximately 3 mm, and preferably between approximately 1.5 mm and approximately 2.5 mm. The two plane parallel plates 971 and 972 preferably comprise two different glass types, for example borosilicate glass BK7 and dense crown glass N-SK4, each comprising different refractive indexes of approximately n1=1.507 for BK7 and of approximately n2=1.601 for dense crown glass N-SK4 at the respective wavelength of approximately 1000 nm. These plane parallel plates 971 and 972 are optically arranged, in particular cemented onto, a common plane parallel carrier plate 973 The carrier plate 973 also has the refractive index n1 and the thickness h1. A double gap aperture 975 is arranged whose first gap opening 976 is mapped to the first plane parallel plate 971 and whose second gap opening 977 is mapped to the second plane parallel plate 972. This arrangement is intended to purposefully generate an optical distance difference OPD_zykaP in the cyclical double beam interferometer. The heights h1 and h2 of both plane parallel plates 971 and 972, respectively comprising different refractive indexes n1 and n2, are significant for, or determine, the resulting distance difference OPD_zykaP and ultimately the lateral shear of the spatial interferograms in the detection plane DE, that is to say on the sensor surface of a detector, in particular a raster detector, so that an essentially asymmetric location of the spatial interferograms rl is created thereon.

The respective arrangement in the FIG. 28a and FIG. 29 causes no essentially different image shift in the depth axis, so that the difference of the image shifts delta_v is essentially zero, and that an approximately complete compensation of the individual image shifts can then be achieved Given the thickness h1 of for example approximately 2 mm, and given the refractive indexes of approximately n1=1.507 and of approximately n2=1.601, the value of h2 is in this case determined with equation (11) at approximately h2=1.792 mm. The coherent image points O'1 and O'2 generated by a measurement point O can then ultimately be brought into a common apparent image plane SBE12 by varying the focus location of an upstream lens. Based on the equation (3), the optical distance difference OPD_zykaP is then for example in this case approximately OPD_zykaP=144 µm. The known and rather undesirable chirping effect in the spatial interferograms rl due to the somewhat different dispersion in the two optical glass elements (combined here) can be comparatively easily rendered without influence on the calculated spectrum by persons trained in the art with a phase correction when calculating the spectrums.

A complete compensation of the image shifts delta_v in the depth axis can be achieved with the three plane parallel plates 971, 972 and 973 from FIG. 28a, see FIG. 28b. The latter shows that an image location difference of delta_v=0 can be achieved. A common apparent image plane SBE12 is then created.

FIG. 29 is a schematic illustration of a plane plate group 670b, comprising a carrier plate 974. The latter for example has the thickness h2 and the aforementioned refractive index n2, wherein the latter is preferably higher than the refractive index n1. As a result, the plane plate 670b can be preferably formed with a slightly lower thickness in comparison to the plane plate group 670a in FIG. 28a.

FIG. 30 is a schematic illustration of a cyclical interferometer 615 that is designed for at least partial operation in the far infrared spectral range, and that is in particular formed with an acute half angle of for example approximately 25 degrees. A double mirrored staircase 85 is arranged between the two gap apertures 631 and 632, shown in the detail FIG. 30.1, which respectively illustrate a field of view discriminator BFD, in the region Z where the partial beams TB1 and TB2 essentially do not overlap. The double mirrored staircase 85 is shown in the detail FIG. 30.1 and comprises a first mirrored staircase 82 and a second mirrored staircase 83. This double mirrored staircase 85 also comprises a center web 84, in particular comprising a metal (see detail FIG. 30.2), with the two plane mirrors 822 and 832 that are respectively manufactured or fabricated on the center web 84 by means of single point diamond machining. The center web 84 is in particular a part of a metal element, in particular of a monolith comprising copper. The four plane mirrors 821, 822, 831 and 832 of the double mirrored staircase 85 in particular are formed for at least partial operation in the far infrared spectral range with a layer comprising gold, in particular with a pure gold layer. The mirror distances dm_1 and dm_2 in the double mirrored staircase 85 are preferably formed or manufactured with a difference of approximately 0.02 mm to approximately 0.5 mm, in particular from approximately 0.1 mm to approximately 0.2 mm, preferably of approximately 0.15 mm This in particular results in an additional optical distance difference OPD_zykaS that then results by inserting one mirrored staircase 82 and 83 respectively into each partial beam TB1 and TB2 in a cyclical double beam interferometer, where the spaces of the partial beams do not overlap in region Z. This additional optical distance difference OPD_zykS is preferably less than the wave-optical depth of field focal range of the partial beams TB1 and TB2 for the smallest wavelength in the measured spectrum. The additional optical distance difference OPD_zykaS is created in particular by an angle of incidence of approximately 45 degrees on the plane mirrors 821, 822, 831 and 832 and in particular the mirror distances dm_1 and dm_2 in the double mirrored staircase 85 with a difference of 0.15 mm, with approximately OPD_zykaS=0.42 mm in the spatial interferogram rI.

A spatial interferogram rl is then essentially respectively formed in the detection plane DE with a lateral shear and comprises an essentially asymmetrical location on the raster detector that is not shown here. In this case, this results in a maximum achievable optical distance difference OPDru at the edge of the raster detector in the order of magnitude of approximately 1 mm, for example between approximately 0.1 mm and 5 mm, in particular between approximately 0.8 mm and approximately 1.2 mm. Such an arrangement can in particular also be used to examine an essentially expanded self-luminescent object, for example a fluorescing light source, because in this case, an optical interference between the two partial beam paths in the interferometer 615 is reduced or even avoided by the geometric embodiment, in particular also by the arrangement of an upstream aperture 861 in combination with the gap apertures 631 and 632. An optical interference can be caused by an expanding luminescent object whose coherent images are likewise laterally expanded after the beam splitting such that image points from the first partial beam TB1 enter the beam path of the partial beam TB2 in the region of the double mirrored staircase 85, and vice versa. The upstream aperture 861 reduces the lateral expansion of the incident beam EB.

A cyclical interferometer 615 with an essentially acute half angle of for example approximately 25 degrees and with a double mirrored staircase 85, comprising a center web 84, permits a particularly large aperture angle in comparison to two separate mirrored staircases of typically up to approximately 5 degrees, in particular up to approximately 7 degrees, and preferably up to approximately 10 degrees, because the two plane mirrors 822 and 832 can be arranged spatially particularly close to each other on the center web 84. The detail FIG. 30.2 is a schematic illustration of the comparably thin center web 84, comprising the two-plane mirror surfaces 822 and 832. Moreover, the precision manufacturing of the double mirrored staircase 85, which can be manufactured in a single operation by single point diamond machining on an ultra-precision machine, permits that the deviation from rectangularity in relation to a common plane of the four plane mirrors 821, 822, 831 and 832 of the double mirrored staircase 85 essentially approaches zero, or is for example less than 10 angular seconds. An angular second represents 1/3600 of a degree, which in turn represents 1/360 of the full circle. This small deviation from rectangularity can in particular improve the function of the cyclical interferometer 615 in that the common plane of the four plane mirrors 821, 822, 831 and 832 can be adjusted to be parallel in relation to the reference plane RE, likewise with maximum deviations from parallelity of for example 10 angular seconds. This minimizes undesirable loss of contrast in the spatial interferograms rl. The detail FIG. 30.3 represents the lateral shear of the spatial interferogram in the detection plane DE on the basis of the effect of the double mirrored staircase 85.

Two essentially separate and intrinsically rigid mirrored staircases 82 and 83 that are at least partially shifted in the depth axis are arranged in FIG. 31 Separating the two mirrored staircases 82 and 83 also permits a rotation of one mirrored staircase, here the mirrored staircase 82, in order to enable a precision adjustment of the optical distance difference OPD_zykaS, in particular by rotating the former. By means of an arrangement shown in FIG. 31, an expanded, self-luminescent object can also be examined, because an optical interference between the partial beam paths is practically not possible.

FIG. 32 shows a double mirrored staircase 85w with a bent beam path. For better clarity, the illustration of the double mirrored staircase 85w was in this case drawn with the angles tau_1 and tau_2 of for example approximately 6 degrees respectively. In a typical arrangement, these angles are typically however relatively small angles, such as approximately 3 degrees. The angle kappa for describing the beam bending with the equation (1) is therefore approximately 180 degrees-24°=156 degrees FIG. 33 shows a cyclical double beam interferometer 615 with a double mirrored staircase 85w that has a bent beam path with a deflection angle of approximately 6 degrees. The illustration shows tau_1=tau_2=3 degrees. Based on the equation (1), the angle kappa is in this case approximately 168 degrees. This bending of the two beam paths permits a larger aperture angle alpha, such as approximately 12 degrees, in particular when a foil beam splitter 86 with a negligible thickness is used, based on which aberrations on the beam splitter are also avoided. This aperture angle alpha of approximately 12 degrees represents a comparatively relatively large value for a cyclical double beam interferometer, and permits a correspondingly high light throughput through the cyclical double beam interferometer 615.

FIG. 34 shows a double mirrored staircase 85 on which the two outer plane mirrors 821s and 831s are essentially formed so narrowly that these can themselves act as field of view discriminators. The auxiliary apertures 633 can prevent an optical interference. Field of view discriminators arranged as gap apertures can then in particular be omitted. Detail FIG. 34 is a schematic illustration of the center web 84 with the two plane mirrors 822 and 832.

FIG. 35 is a schematic all illustration of an arrangement with two separated mirrored staircases, that is to say a first mirrored staircase 82 and a second mirrored staircase 83. On this arrangement, the second plane mirror 822s of the first mirrored staircase 82, see detail FIG. 34, and also the second plane mirror 832s of the second mirrored staircase 83 are formed narrow, and the latter can then respectively by themselves act as field of view discriminators. The auxiliary apertures 633 can moreover reduce and in particular prevent an optical interference. Detail FIG. 35 is a schematic illustration of the first mirrored staircase 82 with the relatively narrowly formed plane mirror 822s, which in this case acts as a field of view discriminator. Due to the long wavelengths, in particular between approximately 50 μm and 1000 μm in the far infrared spectral range, the tilt of the relatively narrowly formed plane mirror 822s, that is to say for example in the range of several 10th millimeters up to several millimeters in the lower FIR range, is in this case readily tolerable in the beam path because the wave-optical depth of field focal range is comparatively large in this case.

FIG. 36 shows a symmetrically constructed cyclical double beam interferometer 616 on which the distance d_ST of the intersection SP from the beam splitter plane ET is approximately equal to zero. The lateral shear s is in particular generated by the double mirrored staircase 85, which is shown in the detail FIG. 36.1. Due to the essentially unequal mirror distances of the plane mirrors 821 and 822 and 831 and 832 (not shown here), the position of the spatial interferograms rl on the raster detector is slightly shifted, which is shown in the detail FIG. 36.3.

FIG. 37 is a schematic illustration of an exhaust cloud 16, in particular of a flowing hot exhaust cloud 16 positioned over a factory plant, in particular with a larger distance from the factory plant, at the time t1, that is in this case moving from left to right, and in this case is to be examined spectrally in the far infrared range (FIR) and also to be examined spatially resolved. In order to analyze the hot exhaust cloud 16, an arrangement 870 with mirror optics and with a cyclical double beam interferometer 615 is for this purpose used in the spectrometer system, which can for example be positioned at ground level. This arrangement 870 has an upstream lens 751 to focus the arriving rays, wherein the lens is formed with the reflective free-form surface 872 on the mirror block 871 and the first reflective free-form surface 874 on the mirror block 873. The mirror block 871 is in this case shown at a reduced scale.

After passing the free-form surface 874, the rays enter the cyclical double beam interferometer 615. The interfering partial beams enter the downstream anamorphic lens, which is in this case formed with the reflective free-form surfaces 875, 876 and 877. The reflective free-form surfaces 875, 876 and 877 form an anamorphic lens 595 that is arranged downstream of the cyclical double beam interferometer 615 and arranged upstream of the microbolometer array 634. The spatial interferograms rl are then ultimately formed on the microbolometer array 634 after the beam formation of partial beams TB1 and TB2 using the second free-form surface 875, formed on the mirror block 871, and using the fourth free-form surface 876, which is formed as a saddle surface on the mirror block 871, and using the third free-form surface 877 of the mirror block 871, which represents in total the fifth free-form surface. These spatial interferograms rl are shown in the detail FIG. 36.3 for the times t1 and t2.

In this case, the image information about the exhaust cloud 16 plays a rather subordinated role for the measurement and analysis, because the object shape of the latter is of only minor interest for the analysis of air pollutants. Instead, the objective is to approximately determine the spectral composition based on the spatial resolution, which permits conclusions about hazardous components in particular for humans, animals, and the environment. However, under no circumstances must significant spectral information that for example signifies toxic components be overlooked or not recorded. It is initially not of uppermost interest where these toxic components are exactly localized in the exhaust cloud. It is already sufficient when the spectral information that signifies hazardous substances can at least be mapped to a single exhaust stack, for example based on knowledge of the current wind direction.

The detail figure A, which in this case shows this cyclical double beam interferometer 615 in the detail FIG. 37.1, corresponds to that in FIG. 30. The double mirrored staircase 85 arranged here is shown in the detail FIG. 37.2, and corresponds to the detail FIG. 30.1 in FIG. 30. The description of the double mirrored staircase 85 corresponds to that in detail FIG. 30.1.

The following is a detailed discussion, description, and/or definition of the employed terminology.

The term lateral shear is based on the phenomenon of interference between two reflecting light beams with lateral shift, that is to say transversal shift. In conventional arrangements, this typically involves reflecting a light beam under test on an outer surface and a light beam on an inner surface of a shear plate such that they are reflected spatially (and chronologically) shifted in relation to each other. A lateral shear can in particular be typically generated with a shear interferometer, wherein the shear interferometer is an optically comparatively simple device in the form of a plate for the purpose of conducting a wave front analysis. It can be used to test the collimation of light beams, in particular of laser sources, whose coherence length is generally significantly greater than twice the optical thickness of the shear plate. The shear interferometer, which is formed as a plate, typically comprises an essentially high-value optical glass, such as N-BK7 or also quartz glass with particularly planar and smooth optical surfaces, that are normally arranged at a very small angle in relation to each other, and are therefore arranged essentially not parallel in relation to each other, and therefore have a very weak wedge-shaped character. During the test, a properly collimated beam, is incident on the shear interferometer in the form of a plate at an angle of approximately 45°, and is reflected twice. Due to the weak wedge-shaped character, the two reflected light beams are slightly tilted toward each other after passing the plate, and given perfect collimation of the input beam (planar wavefront), exhibit interference stripes downstream of the shear plate that are typically oriented in parallel to the lateral shear, given perfect collimation. This separation or lateral shift of the beams generated by the shear plate is referred to as shear, in particular as lateral shear. The lateral shear can also be generated by lattices or, as in the present case, by a suitable mirror element, in particular by a double mirror periscope reflector with a field of view discriminator unit according to the invention. Lateral shear is indicated in the respective drawings with the referenced symbol "s".

The term "double beam interferometer" in particular comprises double beam interferometer types, such as a Michelson-Type Interferometer, a Mach-Zehnder Interferometer, or a cyclical double beam interferometer.

In this document, the term "light" is used as a synonym for electromagnetic radiation, that is to say in particular for the UV range up to the terahertz range.

The acronym FIR in particular refers to the far infrared spectral range, wherein the latter in particular lies approximately between 50 μm and 1000 μm.

On a Michelson-Type Interferometer, the outbound and the return beam in particular at least approximately propagate in parallel to each other in each interferometer arm, and the beam splitting and beam unification in particular occur on the same beam splitter surface. The term "Michelson-Type Interferometer" is herein predominately used in lieu of "Michelson Interferometer" because the arrangements described herein in particular have more than one plane mirror in the interferometer arms IA1 and IA2, thus not referring to a pure "Michelson Interferometer" in the strict sense.

The acronym MIR in particular refers to the midinfrared range, which in particular lies between approximately 3 μm and 50 μm.

The acronym NIR in particular refers to the near infrared range, which in particular lies between approximately 0.78 μm and 3 μm, and is split into the IR-A range between approximately 0.78 μm and 1.4 μm, and the IR-B range between approximately 1.4 μm and 3 μm.

The acronym SEF in particular refers to an apparent end mirror surface that results after the unfolding of mirrored surfaces.

The acronym VEIS in particular refers to the visual spectral range, or to the spectral range visible to the human eye, between approximately 380 nm and 780 nm, in particular between approximately 400 nm to 700 nm.

A double mirror periscope reflector can in particular be formed as a 90-degree rooftop reflector, but also as a periscope reflector with 45-degree beam deflection. Angular beam deflection values between approximately 40 degrees and approximately 150 degrees, in particular between approximately 60 degrees and approximately 120 degrees are preferably possible.

A field of view discriminator is in particular an opening in an aperture, wherein the opening preferably is a gap aperture 645, a pinhole, a pinhole array that comprises a plurality of pinholes, and/or a pass-through area 656, 657 of a liquid crystal display 655.

A nondiscriminating area of a field of view discriminator for example comprises the pass-through area on a gap-shaped field of view discriminator, that is to say in the simplest case the gap opening and/or the reflecting area, for example in a very narrow plane mirror as a field of view discriminator. The nondiscriminating area can also be represented by a spatial light modulator in transmission (liquid crystal display) or in reflection (digital micro-mirror array). The nondiscriminating area can also exhibit a fine structuring.

A field of view discriminator can in particular also have a narrow reflective area on a plane mirror and/or on a micro-mirror array, and/or also a narrow plane mirror.

The specified forms of a field of view discriminator are in particular designed to allow at least a part of a light beam to pass on a well-defined beam path into the further section of the beam path, most preferably in the form of a narrow stripe that preferably can correspond to a tenth up to a thousandth of the extent of the image, for example one tenth up to one thousandths of the height of the image of the measured object in the double beam interferometer. The de facto "one-dimensionality" of the narrow stripe—with image elements preferably in only a single line—ultimately permits generating respectively exactly one spatial interferogram from each of the image elements still remaining after selection. In other words, in particular those parts of a light beam are hidden or blocked by the field of view discriminators that are not intended to follow the predetermined beam path. The field of view discriminator can for example also be used to hide or block scattered light. This means that scattered light is prevented from passing the field of view discriminator in the further section of the beam path. The term "spatial selection" refers to the selection or to the passing of the light that can pass or fall through the field of view discriminator, for example the gap, and is ultimately detected. In other words, not only the field of view is selected, but the stray light undesired in this case is minimized.

A mirror prism, which is herein alternatively also called prism, in particular has a refractive material, such as $CaF_2$, Si, BK7, quartz glass, crystalline quartz, and/or other commonly used optical materials for the desired spectral ranges. The mirror prism can be at least partially coated or can also be completely uncoated. The mirror prism in particular has at least one entrance and/or exit surface suited for the entrance and/or exit of a light beam. The mirror prism in particular also has at least one reflection surface or a mirror surface that under suitable conditions is designed to reflect or mirror at least a part of the light beam entering the prism. An essentially complete reflection can occur in particular at angles of total reflection. The mirror prism can in particular also have a second reflection surface or a mirror surface that under suitable conditions is designed to reflect or mirror at least a part of the light beam entering the prism a second time.

The mirror prism can have a mirror surface on at least a section of a reflection surface. The surface area of a reflection surface can for example be at least partially coated with gold and/or silver.

The terms reflection surface and mirror surface generally correspond to each other. A mirroring or a reflection can occur on an at least partially mirrored surface or in particular also under certain angles on a transition between media of different refractive indexes, for example when a light beam that passes through an optically dense medium is incident on a boundary surface to a medium of low optical density. A total reflection can occur under special angles, wherein the entire share of the light beam is reflected in full.

A mirror prism that uses two reflection surfaces can in particular be a prism on which the two reflection surfaces describe a right angle and wherein the entrance and exit surface of the prism is positioned opposite said angle.

A beam splitter of a beam splitter unit in particular corresponds to a beam splitter cube or two individual plane parallel plates, that preferably respectively comprise $CaF_2$ and a beam splitter layer or a polarizing beam splitter cube or a plate beam splitter with two plates and a beam splitter layer. A beam splitter is in particular designed to transmit at least a part of the incident light beam on an exit surface in order to generate the first partial beam and to reflect at least a further portion of the incident light beam in order to generate the second partial beam. A beam splitter is furthermore in particular designed to reflect at least a part of the first partial beam on the incidence surface and to transmit at least a part of the second partial beam.

A beam splitter unit has at least one planar beam splitter layer in particular in a beam splitter cube or in a system comprised of plane parallel plates. The beam splitter layer has a first side facing the incident light beam that represents a beam splitter surface and a side facing away from the incident light beam that represents an overlay surface. The beam splitter surface is designed to transmit incident light in parts in order to generate and partially reflect a first partial beam in order to generate a second partial beam. Two partial beams that project essentially vertically in relation to each other are then in particular generated.

A mirror prism on which only one reflection surface is to be used can for example be a 90° deflection prism. Deviations from the 90° angle are possible in +/−30° ranges. 1° is the 360th part of a full circle.

An optical conjugation between the first field of view discriminator unit (BFD1; 631; 645; 653; 656; 666) and the second field of view discriminator unit (BFD2; 632; 646; 654; 657; 667) is in particular created when these optically coincide—as seen from the entrance of the double beam interferometer in direction of the double beam interferometer—and can therefore no longer be optically differentiated.

A narrow IR light source can be a dark red glowing, elongated silicon-carbide rod, that is for example 20 mm in length and has a diameter of 1 mm.

A focused image is in particular characterized in that it is nearly diffraction-limited.

An unfocused image is in particular characterized in that its image spots formed by an object point exceed the size of an Airy disk several times.

A coma in particular comprises asymmetry errors, in particular those created by an overlay of two imaging errors, given beams incident at a tilt to the optical axis. In particular an image point with a "tail" directed toward the edge of the optics can be created in place of a focused diffraction disk. A coma can in particular occur both on lens optics and also on mirror optics.

An astigmatism in particular comprises the phenomenon that in two intersection planes arranged vertically in relation to each other, two image points that are respectively formed by the beams of the respective intersection plane are significantly separated in their position along the depth axis, that is to say significantly separated in the propagation direction of the light. In relation to the invention, during detection, one of the image points is essentially preferably located in infinity, and the other image point preferably lies in the near range, preferably on the raster detector.

The term "depth axis" refers to the dimension in the propagation direction of the light.

The term "wave-optical depth of field focal range" is defined by the relation of the light wavelength divided by the square of the sine of the aperture angle of the associated light beam.

A mirrored surface is in particular designed to reflect at least approximately 80%, in particular at least approximately 93%, and preferably at least approximately 97% to approximately 99.9% of the incident light in at least a part of the wavelength spectrum of electromagnetic radiation.

An unreflective or non-reflective surface is in particular designed to reflect less than approximately 60%, in particular less than approximately 30%, and preferably less than approximately 10% of the incident light in at least a part of the wavelength spectrum of electromagnetic radiation.

The term "acute half angle" comprises the following values: having a value greater than 15 degrees and having a value less than 35 degrees.

An optical interference can be created during measurements of biological tissue by stray light that is distributed to several detector elements on a raster detector. This stray light is largely blocked by a confocal discrimination that reduces the optical interference. An optical interference can also be understood to mean that rays from an imperfect and/or slightly unfocused light beam that generate an image point for example on a detector element of a raster detector also reach one or several adjacent detector elements of the raster detector.

Cylindrical waves are in particular light waves that at least approximately and partially have the shape of a cylindrical surface, or a section thereof.

A double mirror periscope reflector can either be formed as a rooftop reflector in metal and/or also as a rooftop prism, as a pentaprism and/or as an angle reflector in air and/or vacuum with a preferred beam deflection between 60 degrees and 120 degrees. Both plane mirrors of the double mirror periscope reflector are in the double beam interferometer arranged vertically to the reference plane RE, in relation to which the beam splitter surface is also arranged vertically.

Respectively two double mirror periscope reflectors are arranged in a Mach-Zehnder Interferometer.

Respectively two double mirror periscope reflectors are likewise preferably arranged in a Michelson-Type Interferometer. However, two triple mirror periscope reflectors can also be arranged therein, which then represent the beam deflection unit.

Generally only a single double mirror periscope reflector is arranged in a cyclical double beam interferometer. However, the double mirror periscope reflector in the cyclical double beam interferometer can preferably be mapped to a comparatively small double mirrored staircase (85, 85*w*), or two individual mirrored staircases (82, 82*w*, 83, 83*w*) can preferably be mapped to this double mirror periscope reflector.

The following describes special embodiments and examples that can be combined with each other and in particular with the aspects of the invention, provided they do not exclude each other:

Fourier transformation spectrometer with at least partial hyperspectral single shot imaging of a measured object as a product of a calculation using a computer system with a computing program to obtain spectrums by means of Fourier transformation and having an upstream lens as imaging system for the measured object and with a double beam interferometer positioned downstream of the upstream lens, the lens comprising:

firstly either a beam splitter with a planar beam splitter surface and wherein the beam splitter is used for both beam splitting in the beam splitter plane, thus forming two partial beams TB1, TB2, and also for at least partial beam unification in the beam splitter plane using a lateral shear s between the two partial beams.

or secondly, two beam splitters, each with a planar beam splitter surface, wherein the first beam splitter is used for beam splitting in the beam splitter plane, thus forming two partial beams TB1, TB2, and a second beam splitter for at least partial beam unification using a lateral shear s between the two partial beams and a reference plane exists on the double beam interferometer, wherein the reference plane is spanned by the normal of the planar beam splitter surface and by the optical axis of the upstream lens on the input of the double beam interferometer, and a raster detector at the output of the double beam interferometer and the upstream lens arranged upstream of the cyclical double beam interferometer—taking into account the position of the measured object—generates an image or at least a partial image of the measured object in the light direction, generally downstream of the beam splitter, but generally upstream of the raster detector and with the involvement of an anamorphic imaging stage arranged downstream of the double beam interferometer generates a plurality, but at least two, spatial interferograms, wherein these spatial interferograms are rendered on the two-dimensional receiver raster receiver, and wherein an object point on the measured object is mapped to every spatial interferogram, wherein the double beam interferometer 601 is either formed with two interferometer arms IA1, IA2 as a non-cyclical interferometer 602, 603, 604 and respectively one double mirror periscope reflector or a prism 640, 641, 642, 651, 652, 661, 662 are arranged in each interferometer arm IA1, IA2, or respectively one triple mirror reflector or respectively one triple mirror prism is respectively arranged in each interferometer arm at least approximately in room corner shape and the difference of the mirrors or mirror surfaces in the two interferometer arms is zero and a field of view discriminator BFD1, BFD2 is arranged in each interferometer arm in a position between one third and two thirds of the optical distance OPD in the beam path between beam splitting and beam reunification, and these two fields of view discriminators BFD1, BFD2 are generally at least approximately optically conjugated in relation to each other or the double beam interferometer 601 can be configured as a cyclical double beam interferometer 605, 606, 608, 615, either with two plane mirrors 628, 629, 671, 672 that form a periscope arrangement 630 on which the two plane mirrors 628, 629, 671, 672 are spaced at unequal distances from the beam splitter plane ET that contains the horizontal beam splitting surface, and wherein the two plane mirrors are at least approximately aligned vertically in relation to the reference plane RE or the double beam Interferometer 601 is formed as a cyclical double beam interferometer 607, 609, 610, 611, 612, 613, 614 having two plane mirror surfaces 681, 682, 762, 674, 687s, 688s, 689s, 888, 890, 696s, of which respectively exactly one is formed of a refractive material on respectively one mirror prism 679, 680, 687, 688, 689, 696, 761, 763, 887, 889 thus creating a double mirror prism arrangement 697 that is formed with respectively exactly two mirror prisms 679, 680, 687, 688, 689, 689, 696, 761, 763, 887.

and either the two plane mirrors 628, 629, 671, 672, which are formed as a periscope arrangement 630, or the two-plane mirror surfaces 681, 682, 762, 674, 687s, 688s, 689s, 888, 890, 689s, 696s of the double mirror prism arrangement 697 are positioned at a predetermined unequal distance from the beam splitter plane ET that contains the beam splitter surface, and are at least approximately aligned vertically in relation to the reference plane RE and an angle epsilon with twice the value of the half angle psi is formed between the two plane mirrors 628, 629, 671, 672 or the plane mirror surfaces 681, 682, 687s, 688s, 696s, 689s, 696s, 762, 764, 888, 890 and this angle epsilon is formed by two straight lines g1, g2 projecting from the plane mirrors 628, 629, 671, 672 or from the plane mirror surfaces 681, 682, 687s, 688s, 689s, 696s, 762, 764 and 888, 890 in the reference plane RE and the half angle psi is formed with a value greater than 20 degrees and with a value less than 30 degrees and a first image plane BEI1 and a second image plane BEI2 are formed in the double beam interferometer 601, 602, 603, 604, 605, 605, 607, 608, 609, 610, 611, 612, 613, 614, 615 that are respectively determined by the upstream lens 70, 71, 73, 74, 75, the position of the measured object 1, 10, 14, 15, 16, and by the double beam interferometer 601, 602, 603, 604, 605, 605, 607, 608, 609, 610, 611, 612, 613, 614, 615, and the first image plane BEI1 is mapped to a first field of view discriminator BFD1, and the second image plane BEI2 is mapped to a second field of view discriminator BFD2 in the double beam interferometer 601, 602, 603, 604, 605, 605, 607, 608, 609, 610, 611, 612, 613, 614, 615 and these field of view discriminators BFD1, BFD2 are formed respectively with at least one nondiscriminating region in transmission or reflection and said two field of view discriminators BFD1, BFD2 are arranged in the double beam interferometer such that an optical conjugation exists at least approximately between these field of view discriminators.

Fourier transformation spectrometer,
wherein in a double beam interferometer 601, 602, 603, 604, 605, 605, 607, 608, 609, 610, 611, 612, 613, 614, 615 each field of view discriminator BFD1, BFD2 is mapped to a double mirror periscope reflector or a prism 630, 640, 641, 642, 651, 652, 661, 662 or to a triple mirror reflector in corner cube form.

Fourier transformation spectrometer,
wherein at least one image plane BEI1, BEI2 is at least partially brought to coincide at least approximately with respectively one field of view discriminator BFD1, BFD2 when the measured object 1, 10, 14, 15, 16 is imaged in a double beam interferometer 601, 602, 603, 604, 605, 605, 607, 608, 609, 610, 611, 612, 613, 614, 615.

Fourier transformation spectrometer,
wherein the two field of view discriminators BFD1, BFD2 are formed as a gap in a double beam interferometer 601, 602, 603, 604, 605, 605, 607, 608, 609, 610, 611, 612, 613, 614, 615.

Fourier transformation spectrometer,
wherein at least one field of view discriminator BFD in a double-beam interferometer 601, 602, 606 is formed as a computer controllable, spatial light modulator 649, 656.

Fourier transformation spectrometer,
wherein the two field of view discriminators BFD1, BFD2 in a Michelson-Type Interferometer 602, 603 are formed and arranged as a gap aperture 645, 646, 653, 654, and respectively exactly one gap aperture 645, 646, 653, 654 is positioned in each arm IA1, IA2 of the Michelson-Type Interferometer 602, 603.

Fourier transformation spectrometer, wherein
the first field of view discriminator unit 653 has an opening designed to spatially select the first partial beam TB1 after the splitting of the incident light beam EB using the beam splitter unit 622 and after the second reflection of the first partial beam TB1 using the second reflection surface 651b of the first prism 651; and/or
the second field of view discriminator unit 654 has an opening designed to spatially select the second partial beam TB2 after the splitting of the incident light beam EB using the beam splitter unit 622 and after the second reflection of the second partial beam TB2 using the first reflection surface 652b of the second prism 652.

Fourier transformation spectrometer, wherein
the first field of view discriminator unit 653 has an opening designed to spatially select the first partial beam TB1 after the splitting of the incident light beam EB using the beam splitter unit 622 and prior to the second reflection of the first partial beam TB1 using the second reflection surface 651b of the first prism 651; and/or
the second field of view discriminator unit 654 has an opening designed to spatially select the second partial beam TB2 after the splitting of the incident light beam EB using the beam splitter unit 622 and prior to the second reflection of the second partial beam TB2 using the first reflection surface 652b of the second prism 652.

Fourier transformation spectrometer,
wherein in a Michelson-Type Interferometer 602, every gap aperture 645, 646 is arranged in optical conjugation to the apparent end mirror surface SEF1, SEF2 of the respective interferometer arm IA1, IA2.

Fourier transformation spectrometer, wherein in a Michelson-Type Interferometer 602, 603, the field of view discriminators BFD1, BFD2 are each arranged in a position at least approximately at half the distance of the optical distance in the beam path between the beam splitting and beam reunification.

Fourier transformation spectrometer, wherein every double mirror periscope reflector or a prism 640, 641, 642, 651, 652 in a Michelson-Type Interferometer 602, 603 is formed with a beam deflection of at least approximately 180 degrees.

Fourier transformation spectrometer, wherein at least one field of view discriminator BFD1, BFD2 in a Michelson-Type Interferometer 602, 603 is formed with a liquid crystal display 649-1, 649-2.

Fourier transformation spectrometer, wherein the field of view discriminators BFD1, BFD2 are arranged in a Mach-Zehnder Interferometer 604, and in this case, respectively exactly one gap aperture 666, 667 is positioned in each arm IA1, IA2 of the Mach-Zehnder Interferometer 604 as a field of view discriminator.

Fourier transformation spectrometer, wherein in a double beam interferometer 601, 602, 603, 604, 605, 605, 607, 608, 609, 610, 611, 612, 613, 614, 615, the field of view discriminators BFD1, BFD2 are each arranged in a position at least approximately at half the distance of the optical distance in the beam path between the beam splitting and beam reunification.

Fourier transformation spectrometer, wherein the double mirror periscope reflectors 661, 662 in a Mach-Zehnder Interferometer 604 are formed with a beam deflection between 45 degrees and 135 degrees.

Fourier transformation spectrometer, wherein at least one field of view discriminator BFD1, BFD2 in a Mach-Zehnder Interferometer is formed as a digital micro-mirror array.

Fourier transformation spectrometer, wherein in a cyclical double beam interferometer 605, 605, 607, 608, 609, 610, 611, 612, 613, 614, 615 with two plane mirrors 628, 629, 671, 672 or two planar mirror surfaces 681, 682, 687s, 688s, 689s, 696s, 762, 764, 888, 890 respectively one gap opening 677, 678, 976, 977 is arranged in the two opposingly revolving partial beams TB1, TB2 of the cyclical double beam interferometer in respectively one gap aperture 631, 632, 976, 977 as field of view discriminator BFD1, BFD2 in an image plane of the measured object 1, 10, 14, 15, 16.

Fourier transformation spectrometer, wherein in a cyclical double beam interferometer 607, 613, 614 with two plane mirrors 628, 629, 671, 672 or two plane mirror surfaces 681, 682, 687s, 688s, 689s, 696s, 762, 764, 888, 890, a double gap aperture 676, 694, 975 with respectively two gap openings 677, 678, 977, 977 is arranged in the two opposingly revolving partial beams TB1, TB2 in a plane vertical to the main beams of the partial beams TB1, TB2 that represents the common image plane BEI12.

Fourier transformation spectrometer, wherein in a cyclical double beam interferometer 606 with two plane mirrors 671, 672, a computer-controlled, transmissive liquid crystal display 655 is preferably arranged between said plane mirrors 628, 629, 671, 672 or planar mirror surfaces with at least two pass-through areas 656, 657.

Fourier transformation spectrometer, wherein two gap-shaped pass-through areas 656 and 657 are embedded in the transmissive liquid crystal display 655.

Fourier transformation spectrometer, wherein in a cyclical double beam interferometer 605, 605, 607, 608, 609, 610, 611, 612, 613, 614, the beam splitter plane ET and the intersection SP of the straight lines g1 and g2 are separated from each other by the distance d_ST, and this distance d_ST is at least ten wavelengths of the largest wavelength in the spectrum of the detected light.

Fourier transformation spectrometer, wherein in a cyclical double beam interferometer 615, at least one mirrored staircase with two mirrors each is arranged in the region Z, where no spatial overlap occurs between the two partial beams TB1 and TB2.

Fourier transformation spectrometer, wherein in a cyclical double beam interferometer 615, two mirrored staircases 82, 83 with two mirrors each are arranged in the region Z, where no spatial overlap occurs between the two partial beams TB1 and TB2.

Fourier transformation spectrometer, wherein in a cyclical double beam interferometer 615, the two mirrors of a first mirrored staircase 82 are formed as plane mirrors 821, 822, and the two mirrors of the second mirrored staircase 83 are formed as plane mirrors 831, 832.

Fourier transformation spectrometer, wherein in a cyclical double beam interferometer 615, in region Z where no spatial overlap occurs between the two partial beams TB1 and TB2, the two plane mirrors 821, 822 are respectively arranged in parallel to each other on the first miniaturized mirrored staircase 82, and the two plane mirrors 831, 832 are respectively arranged in parallel to each other on the second miniaturized mirrored staircase 83.

Fourier transformation spectrometer, wherein the two parallel plane mirrors 821, 822 of a first mirrored staircase 82 and the parallel plane mirrors 831, 832 of a second mirrored staircase 83 in a cyclical double beam interferometer 615 preferably have a slightly different distance dm_1 and dm_2.

Fourier transformation spectrometer, wherein in a cyclical double beam interferometer 615, in region Z where no spatial overlap occurs between the two partial beams TB1 and TB2, the first mirrored staircase 82 and the second mirrored staircase 83 are combined into a double mirrored staircase 85 using a center web 84, and the two inner plane mirrors 822, 832 are respectively arranged in parallel to each other on a side of the center web 84 of the double mirrored staircase 85.

Fourier transformation spectrometer, wherein in a cyclical double beam interferometer 615, a field of view discriminator BFD is mapped to at least one mirrored staircase 82, 83.

Fourier transformation spectrometer, wherein the field of view discriminator BFD is either formed as a gap aperture 631, 632, as a narrow pinhole array, or as a raster, computer-controllable, micro-mechanical pinhole array.

Fourier transformation spectrometer, wherein a field of view discriminator BFD is formed as a narrow plane mirror 821s, 831s that forms one of the two plane mirrors of a mirrored staircase 82, 83.

Fourier transformation spectrometer, wherein a field of view discriminator BFD is formed as a computer-controllable digital micro-mirror array DMD in at least one mirrored staircase 82, 83.

Fourier transformation spectrometer, wherein in a cyclical double beam interferometer 615, a comparatively small angle tau_1 from up to 10 degrees between the two plane mirrors 821, 822 of a first mirrored staircase 82w, and also a comparatively small angle tau_2 from up to 10 degrees exists between the two plane mirrors 831, 832 of a second mirrored staircase 82w, and the values of the angles tau_1, tau_2 in both mirrored staircases 82w, 83w are made at least approximately the same, and the angle kappa between the main beam HTB1a that projects from the first mirrored staircase 82 and the main beam HTB2a that projects from the second mirrored staircase 83 is formed as less than 180 degrees, but not less than 140 degrees, on the side facing the interferometer 615.

Fourier transformation spectrometer, wherein in a cyclical double beam interferometer 615, at least one miniaturized mirrored staircase is arranged in the region Z, on which at least one mirror is formed with a weak curvature.

Fourier transformation spectrometer, wherein two mirror prisms 679, 680, 687, 688, 761, 763, 887, 889, 696, 689 of equal construction and each made of the same refractive material are arranged in the revolving beam path in a cyclical double beam interferometer 607, 609, 610, 612, 613, 614 for Fourier transformation spectroscopy and the mirror prisms 679, 680, 687, 688, 761, 763, 887, 889 are each formed with a single mirror surface, and said mirror prisms 679, 680, 687, 688, 761, 763, 887, 889 each have the same acute angle psi between the mirror surface and respectively one nonreflective surface and two field of view discriminators BFD1, BFD2 are positioned between these two mirror prisms of equal construction.

Fourier transformation spectrometer, wherein two mirror prisms 687, 696, 689 with the same angle and each made of the same refractive material are arranged in the revolving beam path in a cyclical double beam interferometer 611, 614 for Fourier transformation spectroscopy and the mirror prisms 687, 696, 689 are each formed with a single mirror surface 687s, 689s, 696s and said mirror prisms 687, 689, 696, 689 each have the same acute angle psi between the mirror surface 687s, 689s, 696s, and respectively one nonreflective surface and two field of view discriminators BFD1, BFD2 are positioned between these two mirror prisms 687, 696, 689 of equal angles.

Fourier transformation spectrometer, wherein two mirror prisms 696, 689 made of the same refractive material are arranged in a cyclical double beam interferometer 614, the mirror prisms each having only a single mirror surface 696s, 689s and the two mirror prisms 696, 689 each have a first acute angle psi, a second acute angle 2 psi, and a third angle with the value 180 degrees minus 3 psi, and thus at least three angles on the two mirror prisms 696, 689 then respectively match and furthermore, a plane parallel plate 698 made of refractive material is arranged between these two mirror prisms 696, 689, and the plane parallel plate 698 is fixed between these two mirror prisms 696, 689 by two optically transparent cement layers 695, 699, and either a beam splitter layer 62 is applied on the side of the plane parallel plate 698 facing the mirror prism 689, or alternatively, the beam splitter layer 62 is applied on the mirror prism 689 on the side of the plane parallel plate 698 facing the plane parallel plate 698.

Fourier transformation spectrometer with at least partial hyperspectral single shot imaging of a measured object as a product of a calculation using a computer system for obtaining spectrums by means of Fourier transformation and having an upstream lens as imaging system for the measured object and with a cyclical double beam interferometer positioned downstream of the upstream lens, the lens comprising:

a beam splitter with a planar beam splitter surface and wherein the beam splitter is used for both beam splitting in the beam splitter plane, thus forming two partial beams TB1, TB2, and also for at least partial beam unification in the beam splitter plane using a lateral shear s between the two partial beams.

and a reference plane exists on the cyclical double beam interferometer, wherein the reference plane is spanned by the normal of the planar beam splitter surface and by the optical axis of the upstream lens on the input of the interferometer, and a raster detector at the output of the cyclical double beam interferometer and the upstream lens arranged upstream of the cyclical double beam interferometer—taking into account the position of the measured object—generates an image or at least a partial image of the measured object in the direction of the light, generally downstream of the beam splitter, but generally upstream of the raster detector and with the involvement of an anamorphic imaging stage arranged downstream of the cyclical double beam interferometer generates a plurality, but at least two, spatial interferograms, wherein these spatial interferograms are rendered on the two-dimensional receiver raster receiver, and wherein an object point on the measured object is mapped to every spatial interferogram, wherein the cyclical double beam interferometer 616 is formed with two plane mirrors 628, 629 that form a periscope arrangement 630, wherein the two plane mirrors 628, 629 are equidistant from the beam splitter plane ET that contains the planar beam splitter surface and are at least approximately arranged vertically in relation to the reference plane RE and an angle epsilon with double the value of the half angle psi exists between the two plane mirrors that form the periscope arrangement 630 and said angle epsilon is represented by two straight lines g1, g2 projecting from the plane mirrors or from the planar mirror surfaces in the reference plane RE, and the half angle line of the angle epsilon in half lies in the beam splitter plane ET and the half angle psi is formed with a value greater than 20 degrees and with a value less than 30 degrees and the symmetrically constructed cyclical double beam interferometer 616 has a first image plane BEI1 and a second image plane BEI2 that are each determined by the upstream lens, the location of the measured object, and the double beam interferometer 616, and the first image plane BEI1 is mapped to a first field of view discriminator BFD1, and the second image plane BEI2 is mapped to a second field of view discriminator BFD2 in the double beam interferometer 616 and said two field of view discriminators BFD1, BFD2 are arranged in the symmetrically constructed cyclical double beam interferometer 616 such that an optical conjugation exists at least approximately between these field of view discriminators BFD1, BFD2, and in the cyclical double-beam interferometer 616, one optical functional assembly each to generate a beam shear is mapped to one field of view discriminator BFD each between the plane mirrors 628, 629 in the revolving beam path, which form a periscope arrangement 630, and the optical functional assemblies generate a beam shear in a respectively opposing direction, thus generating a lateral shear s at the output of the cyclical double beam interferometer.

Fourier transformation spectrometer, wherein the optical functional assemblies are formed as two mirrored staircases 82, 83 in air or as two at least rhomboid-like mirror prisms to generate a beam shear in a cyclical double beam interferometer.

Fourier transformation spectrometer, wherein the field of view discriminators BFD1, BFD2 are formed as gap apertures 831, 832.

The term "Double Beam Interferometer" herein describes three double beam interferometer types (Michelson-Type Interferometer, Mach-Zehnder Interferometer, cyclical double beam interferometer). The logical parentheses consist of the fact that the field of view discrimination on all three double beam interferometer types generally occurs by means of two field of view discriminators, and generally directly in the double beam interferometer on the two coherent images of the measured object generated in the double beam interferometer. In this case, generally only respectively a rather narrow partial image for detection remains of one image respectively after the field of view discrimination (e.g. by two gap apertures, (645-646, 652-653, 666-667). However, a spatial interferogram (rI) can be obtained in single shot mode from these two coherent partial images from all measurement spots of the latter, so that a plurality of spatial interferograms (rI) can be detected at the same time. A hyperspectral partial image can then be generated. The hyperspectral composite image can be generated from partial images obtained in a timeseries.

A logical parentheses furthermore consist of the fact that a pair of shifted periscopes (double mirror periscope reflectors) are respectively arranged as air-type (641-642) or (661-662) or as prism type (651-652) in a Michelson-Type Interferometer (FIG. 4 and FIG. 11) and also in a Mach-Zehnder Interferometer (FIG. 12). Accordingly, respectively exactly one periscope is arranged in an interferometer arm (IA1, IA2) of the just specified interferometers.

According to the invention, respectively one field of view discriminator (typically a gap aperture 645, 646) is maps to a double angle periscope reflector (640) (arranged upstream, downstream, or between the two mirrors of a double mirror periscope reflector 640). The lateral shear s is caused by the lateral shift of a double mirror periscope reflector 640 in the double beam interferometer. According to the invention, the discrimination occurs in or on the double mirror periscope reflector 640.

A triple mirror can be used alternatively to each double mirror periscope reflector or to each double mirror prism.

In particular only exactly one double mirror periscope reflector (630) or one double mirror prism arrangement (683) exists in the revolving beam path of a cyclical double beam interferometer (FIG. 13 up to FIG. 37), either as an air-type (or as 630) or as a mirror prism-type (or as 683). A double mirror prism arrangement (683) in particular and essentially has the same function as a double mirror periscope reflector. According to the invention, respectively exactly one field of view discriminator (631, 632) or (656, 567) or (677, 678) is mapped to this double mirror periscope reflector (630) or to the double mirror prism arrangement (683) in the two opposingly revolving partial beam paths. To a field of view discriminators then there also exists in this case; however, these are in particular only mapped to the double mirror periscope reflector (630) or to the double mirror prism arrangement (683), in that these two fields of view discriminators are generally positioned within the double mirror periscope reflector (630) or the double mirror prism arrangement (683).

In particular two options apply for a cyclical double beam interferometer:

1. The lateral shear can be created by an asymmetry in the cyclical double beam interferometer with a shift of the double mirror periscope reflector (630) or the double mirror prism arrangement (683) in relation to the beam splitter plane ET. This shift is described by d_ST, the distance of the intersection SP from the beam splitter plane ET. This distance d_ST is firstly unequal to zero. The intersection SP lies in the symmetry plane E_S of a double mirror periscope reflector (630) or a double mirror prism arrangement (683).

2. The lateral shear s results in the second case d_ST equal to zero, which causes a symmetry in a cyclical double beam interferometer, due to the mapping of two mirrored staircases as air-type (FIGS. 31 to 36) or as prism-type (no figure) between the plane mirrors (628, 629) of the double mirror periscope reflector (630) or the mirror prisms of double mirror prism arrangement (683). In this case, the symmetry—that is to say the case d_ST equal to zero—must not necessarily exist in a cyclical double beam interferometer in order to map two mirrored staircases. The resulting lateral shear s is then only based on the presence of the mirrored staircases and their arrangement.

3. But two mirrored staircases can also be mapped in the case of d_ST unequal to zero. The resulting lateral shear s is then based on both, the asymmetry (d_ST unequal to zero) and the presence of two mirrored staircases. The case of the arrangement with only one mirrored staircase is not a preferred version, because this case generally creates a relatively large optical distance difference between the interfering partial beams.

The FT spectrometer according to the invention is advantageously used in particular when a field of view discrimination is necessary on laterally expanded measurement objects and the measurement spots in the hyperspectral image are predetermined rather coarsely to achieve a high signal-to-noise ratio, and the tilt invariance of the double mirror periscope reflectors or the cyclical interferometer thus do not permit any out-of-adjustment condition of the interferometer under standard conditions.

In summary, a double beam interferometer with a raster detector is used for a method and a double beam interferometer for single shot imaging for Fourier spectroscopy, in particular for measuring chaotically moving measured objects and turbulent scenes, with at least partial hyperspectral imaging of the measured object and/or the scene in the spectrometer. The double beam interferometer can in this case be formed as a Michelson-Type Interferometer, as a Mach-Zehnder Interferometer, or as a cyclical double beam interferometer. Two partial beams TB1 and TB2 are formed with a lateral shear s at the output of the interferometer. For this purpose, the plane mirrors arranged in pairs in the interferometer are at least formed as a double mirror periscope reflector that is arranged laterally shifted in relation to the first light beam or the second light beam, or a mirrored staircase is additionally mapped to this double mirror periscope reflector. A pair of coherent partial images of the measured object are created in the interferometer by means of an upstream lens and the interferometer. Therein, these partial images are subject to a field of view discrimination using two gap apertures. After these discriminated images and/or partial images are rendered with a lateral shear s through an anamorphic lens, the image elements of the partial images of the measured object are used to form spatial interferograms on the detector, from which spectrums are calculated for a hyperspectral image.

| Reference symbol list with explanations | |
|---|---|
| Reference symbols | Identifier |
| 1 | Back of an older patient subject to diagnosis as a measured object |
| 10 | Biological measured object |
| 11 | Skin feature that from a medical point of view must be carefully examined as it can either be a birthmark and/or a melanoma. |
| 12 | High-risk region, highlighted in color on the monitor Following analysis of the spectral data, the risk level can be determined by artificial intelligence. |
| 13 | Image of the region on the back 1 recorded by means of a spectrometer scan |
| 14 | Measured object for incident light measurement |
| 15 | Moving, partially transparent measured object for a transmitted light measurement |
| 16 | Biological measured object with fluorescent markers |
| 20 | Fourier transformation spectrometer system |
| 21 | Computer system for controlling the components, such as the light source and raster detector, and with a computer program for analyzing the spatial interferograms rl and for calculating spectrums |
| 22 | Analysis program for the calculated spectrums SP, also in order to localize high-risk regions for skin cancer with colored highlighting for the identified risk on a monitor 23 |
| 23 | Monitor for rendering the analyzed data |
| 25 | Control and synchronization mean |
| 28 | Datalink to databases |
| 30 | Mobile measurement head |
| 31 | Handle of the mobile measurement head 30 |
| 32 | Start button for recording data |
| 40 | Pulsed striped light source in the NIR range |
| 41 | Light source driver, controllable by the computer 21 |
| 42 | Datalink |
| 43 | Pulsed striped light source, controllable by the computer 21, whose light is coaxially coupled into the illumination beam path by a coupling beam splitter cube 57 |
| 44 | pulsed NIR light source, controllable by the computer 21, with integrated beamforming optics 45 for projecting a light stripe 80 onto a biological measured object 10 in a coaxial arrangement |
| 45 | Beamforming optics in mirror form 45 for projecting a light stripe 80 onto a biological measured object 10 |
| 46 | Pentaprism |
| 47 | Narrow IR light source for short-duration stripe-shaped illumination of a partially transparent moving measured object 15 |
| 48 | Lens for rendering an IR light source onto a partially transparent measured object 15 |
| 49 | Narrow raster UV light source, controllable by the computer 21, that is chronologically synchronized with the liquid crystal display 655, and formed with a control mechanism for luminescent pixels that are optically conjugated into a transmissive liquid crystal display 655. |
| 491 | Collimator lens for a UV light source 49 |
| 50 | Optics unit of the mobile measurement head 30 with a double beam interferometer 601 with a lens 51 arranged downstream thereof at the output thereof and a raster detector 54 used for detecting spatial interferograms rl. |
| 51 | Anamorphic and largely achromatic lens arranged downstream of the double beam interferometer at the output thereof in order to use coherent image points of a measured object 1 to generate interfering cylindrical waves tilted toward each other on a raster detector 54. |
| 511 | Rotationally symmetric component of the anamorphic lens 51 |
| 512 | Cylindrical component of the anamorphic lens 51 |
| 52 | Anamorphic lens also formed with the cylindrical component 522 for the MIR-CaF2 spectral range, which principally corresponds to the optical overall function of the lens 51, and corrected for a chromatic opening error in the interferometer. |
| 521 | Rotationally symmetric component of the anamorphic lens 52 |
| 522 | Cylindrical component of the anamorphic lens 52 |
| 53 | Anamorphic mirror-lens also formed with the cylindrical component |
| 532 | for the MIR spectral range, which principally corresponds to the optical overall function of the lens 51, and formed without opening error correction. |
| 531 | Rotationally symmetric component of the anamorphic lens 53 |
| 532 | Cylindrical component of the anamorphic lens 53 |
| 54 | InGaAs camera for the near infrared spectral range that is formed controllable by the computer 21 |
| 55 | CMOS camera for the visible spectral range that is formed controllable by the computer 21 |
| 56 | Control link and datalink |
| 57 | Coupling beam splitter cube for light to illuminate a measured object |

-continued

| Reference symbols | Identifier |
|---|---|
| 571 | Dichroic coupling beam splitter cube with a reflective splitter layer for UV light and with transmission properties of the spider layer for florescent light in the VIS spectral range |
| 572 | One-dimensional galvano mirror scanner, controllable by the computer 21 |
| 573 | Microscope lens |
| 574 | Deflection mirror |
| 575 | Telecentric aperture |
| 576 | UV blocking filter |
| 58 | Anamorphic lens with chromatic opening error correction for the polarizing beam splitter cube 636 |
| 581 | Rotationally symmetric component of the anamorphic lens 58 |
| 582 | Cylindrical component of the anamorphic lens 58 |
| 59 | Anamorphic lens for the MIR range, also with mirror optics |
| 591 | Rotationally symmetric component of the anamorphic lens 59 |
| 592 | Cylindrical component of the anamorphic lens 59 |
| 595 | Anamorphic lens for the MIR range with three reflective free-form surfaces 875, 876, and 877 |
| 601 | Double beam interferometer that generates a lateral shear s |
| 602 | Michelson-Type Interferometer with lateral shear s, and that is in this case formed with a splitter cube and a rooftop reflector, in particular with metal |
| 603 | Michelson-Type Interferometer with lateral shear s, and that is in this case formed with a splitter cube and a 90° rooftop reflector |
| 604 | Mach-Zehnder Interferometer with a lateral shear s |
| 605 | Cyclical double beam interferometer with lateral shear s with two plane mirrors 628 and 629 and a foil beam splitter 623 |
| 606 | Cyclical double beam interferometer for the visible spectral range with two plane mirrors 671 and 672 and a polarizing beam splitter cube 636 |
| 607 | Cyclical double beam interferometer for the visible spectral range with two mirror prisms 679 and 680 and a polarizing beam splitter cube 622 |
| 608 629 | Cyclical double beam interferometer with two plane mirrors 628 and and a plate beam splitter |
| 609 | Cyclical double beam interferometer with two prisms 690 and 691 of equal construction and two mirror prisms 687 and 688 of equal construction, and with an air gap in the throat |
| 610 | Cyclical double beam interferometer with two prisms 690 and 691 of equal construction and two mirror prisms 687 and 688 of equal construction, and without airgap |
| 611 | Cyclical double beam interferometer with a triangle prism 690 and two mirror prisms 687 and 689, and without airgap |
| 612 | Cyclical double beam interferometer with two mirror prisms 761 and 763, in particular made of CaF2, that form the double mirror prism arrangement 683, and the tilted plane parallel plates 92 and 95, in particular made of CaF2 |
| 613 | Cyclical double beam interferometer for the infrared spectral range with a beam splitter 623, in particular with mylar foil and two mirror prisms |
| 687 | and 689, in particular with ZnSe |
| 614 | Cyclical double beam interferometer for the VIS and NIR spectral range as a cemented block with cemented-in plane parallel plate 698 |
| 615 | Cyclical double beam interferometer for the far-infrared spectral range, in particular with a mylar foil 86 for beam splitting and two plane mirrors 628 and 629 |
| 616 | Symmetrically constructed cyclical double beam interferometer $d\_ST = 0$ applies. |
| 62 | Beam splitter layer The latter also represents the planar beam splitter surface. |
| 620 | Beam splitter unit that comprises the plane parallel plates 624 and 627, and the beam splitter layers 625 and 626. |
| 622 | Beam splitter cube |
| 623 | Beam splitter, in particular with mylar foil |
| 624 | Plane parallel plate, in particular with CaF2, with a beam splitter layer 625 |
| 625 | Beam splitter layer for the wave number range 4000 $cm^{-1}$ to 1200 $cm^{-1}$ The latter also represents the planar beam splitter surface. |
| 626 | Beam splitter layer for beam unification for the wave number range 4000 $cm^{-1}$ to 1200 $cm^{-1}$ The latter also represents the planar beam splitter surface. |
| 627 | Plane parallel plate, in particular with CaF2, as a substrate for the beam splitter layer 626 |
| 628 | First plane mirror in a cyclical interferometer for the MIR and FIR spectral range, that is a constituent element of the double mirror periscope reflector 630 |

-continued

| Reference symbols | Identifier |
|---|---|
| 629 | Second plane mirror in a cyclical interferometer for the MIR and FIR spectral range, that is a constituent element of the double mirror periscope reflector 630 |
| 630 | Periscope arrangement, in particular a periscope reflector, preferably a double mirror periscope reflector (630) that is formed by the plane mirrors 628 and 629 for the infrared spectral range and/or by the plane mirrors 671 and 672 for the visible spectral range.<br>The beam deflection unit is in this case formed as a double mirror periscope reflector 630. |
| 631 | Gap aperture for the partial beam TB1 with a gap opening in the sense of a shading aperture, that represents a field of view discriminator in the image plane BEI1.<br>The width of a gap opening should not exceed the value d_ST, or the distance between the symmetry plane E_S and the beam splitter plane ET and beam unification. |
| 632 | Gap aperture for the partial beam TB2 with a gap opening in the sense of a shading aperture, that represents a field of view discriminator in the image plane BEI2. |
| 633 | Auxiliary shading aperture to avoid optical interference |
| 634 | Microbolometer array, controllable by the computer 21 |
| 636 | Polarizing beam splitter cube |
| 637 | Polarizing beam splitter layer<br>The latter also represents the planar beam splitter surface. |
| 638 | Polarization analyzer |
| 641 | Double mirror periscope reflector, in particular formed as a 90-degree rooftop reflector in particular with metal, that is to say a hollow body, manufactured by single point diamond machining for a 180-degree deflection in the first arm IA1 of the Michelson-Type Interferometer 602, shown in the FIGS. 4 to 8.<br>A beam deflection unit is in this case formed as a double mirror periscope reflector 641. |
| 641a | First minor, shown in the FIGS. 4 to 8. |
| 641b | Second minor, shown in the FIGS. 4 to 8. |
| 642 | Double mirror periscope reflector, in particular formed as a 90-degree rooftop reflector and in particular with metal, that is to say a hollow body, manufactured by single point diamond machining for a 180-degree deflection in the second arm IA2 of the Michelson-Type Interferometer 602, shown in the FIGS. 4 to 8.<br>A beam deflection unit is in this case formed as a double mirror periscope reflector 641. |
| 642a | First minor, shown in the FIGS. 4 to 8. |
| 642b | Second mirror, shown in the FIGS. 4 to 8. |
| 643 | Metal base body in the first arm IA1 of the Michelson-Type Interferometer 602, shown in the FIGS. 5 to 8 |
| 644 | Metal base body in the second arm IA2 of the Michelson-Type Interferometer 602, shown in the FIGS. 5 to 8 |
| 645 | Gap aperture with the width b in the FIGS. 5 and 6 in the first arm IA1 of a Michelson-Type Interferometer 602, which represents a field of view discriminator |
| 646 | Gap aperture with the width b in the FIGS. 5 and 6 in the second arm IA2 of a Michelson-Type Interferometer 602, which represents a field of view discriminator |
| 647-1 | Piezo actuator, shown in FIG.6, in the first interferometer on IA1 of a Michelson-Type Interferometer 602, controllable by the computer 21, that is mapped to the gap aperture 645 |
| 647-2 | Piezo actuator, shown in FIG. 6, in the second interferometer on IA2 of a Michelson-Type Interferometer 602, controllable by the computer 21, that is mapped to the gap aperture 646 |
| 648-1 | Elongated pinhole array with the width b, shown in FIG. 7, in the first interferometer arm IAL that represents a plurality of field of view discriminators |
| 648-2 | Elongated pinhole array with the width b, shown in FIG. 7, in the second interferometer arm IA2, that represents a plurality of field of view discriminators |
| 649-1 | First transmissive liquid crystal display (LCD), shown in FIG. 8, in the first interferometer arm IAL controllable by the computer 21 |
| 649-2 | Second transmissive liquid crystal display (LCD), shown in FIG. 8, in the second interferometer arm IA2, controllable by the computer 21 |
| 650-1 | Elongated light-permeable region of width b, shown in FIG. 8, embedded in the transmissive liquid crystal display in the first interferometer arm IA1 |
| 650-2 | Elongated light-permeable region of width b, shown in FIG. 8, embedded in the transmissive liquid crystal display in the second interferometer arm IA2 |

-continued

| Reference symbols | Identifier |
|---|---|
| 651 | Prism, preferably formed as a 90° rooftop prism, in particular for 180° deflection in the first interferometer arm IA1, with two reflection surfaces or mirror surfaces, shown in FIG. 11<br>The prism 651 represents a double mirror periscope reflector and is a beam deflection unit |
| 651a | First mirror surface on prism 651, shown in FIG. 11 |
| 651b | Second mirror surface on prism 651, shown in FIG. 11 |
| 652 | Prism, preferably formed as a 90° rooftop prism, in particular for a 180° beam deflection in the second interferometer arm IA2, with two reflection surfaces or mirror surfaces, shown in FIG. 11<br>The prism 652 represents a double mirror periscope reflector and is a beam deflection unit |
| 652a | First mirror surface on prism 652, shown in FIG. 11 |
| 652b | Second mirror surface on prism 652, shown in FIG. 11 |
| 653 | Long, gap-shaped gap aperture of width b, shown in FIG. 11, in the first interferometer arm IA1<br>The gap aperture 653 represents a field of view discriminator. |
| 654 | Long, gap-shaped gap aperture of width b, shown in FIG. 11, in the second interferometer arm IA2<br>The gap aperture 654 represents a field of view discriminator. |
| 655 | Transmissive liquid crystal display in a cyclical interferometer, controllable by the computer 21 |
| 656 | First pass-through area in a transmissive liquid crystal display 655 in a cyclical interferometer, represents the field of view discriminator BFD1 |
| 657 | Second pass-through area in a transmissive liquid crystal display 655 in a cyclical interferometer, represents the field of view discriminator BFD2 |
| 661 | Double mirror periscope reflector in the first interferometer arm IA1 of a Mach-Zehnder Interferometer 604<br>A beam deflection unit is in this case shown as a double mirror periscope reflector 661 |
| 661a | Plane mirror |
| 661b | Plane mirror |
| 662 | Double mirror periscope reflector in the second interferometer arm IA2 of a Mach-Zehnder Interferometer 604<br>A beam deflection unit is in this case shown as a double mirror periscope reflector 661 |
| 662a | Plane mirror |
| 662b | Plane mirror |
| 666 | Gap aperture in the Mach-Zehnder Interferometer 604, arranged at the smallest beam constriction and formed with a gap opening having at least double the width as on the fine gap aperture 667, represents a field of view discriminator |
| 667 | Fine gap aperture in the Mach-Zehnder Interferometer 604 in the image plane, represents a field of view discriminator |
| 668 | Plane plate group for adjusting and/or influencing the optical distance difference OPD_zykaP, shown in FIG. 18a, that is preferably formed for the MIR spectral range |
| 669 | Plane plate group for adjusting and/or influencing the optical distance difference OPD_zykaP, for complete compensation of the image shift in the depth axis, shown in FIG. 19a, that is preferably formed for the MIR range |
| 670a, 670b | Plane plate group for adjusting and/or influencing the optical distance difference OPD_zykaP, for complete compensation of the image shift in the depth axis, preferably formed for the VIS and NIR range, and shown in FIG. 28a and FIG. 29 |
| 671 | First plane mirror in a cyclical interferometer for the VIS spectral range that is a constituent element of the double mirror periscope reflector 630 |
| 672 | Second plane mirror in a cyclical interferometer for the VIS spectral range that is a constituent element of the double mirror periscope reflector 630 |
| 673 | CaF2 beam splitter plate |
| 674 | Beam splitter layer |
| 675 | CaF2 compensation plate |
| 676 | Double gap aperture in a cyclical double beam interferometer with the gap openings 677 and 678 |
| 677 | First gap opening, represents a field of view discriminator BFD1 |
| 678 | Second gap opening, represents a field of view discriminator BFD2 |
| 679 | Mirror prism in arm IA1 of a cyclical double beam interferometer 607 |
| 680 | Mirror prism in arm IA2 of a cyclical double beam interferometer 607 |
| 681 | Minor surface in arm IA1 of a cyclical double beam interferometer on a mirror prism |
| 682 | Minor surface in arm IA2 of a cyclical double beam interferometer on a mirror prism |

-continued

| Reference symbols | Identifier |
|---|---|
| 683 | Double minor prism arrangement for the midinfrared spectral range with the two minor prisms 761 and 763<br>The double mirror prism arrangement 683 represents a double minor periscope reflector. |
| 685 | Cylindrical wave fronts |
| 686 | Peak lines of cylindrical wave fronts tilted toward each other |
| 687 | Mirror prism in arm IA1 of a cyclical double beam interferometer, manufactured in one operation together with the mirror prism 688, and therefore of equal construction, and also made of the same material |
| 687F | Front face of the minor prism 687, here only polished for the purpose of creating an optical adjustment option |
| 687s | Minor surface of the mirror prism 687 |
| 687u | Nonreflective surface of the mirror prism 687, used for beam entry and also for beam exit |
| 688 | Mirror prism in arm IA2 of a cyclical double beam interferometer<br>The latter is also manufactured in one operation together with the mirror prism 687 and is therefore of equal construction and also made of the same material. |
| 688F | Front face of the minor prism 688, here only polished for the purpose of creating an optical adjustment option |
| 688s | Minor surface of the mirror prism 688 |
| 689 | Mirror prism |
| 689s | Minor surface of the mirror prism 689 |
| 689u | Nonreflective surface of the mirror prism 689, used for beam entry and also for beam exit |
| 690 | Acute and also isosceles triangle prism with an angle of 2psi in a cemented beam splitter, of equal construction as the triangle prism 691 |
| 691 | Acute and also isosceles triangle prism with an angle of 2psi in a cemented beam splitter, of equal construction as the triangle prism 690 |
| 692 | Cemented beam splitter with two triangle prisms 690 and 691 of equal construction |
| 693 | Cemented beam splitter, in particular with mirror prism 689 and triangle prism 690 that are not of equal construction |
| 694 | Printed double gap aperture in a cemented group in a cyclical double beam interferometer 610 with two gap openings |
| 695 | Thin transparent cement layer between the mirror prism 689 and the beam splitter layer 62, which is positioned on the plane parallel plate 698 |
| 696 | Mirror prism of equal construction as 689, arranged mirrored |
| 696s | Mirrored layer on the mirror prism, like 689 |
| 697 | Double mirror prism arrangement<br>This double mirror prism arrangement 697 is respectively formed with the two mirror prisms:<br>679 and 680 (VIS range)<br>or 687 and 688<br>or 687 and 689<br>or 689 and 696<br>or 887 and 889.<br>The double mirror prism arrangement 697 represents a double mirror periscope reflector.<br>The double mirror periscope reflector is a beam deflection unit. |
| 698 | Plane parallel plate with beam splitter layer 62 between the mirror prisms 689 and 696 |
| 699 | Thin transparent cement layer between the mirror prism 696 and the plane parallel plate 698 |
| 70 | Upstream lens<br>It is arranged upstream of the cyclical double beam interferometer 601 and represents an imaging system. |
| 71 | Upstream lens with upstream tele-centric aperture 72<br>It is arranged upstream of the cyclical double beam interferometer 602 and represents an imaging system. |
| 72 | Telecentric aperture |
| 73 | Upstream lens for the MIR spectral range without opening error correction<br>It is respectively arranged upstream of the cyclical double beam interferometer 604 and 605 and represents an imaging system. |
| 74 | Upstream lens for the VIS spectral range with correction of the sphero-chromatic aberration for refractive components that represent unfolded plane parallel plates<br>It is respectively arranged upstream of the cyclical double beam interferometer 606 and 607 and represents an imaging system. |

| Reference symbol list with explanations | |
|---|---|
| Reference symbols | Identifier |
| 75 | Upstream lens for the MIR spectral range, in particular with correction of the sphero-chromatic aberration for the CaF2 plates 673, 675, and 92<br>It is arranged upstream of the cyclical double beam interferometer 608 and represents an imaging system. |
| 751 | Upstream mirror lens for the MIR spectral range, formed with the free-form surface 872 on the mirror block 871 and the first free-form surface 874 on the mirror block 873<br>It is arranged upstream of the cyclical double beam interferometer 615 and represents an imaging system. |
| 761 | Mirror prism in particular made of calcium fluoride |
| 762 | Mirror surface on mirror prism 761 |
| 763 | Mirror prism in particular made of calcium fluoride |
| 764 | Mirror surface on mirror prism 763 |
| 765 | First plane parallel plate, in particular with ZnSe of the geometric thickness h1 for the MIR spectral range, with the refractive index n1 and with gap aperture |
| 766 | Second plane parallel plate, in particular with ZnSe of the geometric thickness h2 for the MIR spectral range, with the refractive index n1 and with gap aperture |
| 767 | First plane parallel plate, in particular with CaF2 of the geometric thickness h1 for the MIR spectral range, with the refractive index n1 and with gap aperture |
| 768 | Second plane parallel plate, in particular with ZnSe of the geometric thickness h2 for the MIR spectral range, with the refractive index n2 and with gap aperture |
| 781 | Thin transparent cement layer |
| 782 | Thin transparent cement layer |
| 80 | Light stripe that is projected and slightly over-sized in the height and length so that the measurement field 81 is generally fully illuminated. The measurement field 81 is determined by a reverse imaging of the field of view discriminators BFD onto the measured object. |
| 81 | Measurement field recorded at a time t1 |
| 82 | First mirrored staircase for the partial beam TB1 with two plane mirrors 821 and 822 in a parallel arrangement with the mirror distance dm_1 |
| 821 | |
| 82w | First mirrored staircase in a periscope arrangement for the partial beam TB1 with two plane mirrors 821 and 822 |
| 821 | First plane mirror of the first mirrored staircase 82 for the partial beam TB1, manufactured with single point diamond machining and gold-plated |
| 821s | First plane mirror of the first mirrored staircase 82 for the partial beam TB1<br>This plane mirror is formed narrow and is gold-plated, and in this case acts as a field of view discriminator. It is manufactured by means of single point diamond machining. |
| 822 | Second plane mirror of the first mirrored staircase 82 for the partial beam TB1<br>This plane mirror is manufactured by means of single point diamond machining and is gold-plated. |
| 822s | Second plane mirror of the first mirrored staircase 82 for the first partial beam TB1<br>This plane mirror is formed narrow and is gold-plated, and in this case acts as a field of view discriminator. It is manufactured by means of single point diamond machining. |
| 83 | Second mirrored staircase for the second partial beam TB2 with two plane mirrors 831 and 832 in a parallel arrangement with the mirror distance dm_2<br>and the following applies: dm_2 is less than dm_1. |
| 83w | Second mirrored staircase in a periscope arrangement for the partial beam TB2 with two plane mirrors 831 and 832 |
| 831 | First plane mirror of the first mirrored staircase 83 for the partial beam TB2, manufactured with single point diamond machining and gold-plated |
| 831s | First plane mirror of the first mirrored staircase 83 for the partial beam TB2<br>This plane mirror is formed narrow and is gold-plated, and in this case acts as a field of view discriminator. It is manufactured by means of single point diamond machining. |
| 832 | Second plane mirror of the second mirrored staircase 83 for the partial beam TB2, manufactured with single point diamond machining and gold-plated |

-continued

| Reference symbols | Identifier |
|---|---|
| 832s | Second plane mirror of the second mirrored staircase 83 for the partial beam TB2<br>This plane mirror is formed narrow and is gold-plated, and in this case acts as a field of view discriminator. It is manufactured by means of single point diamond machining. |
| 84 | Center web, in particular with metal, with the two plane mirrors 822 and 832, manufactured by means of single point diamond machining |
| 85 | Double mirrored staircase with four plane mirrors 821, 822, 831, 832 that are arranged in parallel in relation to each other,<br>formed as a metallic monolith and manufactured by means of single point diamond machining |
| 85w | Double mirrored staircase with four plane minors 821, 822, 831, 832 that are arranged in pairs tilted toward each other,<br>formed as a metallic monolith and manufactured by means of single point diamond machining |
| 86 | Mylar foil for beam splitting for the far infrared spectral range, for example for the wave number range around 200 $cm^{-1}$ |
| 861 | Upstream aperture for beam limiting that however does not represent a field of view aperture. |
| 870 | Arrangement with mirror optics and with a cyclical double beam interferometer 615 for measurement in the far FIR range |
| 871 | First minor block for focusing the arriving electromagnetic FIR radiation by means of the free-form surface 872 |
| 872 | First reflective free-form surface on the mirror block 871 |
| 873 | Second minor block |
| 874 | First reflective free-form surface on the mirror block 873, and in this case in total the second free-form surface |
| 875 | Second reflective free-form surface on the mirror block 873, and in this case in total the third reflective free-form surface |
| 876 | Second reflective free-form surface on the mirror block 871, formed as a saddle shape, and in this case in total the fourth reflective free-form surface |
| 877 | Third reflective free-form surface on the mirror block 873, and in this case in total the fifth reflective free-form surface<br>The latter is used to couple out the partial beam TB1 and TB2 for the purpose of detecting spatial interferograms rl.<br>The reflective free-form surfaces 875, 876, and 877 form a downstream anamorphic lens. |
| 887 | Mirror prism, in particular with ZnSe in the arm IA1 of a cyclical double beam interferometer |
| 888 | Minor surface on the minor prism 887 |
| 889 | Mirror prism, in particular with ZnSe in the arm IA2 of a cyclical double beam interferometer |
| 890 | Minor surface on the minor prism 889 |
| 891 | Nonreflective entrance surface on the minor prism 887 |
| 892 | Nonreflective exit surface on the mirror prism 887 |
| 893 | Nonreflective entrance surface on the minor prism 889 |
| 894 | Nonreflective exit surface on the mirror prism 889 |
| 92 | Tilted plane parallel plate, in particular with CaF2, upstream of a cyclical double beam interferometer for compensating astigmatism and coma |
| 93 | Tilted plane parallel plate, in particular with CaF2, in a first arm of a Mach-Zehnder Interferometer for compensating astigmatism and coma |
| 94 | Tilted plane parallel plate, in particular with CaF2, in a second arm of a Mach-Zehnder Interferometer for compensating astigmatism and coma |
| 95 | Tilted plane parallel plate, in particular with CaF2, downstream of a cyclical double beam interferometer for compensating astigmatism |
| 971 | First plane parallel plate, in particular with glass, of height h1, and in particular with optical material having the refractive index n1 and preferably with n1 < n2 |
| 972 | Second plane parallel plate, in particular with glass, of height h2, and in particular with optical material having the refractive index n2 and preferably with n1 < n2 |
| 973 | Carrier plate, in particular with glass, of height h1, and in particular with optical material having the refractive index n1 and preferably with n1 < n2 |
| 974 | Carrier plate, in particular with glass, of height h2, and in particular with optical material having the refractive index n2 and preferably with n1 < n2 |
| 975 | Double gap aperture on carrier plate 973 or 974 |
| 976 | First gap opening in the double gap aperture at 975, represents a field of view discriminator. |
| 977 | Second gap opening in the double gap aperture at 975, represents a field of view discriminator. |

-continued

| Reference symbols | Identifier |
|---|---|
| A | Point |
| a | Center distance of the gap openings, preferably corresponds to half the lateral shear s |
| alpha | Aperture angle, equivalent to half the opening angle |
| b | Width of the two field of view discriminators BFD1 and BFD2, which is preferably at least approximately equal.<br>In the cyclical double beam interferometer (605, 606, 607), b is the overall width of the nondiscriminating region, that is to say for example the opening of the latter, of a field of view discriminator in the revolving beam path.<br>The width b can be the gap width of a simple gap-shaped shading aperture 631 or 632 and/or the overall width of a finely-structured shading aperture. But the width b can also be the maximum width of the pass-through area of a liquid crystal display, even when the latter has a finely-structured pass-through area.<br>But the width b can also be the width of a narrow plane mirror that is used as a field of view discriminator and/or the overall width of reflecting micro-mirrors of a digital micro-mirror array.<br>The width b can also be the gap width of the gap aperture 645 (646) in the rooftop reflector 641a (641b), which can preferably be mapped to a computer-controllable piezo actuator 647. |
| b' | Width of the lateral measured object increment by an imagined reverse imaging of a gap-shaped opening of the two exactly adjusted field of view discriminators of equal construction, which are optically conjugated in relation to each other |
| bk | Width of the camera chip or the width of the surface of the raster detector |
| b_S | Width of the light source |
| b_S' | Width of the light stripe in a plane of the measured object vertically to the optical axis in the geometrical-optical image of the light source,<br>On non-scattering objects, the width of the light stripe b_S' from the image of the light source is at least approximately equal to the width b_80 of the light stripe on the measured object. |
| b_S" | Width of the light stripe in the plane of the gap aperture |
| b_80'1 | Width of the image of the light stripe 80, formed by the partial beam TB1 with mathematically positive directionality in the cyclical double beam interferometer 605, 606, 607 |
| b_80'2 | Width of the image of the light stripe 80, formed by the partial beam TB2 with mathematically positive directionality in the cyclical double beam interferometer 605, 606, 607 |
| B | Point |
| BEI12 | Common image plane in which the image planes BEI1 and BEI2 of the two revolving beam paths coincide in the cyclical double beam interferometer and are therefore optically conjugated, given perfect adjustment of the latter<br>The field of view discriminators BFD1 and BFD2 are also at least approximately physically located in the common image plane BEI12. |
| BEI1 | Image plane in the interferometer arm IA1 in which the field of view discriminator BFD1 is also located<br>The image plane BEI1 and the image plane BEI2 are preferably at least approximately optically conjugated. The difference of the positions of the two image planes BEI1 and BEI2 in the depth axis is preferably less than the wave-optical depth of field focal range, which the person skilled in the art determines from the numerical aperture of the partial beams TB1 and TB2, which is at least approximately equal, and the associated wavelength.<br>Both image planes BEI1 and BEI2 are preferably optically conjugated with the apparent end mirror surface SEF in a Michelson-Type Interferometer. This can present an advantage for the size of the aperture angle alpha. |
| BEI2 | Image plane in the interferometer arm IA2 in which the field of view discriminator BFD2 is also located |
| BFD1's | Apparent image of the first field of view discriminator BFD1 in the apparent image plane SBE12 |
| BFD1 | First field of view discriminator<br>The field of view discriminator BFD1 is mapped to the image plane BEI1.<br>A field of view discriminator can for example be a gap aperture 645, a pinhole array, a pass-through area 656, 657 of a liquid crystal display 655 and/or a narrow reflective region on a plane mirror and/or on a micro-mirror array and/or also a narrow plane mirror.<br>A field of view discriminator then has a non-discriminating region, for example formed as a relative fine opening for allowing light to pass through and/or a relatively narrow reflective region. |

-continued

| Reference symbols | Identifier |
|---|---|
| BFD2's | Apparent image of the second field of view discriminator BFD2 in the apparent image plane SBE12 |
| BFD2 | Second field of view discriminator, also refer to BFD1<br>The field of view discriminator BFD2 is mapped to the image plane BEI2. |
| BFD1'r | Real reverse-imaged of the first field of view discriminator BFD1 on the measured object<br>In the adjusted state of the double beam interferometer, the images BFD1'r and BFD2'r coincide and are then optically conjugated. |
| BFD2'r | Real reverse-imaged image of the second field of view discriminator BFD2 on the measured object |
| C | Point |
| d1, d2 | Thicknesses and/or heights of the mirror prisms 887 and 889<br>An advantage for synchronizing the double beam interferometer is when d1 = d2 is approximated, which is possible by manufacturing together |
| d_ST | Distance of the intersection SP from the beam splitter plane ET<br>The distance d_ST describes the asymmetry in a cyclical interferometer. |
| delta_a | Shifting of the image point O'1 caused by the adjustment movement delta_y |
| delta_beta | Angle between interfering wavefronts |
| DE | Detection plane of the interferograms |
| delta_sigma | Spectral resolution in the spectrum calculated by FFT, and that is approximately determined from the reciprocal value of the maximum optical distance difference OPD given a triangular apodization of the interferogram values, and stated in the unit of measure 1/cm (here: $cm^{-1}$) |
| delta_v | Image position difference in the depth axis in a cyclical double beam interferometer |
| dm_1 | Mirror distance of the plane mirrors 821 and 822 in the mirrored staircase 82<br>dm_1 > dm_2 applies. |
| dm_2 | Mirror distance of the plane mirrors 831 and 832 in the mirrored staircase 83<br>dm_1 > dm_2 applies. |
| E | Point |
| EB | Input beam |
| epsilon | Angle between the straight lines g1 and g2 in the reference plane RE in a cyclical double beam interferometer 605 to 615<br>The extended straight lines g1 and g2 are located in the plane mirrors (628, 629) or (671, 672) and/or in the plane mirror surfaces (681, 682), (687s, 688s), (689s, 696s) or (762, 764) and in the reference plane RE.<br>epsilon = 2psi applies. |
| E_S | Symmetry plane between the two plane mirrors and/or the plane mirror surfaces of a cyclical double beam interferometer, which also contains the half angle line between the two plane mirrors and/or plane mirror surfaces and the intersection SP |
| ET | Beam splitter plane |
| F511 (F521, F531, F581, F591) | Front focal point of the lens 511 in the downstream anamorphic lens 51 (52, 53, 58, 59) in they plane, which represents the reference plane RE |
| F'511 (F'521, F'531, F'581, F'591) | Rear focal point of the lens 511 in the downstream anamorphic lens 51 (52, 53, 58, 59) in the yz plane, which represents the reference plane RE |
| f511 (f521, f531, f581, f591) | Rear focal length of the lens 511 (521, 531, 581, 591) in downstream anamorphic lens 51(52, 53, 58, 59)<br>The following applies: f511 = f51yz<br>(f521 = f52yz, f531 = f53yz, f581 = f58yz, f591 = f59yz) |
| F51xz (F52xz, F53xz, F58xz, F59xz) | Front focal point of the anamorphic lens 51(52, 53, 58, 59) in the xz plane |
| F'51xz (F'52xz, F'53xz, F'58xz, F'59xz) | Rear focal point of the anamorphic lens 51(52, 53, 58, 59) in the xz plane<br>The following applies: F'511 = F'51yz<br>(F'521 = F'52yz, F'531 = F'53yz, F'581 = F'58yz, F'591 = F'59yz) |
| F51yz (F52yz, | Front focal point of the anamorphic lens 51(52, 53, 58, 59) in the yz plane, which represents the reference plane RE |

-continued

| Reference symbols | Identifier |
|---|---|
| F53yz, F58yz, F59yz) | The following applies: F511 = F51yz (F521 = F52yz, F531 = F53yz, F581 = F58yz, F591 = F59yz) |
| F'51yz (F'52yz, F'53yz, F'58yz, F'59yz) | Rear focal point of the anamorphic lens 51(52, 53, 58, 59) in the yz plane, which represents the reference plane RE |
| FFT | (Fast) Fourier Transformation, which is in particular used for calculating a spectrum from an interferogram |
| G | Point |
| go | Plumb line onto the mirror surface of a mirror prism 687 and/or 688 |
| g1 | Extended straight line in the reference plane RE in a cyclical interferometer 605 to 615 in the surface of the plane mirror 628 and/or the plane mirror 671 or of the mirror surface 681 and/or the mirror surface 762 or of the mirror surface 687s and/or the mirror surface 689s or of the mirror surface 888 |
| g2 | Extended straight line in a cyclical interferometer 605 to 615 in the surface of the plane mirror 629 and/or the plane mirror 672 or of the mirror surface 682 and/or the mirror surface 764 or of the mirror surface 688s and/or the mirror surface 696s or of the mirror surface 890 |
| h1 | Thickness of a first plane parallel plate with the refractive index n1 |
| h2 | Thickness of a second plane parallel plate with the refractive index n1 and/or n2 |
| HTB1, HTB2 | Main beams of the partial beams TB1 and TB2 |
| HEB | Main beam of the input beam |
| I | Intensity |
| IA1 | First arm of a double beam interferometer |
| IA2 | Second arm of a double beam interferometer |
| kappa | Angle in a cyclical double beam interferometer between the main beam HTB1a, which projects from the first mirrored staircase (82), and the main beam HTB2a, which projects from the second mirrored staircase (83). |
| L | Length of a field of view discriminator, for example in a gap opening |
| L' | Length of the image of a field of view discriminator, for example in a gap opening |
| n1 | Refractive index, e.g. nd = 1.517 for the glass N-BK7 |
| n2 | Refractive index, e.g. nd = 1.613 for the glass N-5K4 |
| O | Illuminated or self-luminescent object point on the measured object (1, 10, 14, 15, 16) on the axis of an upstream lens 70, 71, 73, 74, 75, 751 The image points O'1, O'1e, O'1s, O'2, O'2e, O'2s are optically conjugated to this image point O. |
| O'1 | Focused real image of the object point O in the interferometer |
| O'1e | Focused unfolded image of the image point O after partial geometric unfolding of the beam path of the first interferometer arm IA1 |
| O'1s | Completely unfolded apparent image point of the object point O upstream of the anamorphic lens, also by taking into account refractive materials in the beam path The completely unfolded apparent image point O'1s originates from the arm of the double beam interferometer arm IA1. |
| O'1_unfocused | Out of focus image spot of the object point O in the first interferometer arm IA1, caused by spherical aberration of plane parallel plates in the beam path |
| O'2 | Focused real image of the object point O in the interferometer |
| O'2e | Focused unfolded image of the image point O after partial geometric unfolding of the beam path of the second interferometer arm IA2 |
| O'2s | Completely unfolded apparent image point of the object point O upstream of the anamorphic lens, also by taking into account refractive materials in the beam path The completely unfolded apparent image point O'2s originates from the arm of the double beam interferometer arm IA2. |
| O"1_xz | Focused apparent image of the object point O on the output of the anamorphic lens 51, formed by a beam |
| OAI | Optical axis of the upstream lens 70, 71, 73, 74, 75 and/or also 751, which generally faces the double beam interferometer This optical axis coincides with the z axis. |
| OA2 | Optical axis of the camera, in particular an InGaAs camera |
| OE_1, OE_2, OE_3, OE_4 | The object elements OE_1, OE_2 OE_3, OE_4 are arranged in x direction, which then form a stripe-shaped measurement field. |

-continued

| Reference symbols | Identifier |
|---|---|
| OE | Object element |
| OPD | Optical distance difference, also the optical distance difference in the double beam interferometer (OPD) |
| OPDr | Optical distance difference, also the optical distance difference in the double beam interferometer (OPD), here the maximum achievable optical distance difference in the spatial interferogram on the edge of the raster detector, given a symmetric position of the spatial interferogram on the raster detector |
| OPDru | Maximum achievable optical distance difference on the edge of the raster detector, given an asymmetric position of the spatial interferogram The following can apply in a boundary case: OPDru = 2*OPDr. But in many cases, the achievable optimum is OPDru = 1.5*OPDr because the standard case requires a left-side interferogram for the phase correction when calculating the spectrum by FFT. |
| OPD_left | Maximum optical distance difference on the left side of the spatial interferogram rI, for an interferogram rI rendered with the optical distance difference OPD, as is commonly done in the industry |
| OPD_right | Maximum optical distance difference on the right side of the spatial interferogram rI, for an interferogram rI rendered with the optical distance difference OPD, as is commonly done in the industry The maximum optical distance difference OPD_right can correspond to the maximum achievable optical distance difference at the edge of the raster detector OPDru, given an asymmetric position of the spatial interferogram. |
| P | Point on a light source that is optically conjugated with the object point O |
| P' | Image of the point P after the latter is rendered through the lens 48 onto the measured object 14 and/or 15 |
| P"1 | Image of the point P' after the latter is rendered with an upstream lens 73 into the double beam interferometer The point P-1 coincides with the point O'1 in FIG. 13. |
| P"2 | Image of the point P'after the latter is rendered with an upstream lens 73 into the double beam interferometer The point P"2 coincides with the point O'2, which is shown in FIG. 12 and also in FIG. 13. |
| P"1s | Image of the point P' in the apparent image plane SBE12, mapped to the first interferometer arm IA1 |
| P"2s | Image of the point P'in the apparent image plane SBE12, mapped to the second interferometer arm IA2 |
| psi | The half angle of the cyclical double beam interferometer, and generally an acute angle, and psi is half the value of the angle epsilon In a cyclical double beam interferometer 605 to 615, the angle psi is half the value of the angle between the straight lines g1 and g2 in the reference plane RE. |
| RE | Reference plane The reference plane RE is spanned by the normal of the planar beam splitter surface and by the optical axis OAI of the upstream lens on the input of a double beam interferometer. The reference plane is then generally vertical in relation to the beam splitter surface. In a Mach-Zehnder Interferometer, the normal of the first beam splitter surface determines the reference plane RE. The raster detector is in a standard case vertical in relation to the reference plane RE. |
| rho | Angle |
| rI | Spatial interferogram |
| RZ | Radius of a cylindrical wave, which becomes very small or approaches zero on the raster detector |
| s | Lateral shear of the coherent image points O'1s, O'2s upstream of the anamorphic lens 51, 52, 53, 58, 59 and therefore also upstream of the partial beams TB1 and TB2 Depending on the arrangement, the lateral shear can also be formed as the sum and/or difference of s1 and s2. |
| s1 | Lateral shear after passing a first rooftop reflector shifted laterally to the partial beam TB1 |
| s2 | Lateral shear after passing a second rooftop reflector shifted laterally to the partial beam TB2 |
| S82 | Penetration point of the intersecting line through the reference plane RE of the extended mirror surfaces 821 and 822 of the mirrored staircase 82 |
| S83 | Penetration point of the intersecting line through the reference plane RE of the extended mirror surfaces 831 and 832 of the mirrored staircase 83 |
| SP | Intersection of the straight lines g1 and g2 in a cyclical double beam interferometer 605 to 615 in the reference plane RE, which here represents the drawing plane |

Reference symbol list with explanations

| Reference symbols | Identifier |
|---|---|
| sigma | Wave number in the unit of measure 1/cm ($cm^{-1}$), where 1 is divided by the wavelength in cm |
| Sp1, Sp2, SP3, SP4 | Spectrums<br>Each spectrum Sp1, Sp2, SP3, SP4 is respectively calculated from a spatial interferogram rI1, rI2, rI3, rI4 by FFT. |
| t | Time |
| t1, t2, t3, t4, t5, t6 | Points in time |
| tau_1 | Wedge angle between the two plane mirrors of the first mirrored staircase<br>The aim is to at least approximately achieve tau_1 = tau_2. |
| tau_2 | Wedge angle between the two plane mirrors of the second mirrored staircase |
| T | Point |
| TB1 | First partial beam after beam splitting<br>However, there are simultaneously a plurality of partial beams that each originate from an object point. The partial beam TB1 shown in the figures is therefore only representative for a plurality of such partial beams.<br>The partial beams TB1 and TB2 represent coherent beams. |
| TB2 | Second partial beam after beam splitting |
| va | Step between the surfaces of two mirror prisms |
| v1 | Image shift in the depth axis on a plane parallel plate of thickness h1 and with the refractive index n1 |
| v2 | Image shift in the depth axis on a plane parallel plate of thickness h2 and refractive index n1 and/or the refractive index n2 |
| SBE12 | Apparent image plane that is arranged upstream of every anamorphic lens 51, 52, 53, 58, 59 and which in turn represents the object plane for this lens 51, 52, 53, 58, 59. This apparent image plane SBE12 is determined by the geometric unfolding of the optical arrangement with all its optical components, and also by taking into account the refraction. The apparent image plane SBE12 only exists on the adjusted interferometer on which the image planes are also optically conjugated. In this case, the individual image planes SBE1 and SBE2 coincide to form a common apparent image plane SBE12 within the wave-optical depth of field focal range, which is the standard case in this document. |
| SEF1 | Apparent end mirror surface in the first arm IA1 of the double beam interferometer |
| SEF2 | Apparent end mirror surface in the second arm IA2 of the double beam interferometer |
| Xuv | Luminescent pixel in the UV range activated by a control computer |
| Xuv' | Image of the luminescent pixel Xuv in the UV range |
| Xvis"1 | Image of the luminescent pixel Xvis"1 in the VIS range in the first arm IA1 of the double beam interferometer |
| Xvis"2 | Image of the luminescent pixel Xvis"2 in the VIS range in the second arm IA2 of the double beam interferometer |
| x (direction) | Length direction of stripes, or length direction of a stripe light source and/or also a gap opening, generally vertically in relation to the reference plane RE |
| y (direction) | Direction of the lateral shear or the lateral direction in relation to a stripe in the unfolded state |
| Z | Region in a cyclical double beam interferometer (605 to 615) where there is no spatial overlap of any kind between the partial beams TB1 and TB2 |
| z (direction) | Propagation direction of the interference light in the detection direction<br>In the unfolded state of the optical arrangement, the z axis is vertical in relation to the raster detector.<br>The z axis always coincides with the optical axis OAI of the upstream lens. |
| $\Theta_1, \Theta_2, \Theta_3, \Theta_4$ | Angle between the first mirror 661a, 662a and the second mirror 661b, 662b of the first and the second beam deflection unit in the Mach-Zehnder Interferometer |

The invention claimed is:

1. A Fourier Transformation Spectrometer (FT spectrometer), comprising:
a double beam interferometer, comprising:
at least one beam splitter unit for splitting an incident light beam of a spatially expanded object into a first partial beam and a second partial beam;
at least one first beam deflection unit designed to deflect the first partial beam at least a first and a second time, wherein
the first beam deflection unit is designed to also deflect the second partial beam at least a first and a second time; or
the double beam interferometer comprises a second beam deflection unit designed to deflect the second partial beam at least a first and a second time, wherein the beam splitter unit is also designed to spatially at least partially overlay the first partial beam and the second partial beam, and wherein the respectively first and second deflection of the first partial beam and the second partial beam generates the lateral shear(s);

at least one first field of view discriminator unit arranged such that the first partial beam is spatially selected after the splitting and before the second deflection;

at least one second field of view discriminator unit arranged such that the second partial beam is spatially selected after the splitting and before the second deflection;

wherein the FT spectrometer additionally comprises:

at least one lens arranged opposite the beam splitter unit such that the incident light beam passes the lens at least partially before said light beam is split on the beam splitter unit and the first partial beam and the second partial beam respectively generate a plurality of coherent image points of the spatially expanded object in an image plane between the beam splitter unit and a detector;

the detector to record a plurality of spatial interferograms on the basis of the spatial overlay of the first partial beam and the second partial beam, which corresponds to the at least partial imaging of the plurality of coherent image points; and at least one computing unit for the Fourier transformation of the plurality of spatial interferograms to generate a plurality of spectrums, and based thereon, to generate a hyperspectral image of the spatially expanded object.

2. The FT spectrometer according to claim 1, wherein the beam splitter unit comprises a single beam splitter, in order to split the incident light beam of a spatially expanded object into the first partial beam and the second partial beam; and to at least partially spatially overlay the first partial beam and the second partial beam.

3. The FT spectrometer according to claim 1, wherein the first field of view discriminator unit and the second field of view discriminator unit are arranged in relation to each other such that at least approximate conjugation is created between the first field of view discriminator unit and the second field of view discriminator unit.

4. The FT spectrometer according to claim 1, wherein the double beam interferometer corresponds to a Michelson-Type Interferometer, comprising the second beam deflection unit, wherein the first beam deflection unit has a double mirror periscope reflector that hereinafter comprises:

a first mirror designed to reflect the first partial beam for at least a first time; and a second mirror that is arranged at an angle $\Theta_1$ in relation to the first mirror, and that is designed to reflect the first partial beam for at least a second time; and/or the second beam deflection unit has a further double mirror periscope reflector that hereinafter comprises:

a first mirror designed to reflect the second partial beam for at least a first time; and a second mirror that is arranged at an angle $\Theta_2$ in relation to the first mirror, and that is designed to reflect the second partial beam for at least a second time.

5. The FT spectrometer according to claim 1, wherein the double beam interferometer corresponds to a Michelson-Type Interferometer, comprising the second beam deflection unit, wherein the first beam deflection unit comprises a triple mirror periscope reflector that hereinafter comprises:

a first mirror designed to reflect the first partial beam for at least a first time; and a second mirror that is arranged at an angle $\Theta_1$ in relation to the first mirror, and that is designed to reflect the first partial beam for at least a second time; and a third mirror that is arranged at an angle $\Theta_1$ in relation to the first mirror and at an angle $\Theta_{b1}$ in relation to the second mirror, and that is designed to reflect the first partial beam for at least a third time; and/or the second beam deflection unit has a further triple mirror periscope reflector that hereinafter comprises:

a first mirror designed to reflect the second partial beam for at least a first time; and a second mirror that is arranged at an angle $\Theta_2$ in relation to the first mirror, and that is designed to reflect the second partial beam for at least a second time; and a third mirror that is arranged at an angle $\Theta_{a2}$ in relation to the first mirror and at an angle $\Theta_{b2}$ in relation to the second mirror, and that is designed to reflect the second partial beam for at least a third time, wherein the first field of view discriminator unit has an opening designed to spatially select the first partial beam after the first reflection using the first mirror of the first beam deflection unit and prior to the second reflection using the second mirror of the first beam deflection unit; and/or the second field of view discriminator unit has a further opening designed to spatially select the second partial beam after the first reflection using the first mirror of the second beam deflection unit and prior to the second reflection using the second mirror of the second beam deflection unit.

6. The FT spectrometer according to claim 1, wherein the double beam interferometer corresponds to a Michelson-Type Interferometer, comprising the second beam deflection unit, wherein the first beam deflection unit further comprises:

a first prism having:

a first reflection surface designed to reflect the first partial beam at least a first time; and a second reflection surface designed to reflect the first partial beam at least a second time; and/or the second beam deflection unit further comprises:

a second prism having a first reflection surface designed to reflect the second partial beam at least a first time; and a second reflection surface designed to reflect the second partial beam at least a second time.

7. The FT spectrometer according to claim 6, wherein the first field of view discriminator unit has an opening designed to spatially select the first partial beam after the splitting of the incident light beam using the beam splitter unit and prior to the first reflection of the first partial beam using the first reflection surface of the first prism; and/or the second field of view discriminator unit has an opening designed to spatially select the second partial beam after the splitting of the incident light beam using the beam splitter unit and prior to the first reflection of the second partial beam using the first reflection surface of the second prism.

8. The FT spectrometer according to claim 1, wherein the double beam interferometer corresponds to a Mach-Zehnder Interferometer, comprising the second beam deflection unit, and wherein the beam splitter unit further comprises:
- a first single beam splitter for splitting the incident light beam into the first partial beam and the second partial beam; and
- a second single beam splitter to at least partially spatially overlay the first partial beam and the second partial beam, wherein the first beam deflection unit further comprises:
- a first mirror designed to reflect the first partial beam for at least a first time; and
- a second mirror that is arranged at an angle $\Theta_3$ in relation to the first mirror, and that is designed to reflect the first partial beam for at least a second time; and/or wherein the second beam deflection unit further comprises:
- a first mirror designed to reflect the second partial beam for at least a first time; and
- a second mirror that is arranged at an angle $\Theta_4$ in relation to the first mirror, and that is designed to reflect the second partial beam for at least a second time.

9. The FT spectrometer according to claim 8, wherein the first field of view discriminator unit has an opening designed to spatially select the first partial beam after the first reflection using the first mirror of the first beam deflection unit and prior to the second reflection using the second mirror of the first beam deflection unit; and/or the second field of view discriminator unit has a further opening designed to spatially select the second partial beam after the first reflection using the first mirror of the second beam deflection unit and prior to the second reflection using the second mirror of the second beam deflection unit.

10. The FT spectrometer according to claim 1, wherein the double beam interferometer corresponds to a cyclical double beam interferometer, wherein the first beam deflection unit is designed to also deflect the second partial beam at least a first and a second time, the first field of view discriminator unit has an opening designed to spatially select the first partial beam after the first deflection and prior to the second deflection; and the second field of view discriminator unit has a further opening designed to spatially select the second partial beam after the first deflection and prior to the second deflection.

11. The FT spectrometer according to claim 10, wherein the beam deflection unit has a double mirror periscope reflector that hereinafter comprises:
- a first mirror designed to reflect the first partial beam at least a first time, and to reflect the second partial beam at least a second time; and
- a second mirror that is arranged at an angle epsilon in relation to the first mirror, and that is designed to reflect the second partial beam at least a first time and to reflect the first partial beam at least a second time.

12. The FT spectrometer according to claim 10, wherein the beam deflection unit has a double-prism arrangement that hereinafter comprises the following a first prism having at least one reflection surface designed to reflect the first partial beam at least a first time, and to reflect the second partial beam at least a second time; and a second prism having at least one reflection surface designed to reflect the second partial beam at least a first time, and to reflect the first partial beam at least a second time.

13. The FT spectrometer according to claim 10, wherein the first field of view discriminator unit has an opening designed to spatially select the first partial beam after the first reflection using the first mirror or the reflection surface of the first prism and prior to the second reflection using the second mirror or the reflection surface of the second prism; and the second field of view discriminator unit has a further opening designed to spatially select the second partial beam after the first reflection using the first mirror or the reflection surface of the second prism and prior to the second reflection using the first mirror or the reflection surface of the first prism.

14. A method for interferometric measurement using an FT spectrometer with a double beam interferometer, the method comprising:
- splitting an incident light beam transmitted from a spatially expanded object into a first partial beam and a second partial beam using a beam splitter unit;
- a first and second deflection of the first partial beam using a first beam deflection unit;
- a first and second deflection of the second partial beam using the first beam deflection unit or using a second beam deflection unit, wherein the first and second deflection of the first partial beam and the second partial beam generates a lateral shear(s);
- spatially selecting at least a part of the first partial beam after the splitting using a first field of view discriminator unit in the double beam interferometer; and
- spatially selecting at least a part of the second partial beam after the splitting using a second field of view discriminator unit in the double beam interferometer;
- sending the incident light beam through a lens prior to the splitting to generate a plurality of coherent image points of the spatially expanded object in an image plane between the beam splitter unit and a detector;
- at least partially spatially overlaying the first partial beam and the second partial beam using the beam splitter unit;
- at least partially rendering the plurality of coherent image points while at the same time generating a plurality of spatial interferograms on a detector field of the detector on the basis of the spatial overlay;
- recording the plurality of interferograms using the detector;
- Fourier transforming the plurality of spatial interferograms to generate a plurality of spectrums, and based thereon, generating a hyperspectral image of at least a section of the spatially expanded object.

15. The method for interferometric measurement according to claim 14, further comprising the steps initiated by at least one computer unit:
- multiple simultaneous recording of the plurality of spatial interferograms at respectively different points in time; and
- Fourier transforming the plurality of spatial interferograms recorded at respectively different points in time to generate a plurality of spectrums; and
- generating a hyperspectral image of the spatially expanded object.

16. The method for interferometric measurement according to claim 14, wherein the spatial selecting of the at least a part of the first partial beam occurs prior to the second deflection.

17. The method for interferometric measurement according to claim 14, wherein the spatial selecting of the at least a part of the first partial beam occurs after the second deflection.

18. The method for interferometric measurement according to claim 14, wherein the spatial selecting of the at least a part of the second partial beam occurs prior to the second deflection.

19. The method for interferometric measurement according to claim 14, wherein the spatial selecting of the at least a part of the second partial beam occurs after the second deflection.

\* \* \* \* \*